US012485242B2

(12) United States Patent
Pedersen et al.

(10) Patent No.: US 12,485,242 B2
(45) Date of Patent: Dec. 2, 2025

(54) RESPIRATORY INTERFACE ASSEMBLY

(71) Applicant: Fisher & Paykel Healthcare Limited, Auckland (NZ)

(72) Inventors: Matthew James Pedersen, Auckland (NZ); Yi-Jen Lin, Auckland (NZ); Stephen Francis Heffernan, Auckland (NZ); Bruce Michael Walls, Auckland (NZ); Wen Dong Huang, Auckland (NZ); Hamish Joshua Rose, Auckland (NZ); Priyanka Ferdinand Pereira, Auckland (NZ); Tony William Spear, Auckland (NZ); Kane Logan Findlay, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 898 days.

(21) Appl. No.: 17/768,116

(22) PCT Filed: Oct. 14, 2020

(86) PCT No.: PCT/NZ2020/050126

§ 371 (c)(1),
(2) Date: Apr. 11, 2022

(87) PCT Pub. No.: WO2021/075982

PCT Pub. Date: Apr. 22, 2021

(65) Prior Publication Data

US 2024/0293635 A1 Sep. 5, 2024

Related U.S. Application Data

(60) Provisional application No. 62/914,923, filed on Oct. 14, 2019.

(51) Int. Cl.
*A61M 16/06* (2006.01)

(52) U.S. Cl.
CPC .... *A61M 16/0616* (2014.02); *A61M 16/0666* (2013.01); *A61M 16/0683* (2013.01)

(58) Field of Classification Search
CPC .......... A61M 16/0616; A61M 16/0622; A61M 16/0666
See application file for complete search history.

(56) References Cited

U.S. PATENT DOCUMENTS 3,040,741 A 6/1962 Carolan
3,599,635 A 8/1971 Ansite
(Continued)

FOREIGN PATENT DOCUMENTS

CA 2153614 1/1996
DE 29723101 5/1998
(Continued)

OTHER PUBLICATIONS

Fisher & Paykel Healthcare, Product Profile—Overview: The Family of Interface Solutions (18043711RevB), circa 2004.
(Continued)

*Primary Examiner* — Joseph D. Boecker
(74) *Attorney, Agent, or Firm* — VIA LLP

(57) ABSTRACT

A respiratory interface assembly includes a patient interface and a headgear arrangement. A seal or cushion of the interface assembly can include thickened portions positioned and arranged to improve sealing and/or user comfort. The headgear arrangement can be connectable to the nasal mask by a connection arrangement configured to provide stability to the nasal mask such that a forehead support is not required. The connection arrangement can inhibit or prevent improper connections. The headgear arrangement can have one or more resilient straps having a composite construction of an outer fabric and a plastic core. The outer fabric can be
(Continued)

knitted. A rear portion of the headgear arrangement can include a knitted panel or a spacer fabric panel.

40 Claims, 31 Drawing Sheets

(56) References Cited

U.S. PATENT DOCUMENTS

| | | | |
|---|---|---|---|
| 3,861,381 | A | 1/1975 | Witman et al. |
| 4,454,881 | A | 6/1984 | Huber et al. |
| 4,790,306 | A | 12/1988 | Braun et al. |
| 5,074,297 | A | 12/1991 | Venegas |
| 5,355,878 | A | 10/1994 | Griffiths et al. |
| 5,657,752 | A | 8/1997 | Landis et al. |
| 5,724,965 | A | 3/1998 | Handke et al. |
| 5,863,312 | A | 1/1999 | Wolfe |
| 5,921,239 | A | 7/1999 | McCall et al. |
| 6,019,101 | A | 2/2000 | Cotner et al. |
| 6,112,746 | A | 9/2000 | Kwok et al. |
| 6,119,694 | A | 9/2000 | Correa et al. |
| 6,374,826 | B1 | 4/2002 | Gunaratnam et al. |
| 6,412,488 | B1 | 7/2002 | Barnett et al. |
| 6,467,483 | B1 | 10/2002 | Kopacko et al. |
| 6,470,886 | B1 | 10/2002 | Jestrabek-Hart |
| 6,615,834 | B2 | 9/2003 | Gradon et al. |
| 6,651,663 | B2 | 11/2003 | Barnett et al. |
| 6,659,102 | B1 | 12/2003 | Sico |
| 6,662,803 | B2 | 12/2003 | Gradon et al. |
| 6,752,149 | B2 | 6/2004 | Gillespie et al. |
| 6,892,729 | B2 | 5/2005 | Smith et al. |
| 6,907,882 | B2 | 6/2005 | Ging et al. |
| 7,047,972 | B2 | 5/2006 | Ging et al. |
| 7,318,437 | B2 | 1/2008 | Gunaratnam et al. |
| 7,341,060 | B2 | 3/2008 | Ging et al. |
| 7,353,827 | B2 | 4/2008 | Geist |
| 7,357,136 | B2 | 4/2008 | Ho et al. |
| 7,461,656 | B2 | 12/2008 | Gunaratnam et al. |
| 7,487,772 | B2 | 2/2009 | Ging et al. |
| 7,559,323 | B2 | 7/2009 | Hacke et al. |
| 7,597,100 | B2 | 10/2009 | Ging et al. |
| 7,743,767 | B2 | 6/2010 | Ging et al. |
| 7,874,291 | B2 | 1/2011 | Ging et al. |
| 7,874,293 | B2 | 1/2011 | Gunaratnam et al. |
| 7,900,635 | B2 | 3/2011 | Gunaratnam et al. |
| 7,926,487 | B2 | 4/2011 | Drew et al. |
| 7,938,116 | B2 | 5/2011 | Ging et al. |
| 7,942,150 | B2 | 5/2011 | Guney et al. |
| 7,997,267 | B2 | 8/2011 | Ging et al. |
| 8,025,057 | B2 | 9/2011 | Ging et al. |
| 8,042,542 | B2 | 10/2011 | Ging et al. |
| 8,042,546 | B2 | 10/2011 | Ging et al. |
| 8,186,352 | B2 | 5/2012 | Gunaratnam et al. |
| 8,286,636 | B2 | 10/2012 | Gunaratnam et al. |
| 8,312,881 | B2 | 11/2012 | Gunaratnam et al. |
| 8,312,883 | B2 | 11/2012 | Gunaratnam et al. |
| 8,371,302 | B2 | 2/2013 | Ging et al. |
| 8,387,616 | B2 | 3/2013 | Ging et al. |
| 8,397,727 | B2 | 3/2013 | Ng et al. |
| 8,424,530 | B2 | 4/2013 | Gunaratnam et al. |
| 8,439,035 | B2 | 5/2013 | Dantanarayana et al. |
| 8,479,736 | B2 | 7/2013 | Ging et al. |
| 8,550,084 | B2 | 10/2013 | Ng et al. |
| 8,573,201 | B2 | 11/2013 | Rummery et al. |
| 8,573,211 | B2 | 11/2013 | Ho et al. |
| 8,573,212 | B2 | 11/2013 | Lynch et al. |
| 8,622,057 | B2 | 1/2014 | Ujhazy et al. |
| 8,678,003 | B2 | 3/2014 | Darkin et al. |
| 8,800,563 | B2 | 8/2014 | Doherty et al. |
| 8,833,370 | B2 | 9/2014 | Ging et al. |
| 8,851,078 | B2 | 10/2014 | Newman et al. |
| 8,863,745 | B2 | 10/2014 | Ging et al. |
| 8,869,797 | B2 | 10/2014 | Davidson et al. |
| 8,944,058 | B2 | 2/2015 | Ging et al. |
| 8,944,059 | B2 | 2/2015 | Mansour et al. |
| 8,950,403 | B2 | 2/2015 | Howard et al. |
| 8,950,404 | B2 | 2/2015 | Formica et al. |
| 8,955,517 | B2 | 2/2015 | Chu et al. |
| 8,967,146 | B2 | 3/2015 | Veliss et al. |
| 8,985,117 | B2 | 3/2015 | Gunaratnam et al. |
| 8,997,742 | B2 | 4/2015 | Moore et al. |
| 9,010,330 | B2 | 4/2015 | Barlow et al. |
| 9,044,564 | B2 | 6/2015 | Dravitzki et al. |
| 9,149,593 | B2 | 10/2015 | Dravitzki et al. |
| 9,174,018 | B2 | 11/2015 | Ho et al. |
| 9,421,340 | B2 | 8/2016 | Ging et al. |
| 9,457,162 | B2 | 10/2016 | Ging et al. |
| 9,480,809 | B2 | 11/2016 | Guney et al. |
| 9,604,023 | B2 | 3/2017 | Matula et al. |
| 9,669,180 | B2 | 6/2017 | Ging et al. |
| 9,717,870 | B2 | 8/2017 | Kwok et al. |
| 9,789,274 | B2 | 10/2017 | Madaus et al. |
| 9,802,018 | B2 | 10/2017 | Ging et al. |
| 9,889,267 | B2 | 2/2018 | Wells et al. |
| 9,981,102 | B2 | 5/2018 | Veliss et al. |
| 9,993,605 | B2 | 6/2018 | Barlow et al. |
| 10,124,139 | B2 | 11/2018 | Matula, Jr. |
| 10,166,355 | B2 | 1/2019 | Eves et al. |
| 10,201,678 | B2 | 2/2019 | Guney et al. |
| 10,232,137 | B2 | 3/2019 | Romagnoli et al. |
| 10,265,488 | B2 | 4/2019 | Melidis et al. |
| 10,265,490 | B2 | 4/2019 | Barlow et al. |
| 10,265,492 | B2 | 4/2019 | Amarasinghe et al. |
| 10,300,235 | B2 | 5/2019 | Romagnoli et al. |
| 10,307,555 | B2 | 6/2019 | Ging et al. |
| 10,335,568 | B2 | 7/2019 | Amarasinghe et al. |
| 10,500,424 | B2 | 12/2019 | Rummery et al. |
| 10,518,058 | B2 | 12/2019 | Gunaratnam et al. |
| 10,543,332 | B2 | 1/2020 | Scheiner et al. |
| 10,556,084 | B2 | 2/2020 | Gunaratnam et al. |
| 10,561,813 | B2 | 2/2020 | Gunaratnam et al. |
| 10,569,044 | B2 | 2/2020 | Dunn et al. |
| 10,646,675 | B2 | 5/2020 | Chang |
| 10,688,266 | B2 | 6/2020 | Cullen et al. |
| 10,695,521 | B2 | 6/2020 | Harrington |
| 10,695,527 | B2 | 6/2020 | Dantanarayana |
| 10,709,852 | B2 | 7/2020 | Engelbreth et al. |
| 10,729,867 | B2 | 8/2020 | Ging et al. |
| 10,765,824 | B2 | 9/2020 | Lee et al. |
| 10,814,087 | B2 | 10/2020 | Ging et al. |
| 11,534,566 | B2 | 12/2022 | Spear et al. |
| 2002/0005201 | A1 | 1/2002 | Gradon et al. |
| 2002/0014241 | A1 | 2/2002 | Gradon et al. |
| 2003/0019496 | A1* | 1/2003 | Kopacko ........... A61M 16/0616 128/205.25 |
| 2005/0011524 | A1 | 1/2005 | Thomlinson et al. |
| 2005/0056286 | A1 | 3/2005 | Huddart et al. |
| 2005/0076913 | A1 | 4/2005 | Ho et al. |
| 2006/0060200 | A1 | 3/2006 | Ho et al. |
| 2008/0092906 | A1 | 4/2008 | Gunaratnam et al. |
| 2009/0139526 | A1 | 6/2009 | Melidis et al. |
| 2009/0151729 | A1 | 6/2009 | Judson et al. |
| 2014/0166019 | A1 | 6/2014 | Ho et al. |
| 2014/0174446 | A1* | 6/2014 | Prentice ............ A61M 16/0605 128/205.25 |
| 2014/0311496 | A1 | 10/2014 | Rothermel |
| 2014/0345618 | A1 | 11/2014 | Kwok et al. |
| 2015/0136138 | A1 | 5/2015 | Pastoor et al. |
| 2015/0196726 | A1 | 7/2015 | Skipper et al. |
| 2015/0246198 | A1 | 9/2015 | Bearne et al. |
| 2016/0022944 | A1* | 1/2016 | Chodkowski ..... A61M 16/0616 128/206.24 |
| 2016/0038708 | A1 | 2/2016 | Amarasinghe et al. |
| 2016/0082214 | A1 | 3/2016 | Barlow et al. |
| 2016/0114118 | A1 | 4/2016 | Gunaratnam et al. |
| 2016/0144144 | A1 | 5/2016 | Smith et al. |
| 2016/0256655 | A1 | 9/2016 | Mah et al. |
| 2016/0271351 | A1 | 9/2016 | Frater et al. |
| 2016/0296720 | A1 | 10/2016 | Henry et al. |
| 2016/0339196 | A1* | 11/2016 | Bowsher ........... A61M 16/0622 |
| 2017/0080174 | A1 | 3/2017 | Eves et al. |
| 2017/0128687 | A1 | 5/2017 | Price et al. |
| 2017/0165444 | A1 | 6/2017 | Rummery et al. |
| 2017/0182273 | A1 | 6/2017 | Ho et al. |
| 2017/0224944 | A1 | 8/2017 | Gunaratnam et al. |

(56) References Cited

U.S. PATENT DOCUMENTS

| | | | |
|---|---|---|---|
| 2017/0232219 A1 | 8/2017 | Dravitzki et al. | |
| 2017/0252528 A1 | 9/2017 | Ging et al. | |
| 2017/0326320 A1 | 11/2017 | Baigent et al. | |
| 2017/0368285 A1 | 12/2017 | Wood | |
| 2018/0140795 A1 | 5/2018 | Wells et al. | |
| 2018/0161535 A1 | 6/2018 | Henry | |
| 2018/0185598 A1* | 7/2018 | Olsen | A61M 16/0694 |
| 2018/0243522 A1 | 8/2018 | Ng et al. | |
| 2018/0250486 A1 | 9/2018 | Amarashinghe et al. | |
| 2018/0256844 A1 | 9/2018 | Galgali et al. | |
| 2018/0289916 A1 | 10/2018 | Gunaratnam et al. | |
| 2019/0009046 A1 | 1/2019 | Kooij et al. | |
| 2019/0105454 A1 | 4/2019 | Davidson et al. | |
| 2019/0125996 A1 | 5/2019 | Bentley et al. | |
| 2019/0217040 A1 | 7/2019 | Amarashinghe et al. | |
| 2019/0232013 A1 | 8/2019 | Yu et al. | |
| 2019/0240440 A1 | 8/2019 | Ging et al. | |
| 2019/0298959 A1 | 10/2019 | Barlow et al. | |
| 2020/0001034 A1 | 1/2020 | Chen et al. | |
| 2020/0046930 A1 | 2/2020 | Ging et al. | |
| 2020/0061398 A1 | 2/2020 | Rummery et al. | |
| 2020/0179636 A1 | 6/2020 | Gunaratnam et al. | |
| 2020/0197645 A1 | 6/2020 | Baiko | |
| 2020/0261685 A1 | 8/2020 | Skipper et al. | |
| 2021/0252241 A1* | 8/2021 | Davidson | A61M 16/0616 |

FOREIGN PATENT DOCUMENTS

| | | |
|---|---|---|
| DE | 202014104150 U1 | 10/2014 |
| EP | 0392498 | 10/1990 |
| EP | 1057494 | 12/2000 |
| EP | 1099452 | 5/2001 |
| EP | 1314445 | 5/2003 |
| EP | 3254721 | 12/2017 |
| GB | 160632 A | 3/1921 |
| NZ | 619618 | 8/2015 |
| NZ | 624925 | 10/2016 |
| NZ | 630695 | 6/2017 |
| NZ | 737918 | 6/2019 |
| NZ | 742407 | 11/2019 |
| NZ | 756942 | 5/2020 |
| WO | WO 2000/078383 | 12/2000 |
| WO | WO 2000/078384 | 12/2000 |
| WO | WO 0132250 | 5/2001 |
| WO | WO 0197892 | 12/2001 |
| WO | WO 0207806 | 1/2002 |
| WO | WO 2002/047749 | 6/2002 |
| WO | WO 2005/032634 | 4/2005 |
| WO | WO 2005/118042 | 12/2005 |
| WO | WO 2006/069415 | 7/2006 |
| WO | WO 2008/007985 | 1/2008 |
| WO | WO 2012/140514 | 10/2012 |
| WO | WO 2012/140514 A1 | 10/2012 |
| WO | WO 2013/006065 | 1/2013 |
| WO | WO 2014/062070 | 4/2014 |
| WO | WO 2014/182179 | 11/2014 |
| WO | WO 2015/009172 A1 | 1/2015 |
| WO | WO 2015/177716 | 11/2015 |
| WO | WO 2016/009393 A1 | 1/2016 |
| WO | WO 2016/032343 | 3/2016 |
| WO | WO 2016/072868 A1 | 5/2016 |
| WO | WO 2017/160166 | 9/2017 |
| WO | WO 2017/216708 A1 | 12/2017 |
| WO | WO 2018/009080 | 1/2018 |
| WO | WO 2018/065926 | 4/2018 |
| WO | WO 2020/170207 | 8/2020 |
| WO | WO 2020/188495 | 9/2020 |

OTHER PUBLICATIONS

Fisher & Paykel Healthcare, FlexitFit405 Nasal Mask—Patient Instructions for Use (185042841 Rev E), circa 2007.

International Search Report and Written Opinion in PCT/NZ2020/050126, filed on Oct. 14, 2020.

* cited by examiner

RESPIRATORY INTERFACE ASSEMBLY

CROSS-REFERENCE TO RELATED APPLICATIONS

The present application claims the priority benefit of U.S. Provisional Patent Application No. 62/914,923, filed on 14 Oct. 2019, which is hereby incorporated by reference in its entirety.

BACKGROUND

Field

The present disclosure relates to a respiratory interface assembly. In particular, the present disclosure relates to a nasal mask assembly having a nasal mask, a headgear and a connection between the mask and the headgear.

Description of Related Art

In assisted breathing, respiratory gases are supplied to a patient through a patient interface via one or more flexible breathing tubes. The patient interface can be a nasal cannula, nasal mask, full face or oro-nasal mask, endotracheal tube, or other known types of interfaces. The patient interface is held in place on the head of the user by a headgear arrangement.

It would be advantageous to provide a patient interface system having improved operation, sealing, comfort or adjustment features. Such a system may be a nasal mask assembly. Such an improved system may further assist with improved compliance of gas delivery treatment.

In the specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

Further aspects and advantages of the present disclosure will become apparent from the ensuing description which is given by way of example only.

SUMMARY

The systems, methods and devices described herein have innovative aspects, no single one of which is indispensable or solely responsible for their desirable attributes. Without limiting the scope of the claims, some of the advantageous features will now be summarized.

An aspect of the present disclosure involves a respiratory interface assembly including an interface configured to communicate with an airway of a user. The interface comprises a frame having a post. The frame defines an opening, wherein the post defines a portion of the opening. The frame opening comprises a narrowed portion defined by opposed upper and lower surfaces, the narrowed portion located adjacent the post. A headgear is configured to secure the interface in an operable position on the head of the user. The headgear includes a clip having a base and a hook portion extending from the base. The hook portion is configured to engage the post of the frame. The hook portion comprises an upper surface and a lower surface that substantially match a shape of the respective upper and lower surfaces of the narrowed portion whereby when the hook portion is engaged with the post, the upper surface and the lower surface of the hook portion engage respective ones of the opposed upper and lower surfaces of the narrowed portion to resist rotation of the clip relative to the frame about an axis perpendicular to a longitudinal axis of the post.

In some configurations, a section of the hook portion between the upper surface and the lower surface of the hook portion is shaped to span the space when the hook portion is engaged with the post.

In some configurations, the post and the opposed upper and lower surfaces cooperate to define a space. A section of the hook portion between the upper surface and the lower surface occupies a substantial entirety of the space when the hook portion is engaged with the post.

In some configurations, the opposed upper and lower surfaces are parallel to one another.

In some configurations, the hook portion defines an interior surface facing the post, an exterior surface and a thickness between the interior surface and the exterior surface. The thickness is greatest in a portion that is located between the opposed upper and lower surfaces when the hook portion is engaged with the post.

In some configurations, the base of the clip has a height that is greater than a height of the hook portion such that the base is configured to contact a portion of the frame adjacent the opposed upper and lower surfaces of the narrowed portion to limit rotation of the clip about a longitudinal axis of the post.

In some configurations, the headgear comprises at least one semi-rigid side strap configured to extend from the respiratory interface toward the ear of a user along each side of the user's face, and at least one semi-rigid top strap that extends from the at least one semi-rigid side strap a first side of the user's face to the at least one semi-rigid side strap on a second side of the user's face.

In some configurations, the at least one semi-rigid side strap comprises a bifurcated portion on each side, each of the bifurcated portions having an upper strap portion and a lower strap portion.

In some configurations, the headgear further comprises a rear portion, wherein the upper strap portion connects to the rear portion above the level of the user's ear and the lower strap portion connects to the rear portion below the level of and in front of the user's ear.

In some configurations, the rear portion comprises a spacer fabric panel.

In some configurations, the rear portion further comprises an upper strap and a lower strap, wherein the upper strap is less stretchable than the lower strap.

In some configurations, the rear portion comprises a knitted panel.

In some configurations, the knitted panel is less stretchable in the vertical direction than in the horizontal direction.

In some configurations, one or both of the at least one semi-rigid side strap and the at least one semi-rigid top strap comprises a fabric inner layer, a fabric outer layer and an interior plastic layer joined by the interior plastic layer being introduced between the fabric inner layer and the fabric outer layer in a molten state and allowed to harden.

In some configurations, the fabric inner layer and the fabric outer layer are knitted.

In some configurations, the at least one semi-rigid side strap comprises a first semi-rigid side strap and a second semi-rigid side strap, wherein each of the first and second semi-rigid side straps are connectable to the frame by one of the clips.

In some configurations, the at least one semi-rigid top strap comprises a first semi-rigid top strap and a second semi-rigid top strap, wherein the first and second semi-rigid tops straps are selectively connectable to one another in one of a plurality of available adjustment positions.

In some configurations, the interface comprises a nasal mask seal configured to seal around one or both nares of the user, the nasal mask seal having a sealing surface defining an opening.

In some configurations, the opening defined by the sealing surface of the nasal mask seal defines a width to height ratio of between about 1.3-1.6.

In some configurations, a height range of the nasal mask seal across all available sizes is between about 47.8 mm-57.8 mm.

In some configurations, the nasal mask seal comprises a rolling bridge portion.

In some configurations, the nasal mask seal comprises a rim at which the nasal mask seal is secured to a rigid clip or housing, wherein the rolling bridge portion connects to a rearward edge of the rim. In other configurations, the rolling bridge portion connects to a forward edge of the rim.

In some configurations, the nasal mask seal further comprises a thickened band located between the sealing surface and the rolling bridge, further comprising a pair of thickened pads the extend from the thickened band toward the opening on each side of the nasal mask seal.

In some configurations, the nasal mask seal further comprises a thickened band located between the sealing surface and the rolling bridge, a pair of thickened pads intermediate the thickened band and the opening and spaced from the thickened band, and a pair of joining pads extending between a portion of the thickened band and a portion of a respective one of the pair of thickened pads.

In some configurations, the thickened band is thicker than the pair of thickened pads, and the pair of thickened pads are thicker than the pair of joining pads.

In some configurations, the pair of thickened pads and the pair of joining pads each have a length extending in a peripheral direction around the inside of the nasal mask seal, and the length of each of the pair of joining pads is between about 15% and 50%, preferably about 20% and 45%, and more preferably about 25% and 33%, of the length of each of the pair of thickened pads.

In some configurations, each of the pair of joining pads extends between a portion of the thickened band and an upper portion of a respective one of the pair of thickened pads.

In some configurations, the pair of joining pads are provided to a side wall of the nasal mask seal on opposing sides of the nasal mask seal, and at least a portion of the pair of thickened pads are provided to an end wall defining the sealing surface of the nasal mask seal.

In some configurations, the nasal mask seal comprises a pair of elongate thickened portions, the pair of thickened portions each extending from a first end at or adjacent or near to respective lower corners of a side wall of the nasal mask seal at or adjacent or near to a rim, to a second end at or adjacent or near to an end wall defining the sealing surface of the nasal mask seal.

In some configurations, the pair of thickened portions diverge from the first ends towards respective intermediate portions of the pair of thickened portions.

In some configurations, the pair of thickened portions converge from respective intermediate portions of the pair of thickened portions towards the second ends.

In some configurations, each of the pair of elongate thickened portions are curved in a direction substantially normal to their respective major surfaces.

An aspect of the present disclosure involves a headgear for a respiratory interface including at least one resilient side strap configured to extend from the respiratory interface toward the ear of a user along each side of the user's face and at least one resilient top strap that extends from the at least one resilient side strap on a first side of the user's face to the at least one resilient side strap on a second side of the user's face.

An aspect of the present disclosure involves a headgear for a respiratory interface including at least one semi-rigid side strap configured to extend from the respiratory interface toward the ear of a user along each side of the user's face and at least one semi-rigid top strap that extends from the at least one semi-rigid side strap on a first side of the user's face to the at least one semi-rigid side strap on a second side of the user's face.

In some configurations, the at least one semi-rigid side strap comprises a bifurcated portion on each side, each of the bifurcated portions having an upper strap portion and a lower strap portion.

In some configurations, the headgear further comprises a rear portion, wherein the upper strap portion connects to the rear portion above the level of the user's ear and the lower strap portion connects to the rear portion below the level of and in front of the user's ear.

In some configurations, the rear portion comprises a spacer fabric panel.

In some configurations, the rear portion further comprises an upper strap and a lower strap, wherein the upper strap is less stretchable than the lower strap.

In some configurations, the rear portion comprises a knitted panel.

In some configurations, the knitted panel is less stretchable in the vertical direction than in the horizontal direction.

In some configurations, one or both of the at least one semi-rigid side strap and the at least one semi-rigid top strap comprises a fabric inner layer, a fabric outer layer and an interior plastic layer joined by the interior plastic layer being introduced between the fabric inner layer and the fabric outer layer in a molten state and allowed to harden.

In some configurations, the fabric inner layer and the fabric outer layer are knitted.

In some configurations, the at least one semi-rigid top strap comprises a first semi-rigid top strap and a second semi-rigid top strap, wherein the first and second semi-rigid tops straps are selectively connectable to one another in one of a plurality of available adjustment positions.

In some configurations, the at least one semi-rigid side strap is formed from at least one tubular knitted structure injection molded with a semi-rigid plastic core.

In some configurations, wherein at least one of the top strap, upper strap portion and lower strap portion of the at least one side strap comprises a separate tubular knitted structure injection molded with a plastic core, and joined to the at least one side strap by an overmolded joining portion.

An aspect of the present disclosure involves a respiratory interface assembly including any of the headgear described above and an interface configured to communicate with an airway of a user.

In some configurations, the interface comprises a frame having a post, the frame defining an opening, wherein the post defines a portion of the opening. The frame opening comprises a narrowed portion defined by opposed upper and lower surfaces. The narrowed portion is located adjacent the post. The headgear comprises a clip having a base and a hook portion extending from the base. The hook portion is configured to engage the post of the frame. The hook portion comprises an upper surface and a lower surface that substantially match a shape of respective upper and lower surfaces of the narrowed portion whereby when the hook portion is engaged with the post, the upper surface and the lower surface of the hook portion engage respective ones of the opposed upper and lower surfaces of the narrowed portion to resist vertical rotation of the clip relative to the frame about an axis perpendicular to a longitudinal axis of the post.

In some configurations, a section of the hook portion between the upper surface and the lower surface of the hook portion is shaped to span the space when the hook portion is engaged with the post.

In some configurations, the post and the opposed upper and lower surfaces cooperate to define a space, wherein a section of the hook portion between the upper surface and the lower surface occupies a substantial entirety of the space when the hook portion is engaged with the post.

In some configurations, the opposed upper and lower surfaces are parallel to one another.

In some configurations, the hook portion defines an interior surface facing the post, an exterior surface and a thickness between the interior surface and the exterior surface, wherein the thickness is greatest in a portion that is located between the opposed upper and lower surfaces when the hook portion is engaged with the post.

In some configurations, the base of the clip has a height that is greater than a height of the hook portion such that the base is configured to contact a portion of the frame adjacent the opposed upper and lower surfaces of the narrowed portion to limit rotation of the clip about a longitudinal axis of the post.

In some configurations, the at least one semi-rigid side strap comprises a first semi-rigid side strap and a second semi-rigid side strap, wherein each of the first and second semi-rigid side straps are configured to connectable to the frame by one of the clips.

In some configurations, the interface comprises a nasal mask seal configured to seal around one or both nares of the user, the nasal mask seal having a sealing surface defining an opening.

In some configurations, the opening defined by the sealing surface of the nasal mask seal defines a width to height ratio of between about 1.3-1.6.

In some configurations, a height range of the nasal mask seal across all available sizes is between about 47.8 mm-57.8 mm.

In some configurations, the nasal mask seal comprises a rolling bridge portion.

In some configurations, the nasal mask seal comprises a rim at which the nasal mask seal is secured to a rigid clip or housing, wherein the rolling bridge portion connects to a rearward edge of the rim.

In some configurations, the nasal mask seal further comprises a thickened band located between the sealing surface and the rolling bridge, further comprising a pair of thickened pads that extend from the thickened band toward the opening on each side of the nasal mask seal.

An aspect of the present disclosure involves a cushion for a respiratory interface assembly, the cushion comprising a rim attached or configured for attachment to a housing of the respiratory interface assembly; a resilient side wall extending from the rim; a resilient end wall extending inwardly from the resilient side wall, the end wall defining a sealing surface to seal with a user's face and an opening to receive the nose and/or mouth of the user, in use; a thickened band in the side wall; a pair of thickened pads intermediate the thickened band and the opening and spaced from the thickened band; and a pair of joining pads intermediate respective portions of the thickened band and a portion of a respective one of the pair of thickened pads.

In some configurations, the thickened band is thicker than the pair of thickened pads, and/or the pair of thickened pads are thicker than the pair of joining pads.

In some configurations, the pair of thickened pads and the pair of joining pads each have a length extending in a peripheral direction around the inside of the cushion, and the length of each of the pair of joining pads is between about 15% and 50%, preferably about 20% and 45%, and more preferably about 25% and 33%, of the length of each of the pair of thickened pads.

In some configurations, each of the pair of joining pads extends between a portion of the thickened band and an upper portion of a respective one of the pair of thickened pads.

In some configurations, the pair of joining pads are provided to a side wall of the nasal mask seal on opposing sides of the nasal mask seal, and at least a portion of the pair of thickened pads are provided to a face contacting surface of the nasal mask seal.

An aspect of the present disclosure involves a cushion for a respiratory interface assembly, the cushion comprising: a rim configured for attachment to a housing of the respiratory interface assembly; a resilient side wall extending from the rim; a resilient end wall extending inwardly from the resilient side wall, the end wall defining a sealing surface to seal with a user's face and an opening to receive the nose and/or mouth of the user, in use; and a pair of elongate thickened portions, the pair of thickened portions each extending from a first end at or adjacent or near to respective lower corners of the side wall at or adjacent or near to the rim, to a second end at or adjacent or near to the end wall on respective opposing sides of the opening.

In some configurations, the pair of thickened portions diverge from the first ends towards respective intermediate portions of the pair of thickened portions.

In some configurations, the pair of thickened portions converge from respective intermediate portions of the pair of thickened portions towards the second ends.

In some configurations, each of the pair of elongate thickened portions are curved in a direction substantially normal to their respective major surfaces.

An aspect of the present disclosure involves a connection arrangement for connecting a headgear strap to an interface of a patient interface assembly, the connection arrangement comprising: a post provided to or configured to be provided to one of the headgear strap or the patient interface assembly; a clip provided to the other of the headgear strap or the patient interface, the clip comprising a base portion and a hook portion defining therebetween a space configured to selectively receive the post; a gap provided to one of the post or the clip; and a rib provided to the other of the post or the clip, wherein the rib and the gap are each disposed asymmetrically so that the rib is received by the gap when the clip is connected to the post, and the rib is configured to inhibit or prevent an alternative connection.

In some configurations, the gap is provided to the post and defined between first and second coaxially-aligned post portions; the rib is provided to the clip and projects into the space; the rib is configured to be received by the gap when the post is received by the space; and the rib is configured to inhibit or prevent connection of the clip to an alternative post.

In some configurations, the rib is provided to the post; the gap is provided to the clip; the rib is configured to be received by the gap when the post is received by the space; and the rib is configured to inhibit or prevent connection of an alternative clip to the post.

An aspect of the present disclosure involves a headgear assembly for securing a patient interface to the head of a patient, the headgear assembly comprising: two or more straps; and two or more headgear clips provided to or configured to be provided to the two or more straps, at least a first clip of the two or more headgear clips comprising a base portion and a hook portion defining therebetween a space configured to selectively receive a post of the patient interface, and further comprising a rib projecting into the space, the rib being disposed asymmetrically along a length of the space so as to be received by a gap defined in at least a first post of the patient interface when the first clip is coupled with the first post, and to impede or prevent coupling of the first clip with a second post of the patient interface.

In some configurations, a second clip of the two or more headgear clips comprises a base portion and a hook portion defining therebetween a space configured to selectively receive a post of the patient interface, and further comprises a rib projecting into the space, the rib being disposed asymmetrically along a length of the space so as to be received by a gap defined in at least a second post of the patient interface when the second clip is coupled with the second post, and to impede or prevent coupling of the second clip with the first post.

In some configurations, the first clip and the second clip are mirror images of each other.

An aspect of the present disclosure involves a headgear clip for attaching a headgear to a patient interface assembly, the headgear clip comprising: a base portion attached to, or configured to be attached to, a strap of the headgear at a first end; a hook portion projecting from a second end of the base portion and defining a space configured to selectively receive a post of the patient interface assembly; and a projection extending outwardly from an outer side of the base portion.

In some configurations, the projection is disposed at or adjacent or near the first end of the base portion.

In some configurations, the headgear clip further comprises a depression in the outer side of the base portion, intermediate the second end and the projection.

In some configurations, at least the hook portion and a first part of the base portion comprises a resilient and relatively rigid first material, and at least a second part of the base portion comprises an elastomeric second material overmolded to the first material.

In some configurations, the second material is also overmolded to the strap.

In some configurations, the first part of the base portion comprises an inner portion of the projection, and the second part of the base portion comprises an outer portion of the projection.

In some configurations, the projection spans a width of the base portion.

In some configurations, the projection provides at least one surface which is substantially orthogonal to a direction of force required to engage or disengage the hook portion and the post.

In some configurations, the frame comprises or is configured to be coupled with a cushion for sealing engagement with a patient's face, and the frame comprises first and second posts configured to be coupled with first and second headgear clips of a headgear assembly of the patient interface assembly, the first post comprising a first portion and a second portion arranged coaxially and defining a gap therebetween, wherein the gap is disposed asymmetrically in an axial direction.

In some configurations, the second post is a mirror image of the first post.

In some configurations, the first post is configured to couple with the first headgear clip, and impeded or prevent coupling with the second headgear clip.

Further aspects of the present disclosure will be apparent from the following description and the accompanying drawings.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through the use of the accompanying drawings.

FIG. 6-1 is the sectional view of the cushion of FIGS. 3 and 4 with a prior art Eson 2 cushion superimposed on the present cushion.

FIG. 6-2 is the rear view of the cushion of FIG. 5 with the prior art Eson 2 cushion superimposed on the present cushion.

FIG. 12-1 is the sectional view of the connection arrangement of FIG. 12 with example dimensions shown.

FIGS. 32-1 and 32-2 illustrate an example method of knitting the knitted panel of FIG. 30.

DETAILED DESCRIPTION

Figure 1:
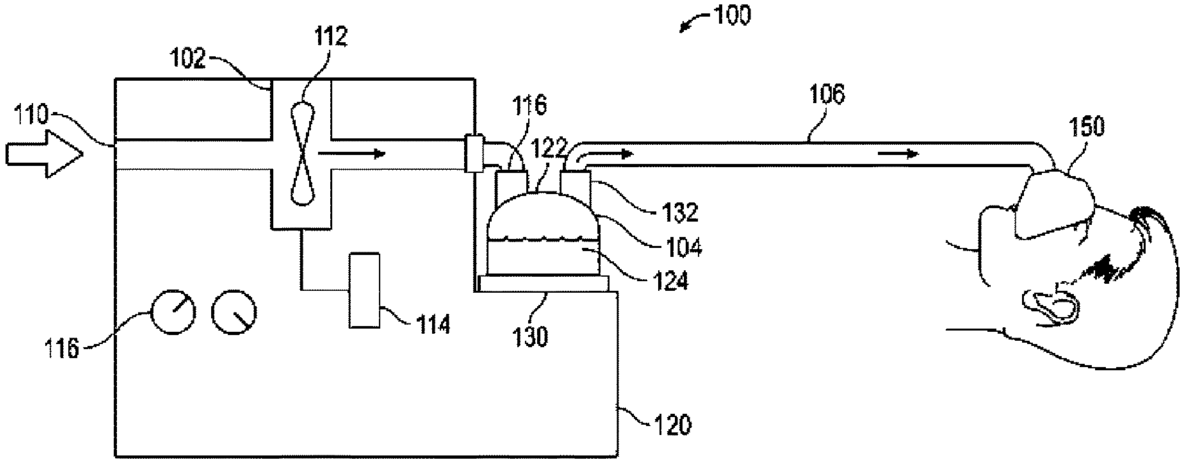
FIG. 1 is a schematic representation of a respiratory system configured to supply pressurized and humidified breathing gases to a user through a patient interface.

Embodiments of systems, components and methods of assembly and manufacture will now be described with reference to the accompanying Figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above," "below," "upper," "lower," "horizontal," "vertical" and the like refer to directions in the drawings to which reference is made. Terms such as "front," "back," "left," "right," "rear," "side," "forward" and "rearward" describe the orientation and/or location of portions of the components or elements within a consistent but arbitrary frame of reference which is made clear by reference to the text and the associated drawings describing the components or elements under discussion. Moreover, terms such as "first," "second," "third," and so on may be used to describe separate components. Such terminology may include the words specifically mentioned above, derivatives thereof, and words of similar import.

System Overview

FIG. 1 illustrates an example respiratory therapy system suitable for supplying breathing gases to a user for positive airway pressure (PAP) therapy (e.g., continuous positive airway pressure (CPAP) therapy) or non-invasive ventilation (NIV) therapy. The example respiratory therapy system 100 may include a gas source 102, a humidifier 104, a patient interface assembly 150 and a breathing gas circuit 106 that connects the humidifier 104 (or gas source 102) to the patient interface assembly 150. The gas source 102 can provide a supply of breathing gas to the humidifier 104. The gas source 102 may comprise a blower in which breathing gas, e.g., ambient air, is drawn into the gas source 102 through an inlet 110 in the gas source casing by an impeller 112. The rotational speed of the impeller 112 may be modulated to regulate the quantity of air drawn into the gas source 102 and the supply of breathing gas delivered to the respiratory therapy system 100. Breathing gas may include any single gas or multiple gases that are breathable by a user of the system 100.

The pressure and/or flow rate of breathing gas exiting the gas source 102 may be regulated by a controller 114. The controller 114 may modulate the rotational speed of the impeller 112 according to one or more predetermined algorithms and in accordance with one or more user inputs that may be provided via a user input 116.

The gas source 102 represents an actively controlled flow generator. Other gas sources, such as a compressed air cylinder with suitable pressure or flow regulation, may also be used to supply breathing gas. The outlet of the gas source 102 may be coupled to a separate humidifier 104. The humidifier 104 may be configured to heat and/or humidify the breathing gas prior to delivery, e.g., delivery to the user. In some embodiments, the humidifier is integrated with the gas supply. The humidifier 104 may include a base 120 and a humidifier chamber 122. The chamber 122 may be configured to hold humidification fluid 124, such as water, and may be disengaged, e.g., temporarily disengaged or permanently disengaged, from the humidifier base 120 to allow it to be filled or replaced. The humidifier 104 receives gases from the gas source 102 through chamber inlet 126. The humidifier base 120 can include a heater such as a heater plate 130. The chamber 122 rests on the heater plate 130 when engaged with the humidifier base 120. The heater plate 130 dissipates heat, e.g., heat generated by electrical resistance, to the chamber 122. The chamber 122 preferably has a heat conductive base to enable the heat generated by the heater plate 130 to pass efficiently to the humidification fluid 124. Controller 114 can also control the humidifier 104, and in particular the supply of electrical energy to the heater plate 130, to regulate any function of the humidifier 104, e.g., the temperature and humidity of the breathing gas supplied to the user.

The breathing gas can be supplied to the user via a chamber outlet 132 and the breathing gas circuit 106 in the form of a conduit which may incorporate a heating or warming element, e.g., a heater wire, to heat or warm (e.g., keep hot or warm) the breathing gases during transportation to the patient interface assembly 150. The electrical energy supplied to the heater wire may be controlled by the controller 114. The controller 114 may receive feedback from one or more sensors incorporated in a control network throughout the respiratory therapy system to monitor properties of the breathing gas, such as, but not limited to, pressure, flow, temperature, and/or humidity.

The patient interface assembly 150 couples the user with the respiratory therapy system 100, such that gases, e.g., heated and humidified gases from the humidifier 104, may be delivered to the user's respiratory system. Breathing gases can be delivered to the user at, or near, optimal temperature and humidity (e.g., warmed and fully saturated with water vapor at temperatures of between 27 and 37° C.) as the gases are delivered to the user's nares and or mouth. Emulating the conditions within healthy adult lungs (37° C., 44 mg/L humidity) can help maintain healthy mucocilliary function in users with respiratory disorders affecting secretion and for all patients humidifying the gas helps maintain comfort and compliance. A number of different styles of patient interface assembly 150, such as those disclosed herein, may be used in the example system 100 or a similar system.

Interface Assembly Overview

Figure 2:
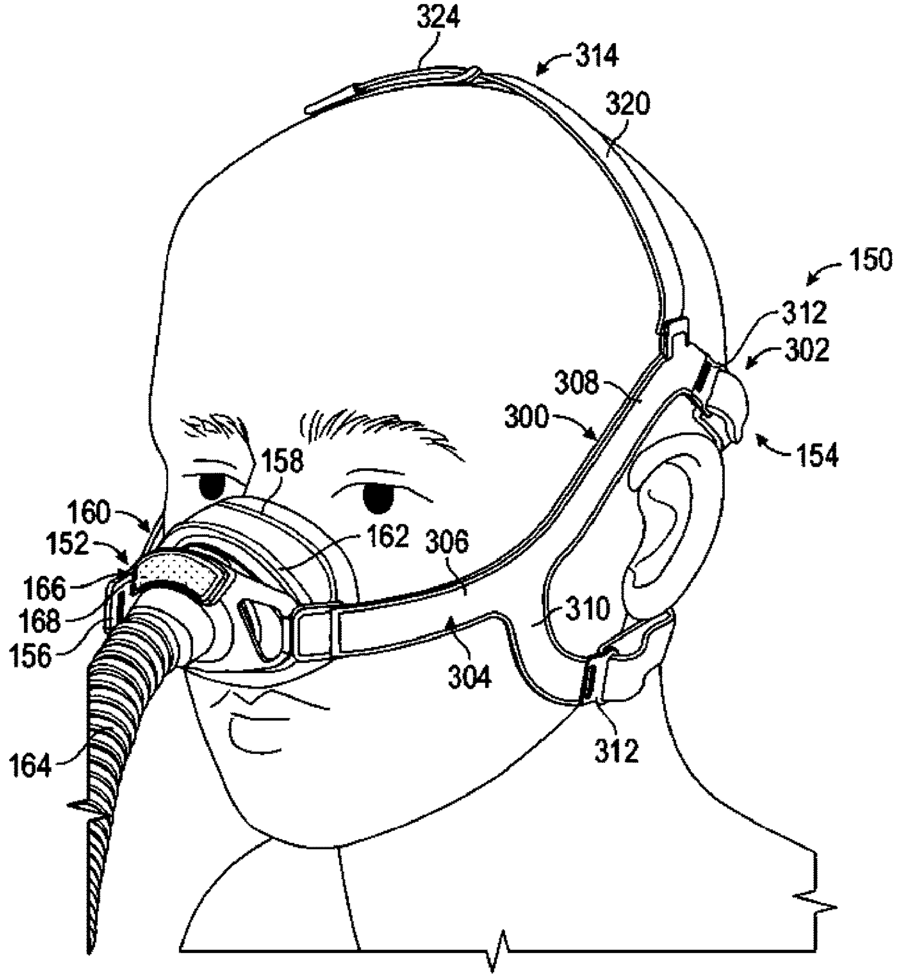
FIG. 2 is a perspective view of a patient interface assembly positioned on a user. The patient interface assembly includes an interface in the form of a nasal mask and a headgear arrangement.

FIG. 2 illustrates an example patient interface assembly 150 that can be used in the system 100 of FIG. 1. The patient interface assembly 150 generally includes an interface (e.g., a mask) 152 and a headgear arrangement ("headgear") 154. The interface 152 is configured to deliver the flow of breathing gases to an airway of the user. The headgear 154 is configured to secure the interface 152 in place on the user.

The illustrated interface 152 is a mask, which can define a breathing chamber. In particular, the illustrated interface 152 is a nasal mask that creates a seal on the user's face surrounding one or both nares. However, other suitable interfaces could also be used with the headgear 154 and/or the headgear 154 could be modified for use with different types of interfaces. For example, the interface could be a direct nasal mask having nasal elements (e.g., nasal pillows) configured to deliver the flow of breathing gases directly to the nares of the user. It will also be appreciated that various features, aspects and advantages of the patient interface assembly 150, while being described in the context of a nasal mask 152, can be used with any other interface configuration, including oronasal masks and full face masks sealing around the user's nose and mouth, oral masks sealing around the user's mouth, nasal pillows or other types of masks sealing under the user's nose, for example but without limitation.

The mask 152 can include a frame 156 and a cushion or seal 158. The cushion or seal 158 can be directly coupled to the frame 156 or can form a portion of a cushion module 160 that is connectable to the frame 156. Such a cushion module 160 can include a relatively rigid housing 162 that is constructed from a material(s) that is harder than the material of the cushion 158. The relatively rigid housing 162 can interface with the frame 156. The relatively rigid housing 162 may be removably connected to the frame 156. The relatively rigid housing 162 may incorporate a clip portion that engages with a portion of the frame 156 to connect the cushion module 160 to the frame 156.

The mask 152 can also include a connection tube 164 configured to connect the mask 152 to a breathing conduit (e.g., the breathing gas circuit 106). The connection tube 164 can be carried by any suitable portion of the mask 152, such as the frame 156 or the cushion module 160 (e.g., the housing 162). In the illustrated configuration, the connection tube 164 is directly connected to a cooperating portion of the mask 152 (e.g., the frame 156 or cushion module 160). The connection tube 164 may be permanently or removably connected to the cooperating portion of the mask 152. In other configurations, the mask 152 can be connected to a breathing conduit by a connector, which can be or comprises an elbow.

Figure 10:
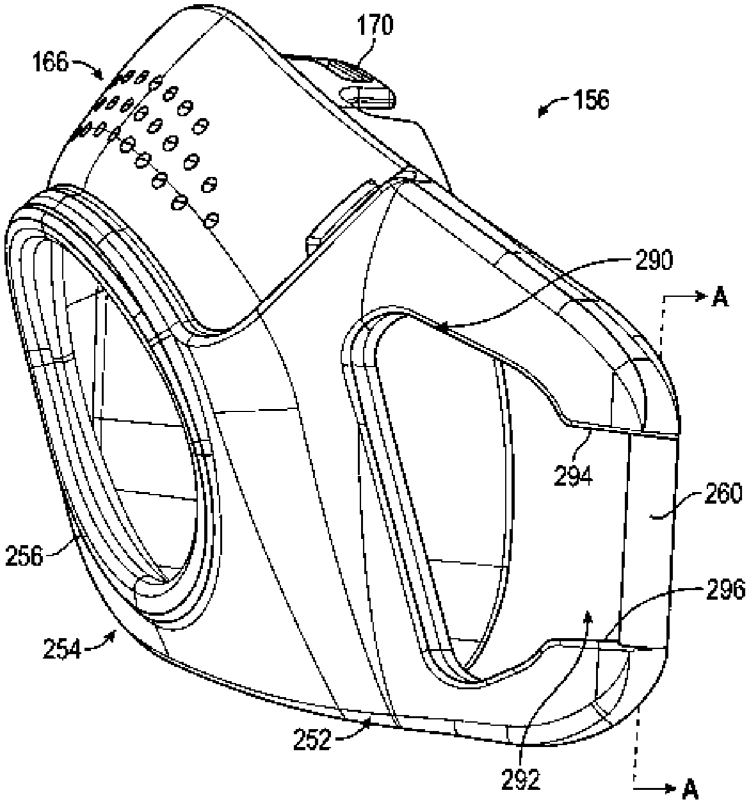
FIG. 10 is a perspective view of a frame of the nasal mask of FIG. 2 showing an opening and a post to which the clip of FIG. 9 can be connected.

The mask 152 can also include an exhaust or vent to permit expired and excess breathing gases to exit the breathing chamber of the mask 152. In some configurations, the vent can be a bias flow vent 166 comprising a plurality of vent holes (FIG. 10). In the illustrated arrangement, the bias flow vent 166 is located on the mask frame 156. In other configurations, the bias flow vent 166 could be located on other portions of the mask 152, such as the cushion module 160 or connection tube 164. In some configurations, as shown in FIG. 2, the bias flow vent 166 can include a diffuser 168 that covers the plurality of vent holes. The diffuser 168 can be removable from the mask 152 for cleaning or replacement. In some configurations, the diffuser 168 is permanently attached to a portion of the mask 152 by an overmolding process that positions a diffuser material into a mold and then injects a suitable plastic material (e.g., polycarbonate) into the mold to create a unitary structure. The diffuser material may be overmolded directly with the frame 156. In other embodiments, the diffuser material may be overmolded with a clip. The clip has engagement portions for engaging complementary engagement features on another part of the mask 152 in order to attach the clip (and the associated diffuser material) to that part of the mask 152.

Figure 48:
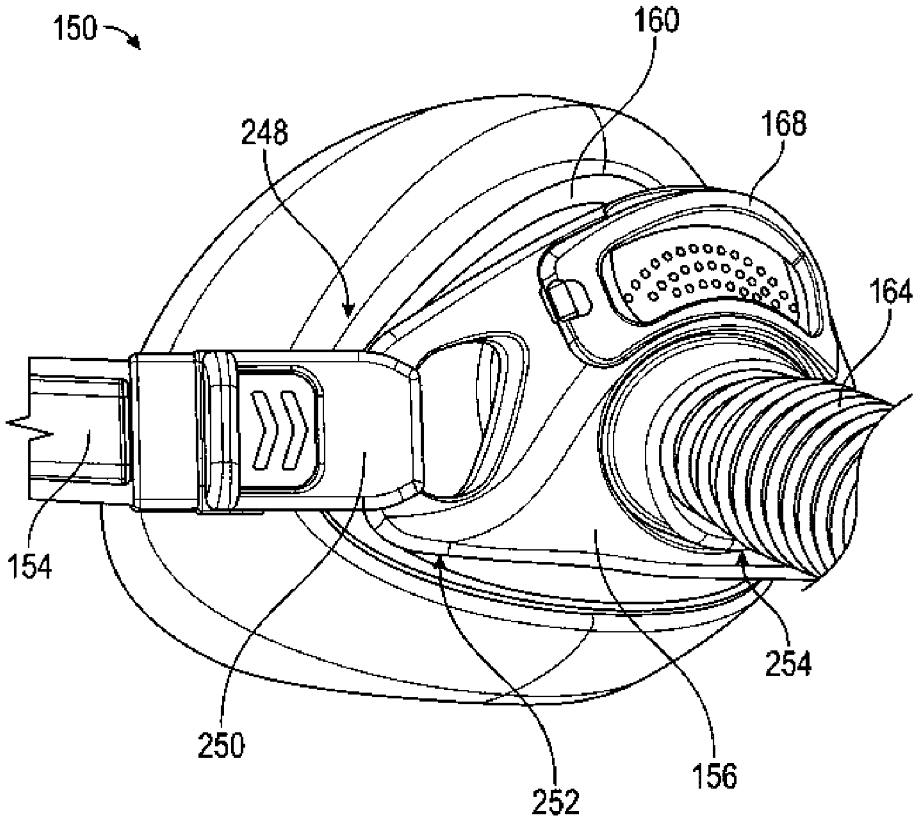
FIG. 48 is a perspective view of a modified version of the patient interface assembly of FIG. 2.
Figure 49:
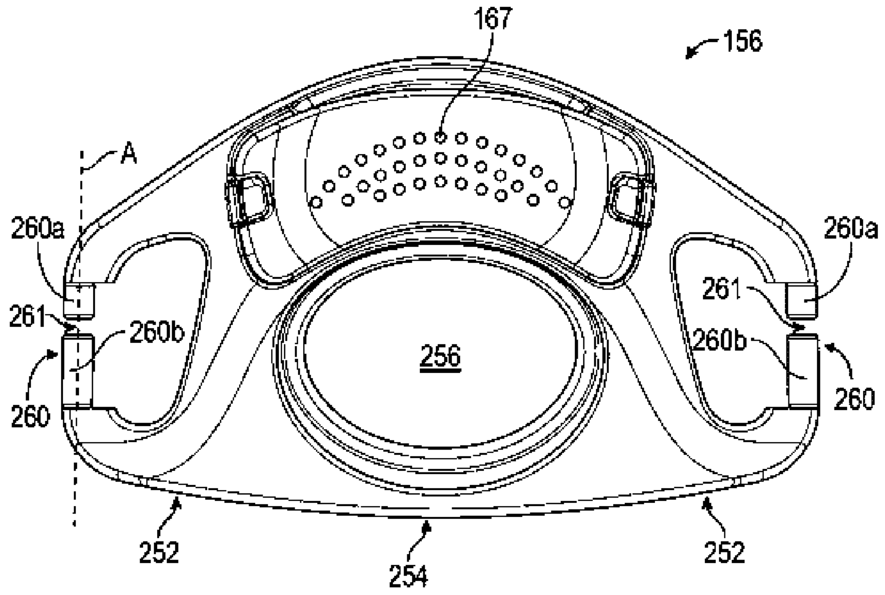
FIG. 49 is a front view of a frame of the patient interface assembly of FIG. 48.
Figure 50:
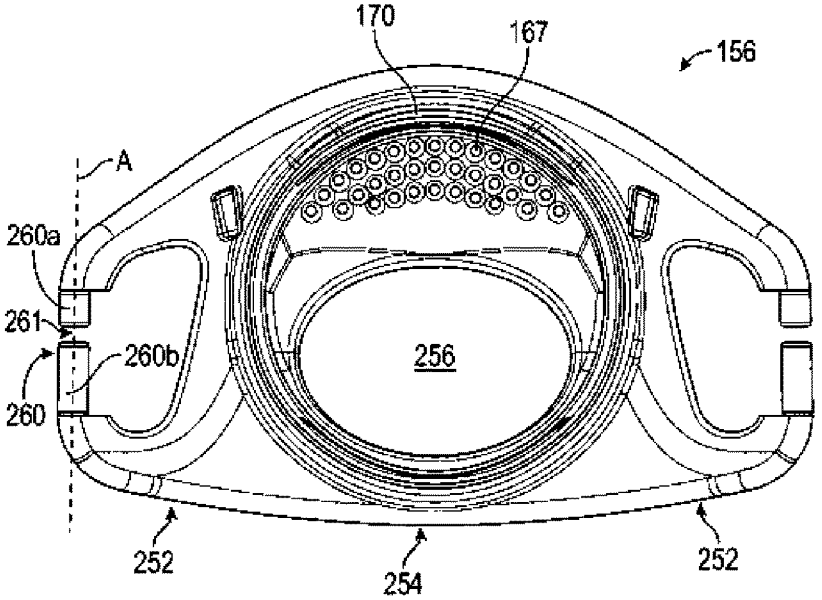
FIG. 50 is a rear view of a frame of the patient interface assembly of FIG. 49.

An alternative bias flow vent 166 and diffuser 168 is shown in the modified version of the patient interface assembly illustrated in FIGS. 48-50. The diffuser material is omitted from diffuser 168 in FIG. 48 for illustrative purposes. The bias flow vent 166 includes a plurality of vent holes 167. The vent holes 167 are provided within a recessed portion 157 of the frame 156. The recessed portion 157 is wider than the opening 256. A depression in the wall of the frame 156 immediately above the recessed portion 157 provides an opening to assist in removal of the diffuser clip 168 from the frame 156. In use, the recessed portion 157 may be concealed by the diffuser 168. The diffuser 168 is wider than the opening 256. The vent holes 167 are arranged in three arcuate rows above the opening 256. The vent holes 167 span a width approximately equal to the width of the opening 256. A radius of curvature of the first row, nearest the opening 256, is shorter than the second and third rows. A radius of curvature of the third row, furthest from the opening 256, is longer than the first and second rows. The number of vent holes 167 in the first row is less than the number of vent holes 167 in the second and third rows. The number of vent holes 167 in the third row is greater than the number of vent holes 167 in the first and second rows. The end-most vent holes 167 in the three rows are approximately aligned in the vertical direction. The vent holes 167 may vary in diameter along their length. In particular, the vent holes 167 converge in the direction of bias flow (that is, from the interior to the exterior of the patient interface assembly 150). The converging vent holes 167 may reduce noise from venting gases.

Referring again to FIG. 2, the headgear 154 is coupled to the mask 152. The headgear 154 can be coupled to the frame 156 of the mask 152. The frame 156 or mask 152 preferably includes a single headgear mount on each side of the frame 156 or mask 152. In the illustrated arrangement, the headgear 154 includes a headgear strap provided on each side of the user's head, which bifurcates at a location along the user's face (e.g., cheek) between the mask 152 and the user's ear. The straps on each side can be separate from one another or can form a unitary strap that extends from one side of the user's head to the other side and has an intermediate portion that connects to the frame 156 or mask 152. The headgear 154 can also include a rear portion and an optional top portion, which are described further below in additional detail.

Interface

With continued reference to FIG. 2 and additional reference to FIG. 10, the cushion module 160 can be selectively connected to and disconnected from the frame 156 of the mask 152. The frame 156 and the cushion module 160 preferably connect together in a substantially airtight or sealed relationship. For example, the frame 156 can comprise a connector 170 in the form of a mounting boss, connection ring or collar that extends in a rearward direction from the frame 156 toward the user or the cushion module 160. The frame connector 170 supports the housing 162 of the cushion module 160. The frame connector 170 has inner and outer surfaces. The housing 162 engages an outer surface of the collar 170 in the illustrated arrangement. However, in an alternative arrangement, the housing 162 could engage an inner surface of the frame connector 170. The connector 170 encircles the opening 256 and the bias flow vent 166.

The mask 152 can incorporate an arrangement that reduces the likelihood of unintentional or undesired separation of the frame 156 and the cushion module 160. For example, the mask 152 can include an interference or interlocking (e.g., snap fit) arrangement 320 that assists in maintaining the connection between the frame 156 and the cushion module 160 and/or increases the force required to separate the frame 156 and the cushion module 160. One such arrangement includes at least one protrusion on one of the frame 156 and the cushion module 160 and at least one recess sized and shaped to accommodate the protrusion on the other of the frame 156 and the cushion module 160. Other suitable arrangements, such as a friction member and cooperating surface could also be used.

The frame connector 170 and a cooperating opening of the housing 162 can have a non-circular or non-cylindrical shape to rotationally fix the frame connector 170 and the housing 162 about an axis of the frame connector 170. Other arrangements to prevent rotation between the frame 156 and the cushion module 160 could be used in the alternative or in addition. For example, as shown in the modified version of the patient interface assembly in FIGS. 45-47, a cylindrical collar could be used along with interference structures that inhibit or prevent rotation or misalignment that would otherwise be permitted by the cylindrical shape of the collar. The frame 156 and cushion module 160 preferably may be attached to each other in only a single orientation. In some configurations, however, the frame 156 and cushion module 160 may be configured to be selectively attached to each other in two or more predetermined orientations. For example, a user may rotate the frame 156 by 1800 with respect to the cushion module before attachment to selectively orient the bias flow vent either above or below the opening of the housing 162. The interference structures may be tapered to correct small misalignments as the frame and cushion module are brought together.

Cushion Module

As described above, the illustrated cushion module 160 includes a relatively rigid housing 162 that is constructed from a material(s) that is harder than the material of the cushion 158. In some configurations, the housing 162 is constructed in part or in whole from a polycarbonate or similar material. Accordingly, the cushion 158 can be constructed from a material(s) that is softer than the material of the relatively rigid housing 162, such as silicone or a similar material. Unless indicated otherwise, descriptions of relative rigidity or stiffness of materials herein refer to differences in the modulus of elasticity between the materials or differences in rigidity or stiffness of solid bodies of the same size and shape constructed from the materials being compared. Descriptions of relative rigidity or stiffness of particular structures can refer to resistance to deformation of those structures, taking into account both material properties and physical characteristics of the structures (e.g., size, shape, wall thickness).

In some configurations, the cushion 158 can be removably connected to the housing 162 (or directly to the frame 156). However, in the illustrated arrangement, the cushion 158 is permanently connected to the housing 162. To permanently attach the cushion 158 to the housing 162, a molding process, such as co-molding or over-molding, can be used. In addition, a retention structure, such as a mechanical interlock, can be used to positively lock and thereby enhance the connection between the silicone material of the cushion 158 and the polycarbonate material of the housing 162. The retention structure can comprise a plurality of openings defined by the housing 162 that are occupied by the material of the cushion 158. The retention structure could alternatively or additionally include an annular lip positioned along or adjacent to an edge of the housing 162 that is surrounded by and creates a keyed engagement with the material of the cushion 158.

Mask Cushion

The cushion 158 can be an inflation-type seal having an interior-concave curved wall that inflates when the interior of the mask 152 is pressurized to provide a good seal and better conform to the face of the particular user. As such, the pressure contained within the cushion 158 can urge a face contacting portion against the face of the user. However, other types of seals can be used, if desired.

With reference to FIGS. 3-7, the illustrated cushion 158 includes a rim 180 that defines an opening 182 through which breathing gases are introduced into an interior of the cushion 158. The housing 162 can be connected to the cushion 158 at the rim 158. The rim 180 can have a larger thickness than other portions of the cushion 158.

The cushion 158 includes an end wall 184 that defines a face contacting surface 186 configured to contact a face of the user in use. The end wall 184 is located opposite the rim 180. A side wall 188 extends between the rim 180 and the end wall 184. The end wall 184 extends inwardly from the side wall 188. That is, portions of the end wall 184 on opposite sides of the cushion 158 extend towards each other from the side wall 188. The end wall 184 includes an edge 190 that at least partially defines an opening 192. In the illustrated configuration, the edge 190 surrounds the opening 192. In some configurations, the cushion 158 tapers or reduces in thickness in a direction toward or to the edge 190. That is, preferably, the cushion 158 does not include a thickened rim or bead at or adjacent the edge 190. In some configurations, the end wall 184 may include a thickened rim or bead 191 at or adjacent the edge 190, as shown in the modified version of cushion 158 in FIGS. 37 and 40. The thickened rim or bead 191 may ameliorate noise generated by flapping of the end wall 158 in the event of a leak, and/or may reduce the risk of tearing of the cushion 158 from the opening 192. The thickened rim or bead 191 may have a radius of between about 0.1 and 0.4 mm, preferably between about 0.2 and 0.3 mm, and preferably about 0.26 mm. The opening 192 is designed to accommodate at least the lower portion and tip of a nose of the user. Preferably, the opening 192 is generally T-shaped, albeit an inverted T-shape.

Figure 5:
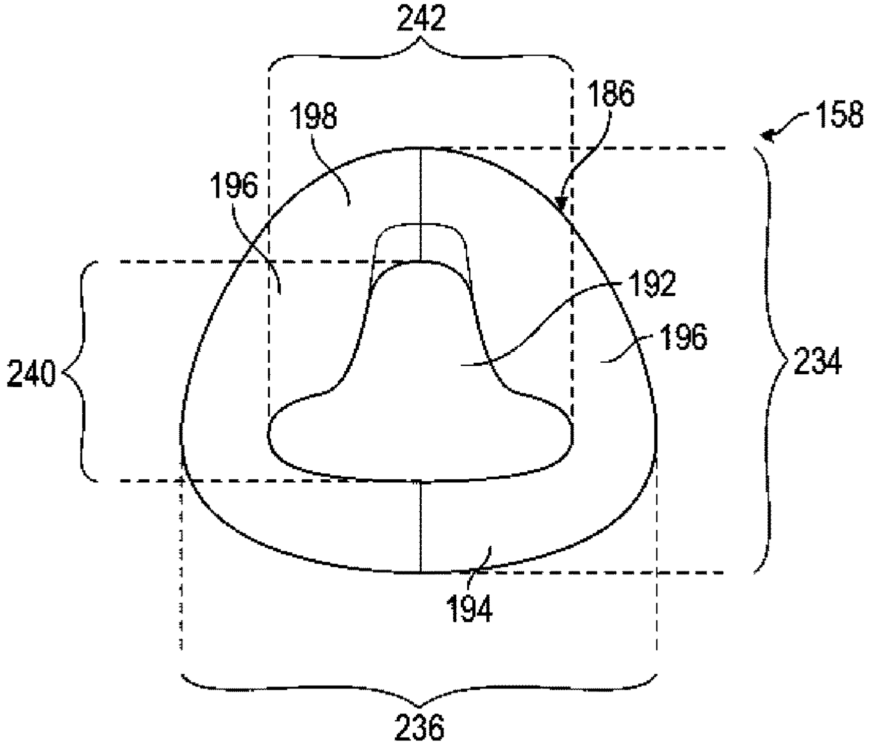
FIG. 5 is a rear view of the cushion of the nasal mask of FIG. 2 showing a face contacting surface.

With reference to FIG. 5, the face contacting surface 186 generally comprises a lower or lip surface 194, which is adapted to contact the face of the user at a location above the vermillion border and below the nares. The face contacting surface 186 also comprises two separate cheek surfaces 196, which extend between the lip surface 194 of the face contacting surface 186 and an upper surface 198 on each side of the face contacting surface 186. The cheek surfaces 196 can contact the medial cheek surface of the user and/or the lateral nose surface of the user. The upper surface 198 can extend over the nose of the user to connect the two cheek surfaces 196.

The end wall 184 can be the thinnest or among the thinnest portions of the seal cushion 158. Advantageously, the end wall 184 can easily deform to at least substantially seal against the facial contours of the user, including one or more of the upper lip, the medial cheek, the lateral nose and the bridge of the nose. Advantageously, the small wall thickness of the end wall 184 within the lip surface 194 allows for increased stretchability and results in minimal pressure being applied to the region above the lips of the user.

Figure 3:
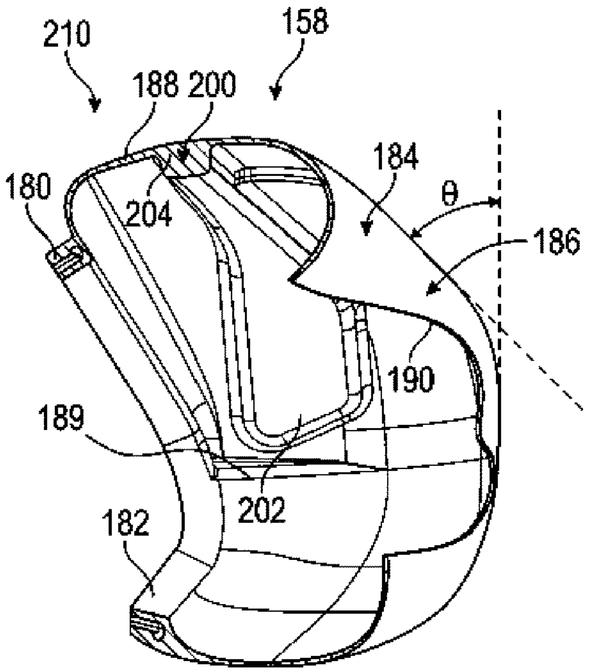
FIG. 3 is a sectional view of a seal or cushion of the nasal mask of FIG. 2 taken along a central, vertical plane that bisects the cushion into a right side and a left side.
Figure 4:
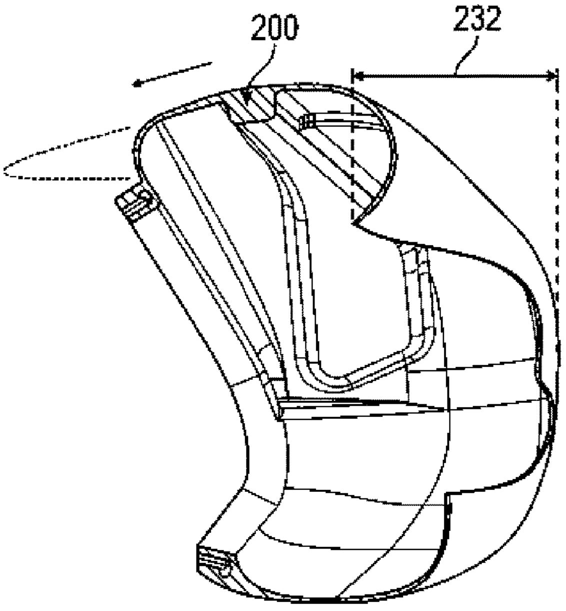
FIG. 4 is a sectional view of the cushion of the nasal mask of FIG. 2 taken along the central, vertical plane and illustrating movement permitted by a rolling bridge feature.

With reference to FIGS. 3 and 4, a reinforcement in the form of at least one thickened band 200 extends inwardly from an interior surface of the cushion 158. While a single thickened band 200 is shown in FIGS. 3 and 4, in some configurations, two or more thickened bands or thickened regions can be provided keeping in mind a desire to achieve the characteristics provided by the thickened band 200.

The illustrated thickened band 200 is positioned along the side wall 188 of the cushion 158. The band 200 preferably comprises a larger lower region 202 on each lateral side of the cushion 158 and a thinner connecting portion 204 that extends between the lower regions 202 by extending around the upper portion of the inside of the cushion 158. When the cushion 158 receives pressure from the gas source 102 (FIG. 1), the thickened band 200 helps to reduce the likelihood of, and/or the degree of, outward ballooning of the side wall 188. Outward ballooning of the side wall 188 can cause undesired changes in a shape of the cushion 158, which can adversely impact performance and lead to undesirable leaking from the cushion 158.

The cushion 158 can define a region of reduced stiffness 210 between the thickened band 200 and the rim 180. The region of reduced stiffness 210 can permit preferential forward movement of an upper portion of the cushion 158 to allow the cushion 158 to adapt to a range of user nasal features and sizes. The upper portion of the cushion 158 can be configured to pivot or hinge relative to a lower portion of the cushion 158 about a hinge axis or hinge region to allow pivotal movement of the upper portion of the cushion 158 in a forward direction (a direction away from the face of the user or toward the housing 162). The hinge axis or hinge region may be defined, in part, by the thickened band 200, and is preferably positioned just below the lower regions 202. The hinge axis may also be defined, in part, by a lower thickened corner 189 at or adjacent the respective lower corners of side wall 188. The side wall 188 tapers over a relatively short distance from the lower thickened corner 189 upwardly towards the lower region 202 of band 200. The side wall 188 also tapers over a relatively longer distance downwardly from the lower thickened corner 189.

In the illustrated arrangement, the region of reduced stiffness 210 is configured to roll in response to the pivotal movement of the upper portion 154. As illustrated schematically by the dashed lines in FIG. 4, the region of reduced stiffness 210 is designed to roll toward the front of the mask 152 (i.e., in a direction away from the user). Accordingly, the region of reduced stiffness 210 can be referred to herein as a rolling portion or a rolling bridge. In the rolling bridge 210, an inflection point between a first or upper portion and a second or lower portion of the rolling bridge 210 moves along the rolling bridge 210 and lengths of the upper portion and the lower portion vary during the rolling movement. In some configurations, the rolling bridge 210 rolls over and/or onto an outer surface of the mask 152, which can be a portion of the cushion 158 and/or the housing 162. The rolling bridge 210 may provide one or more of the benefits of predictable deformation of the cushion 158 without buckling or the need for predefined concertina-type folds, adaptation of the cushion 158 to a wide range of facial and nasal dimensions, limiting a sealing force upon the patient's nose, and/or at least partially decoupling the sealing force upon the patient's nose from a headgear tension force and/or tube drag forces.

Figure 7:
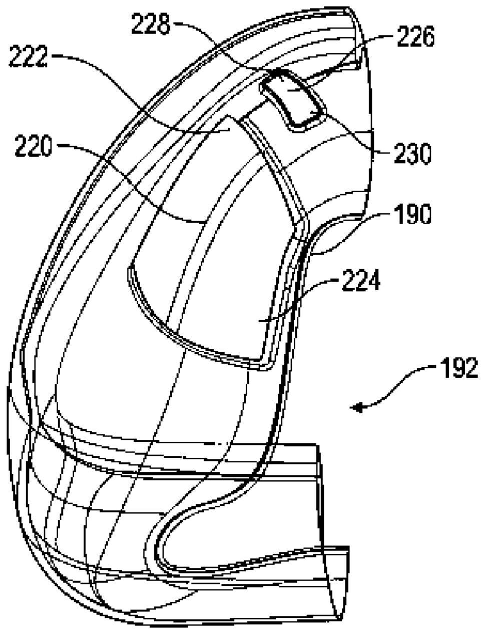
FIG. 7 is a perspective view of a portion of the cushion of FIG. 5 showing features of an interior surface of the cushion.

With reference to FIGS. 3, 4 and 7, the illustrated cushion 158 also comprises two thickened panels 220. The thickened panels 220 are positioned along upper portions of the cheek surfaces 196 of the cushion 158, close to a transition from the cheek surfaces 196 to the upper surface 198. The panels 220 can be formed on an interior surface of the cushion 158. The illustrated panels 220 represent locally thickened regions that have been found to enhance the sealing capability of the cushion 158. The panels 220 increase a lateral pressure against the lateral nose surface of the user, which allows pressure from the cushion 158 to better contour to the shape of the nose of the user. In the illustrated arrangement, a thickness of the panels 220 is less than a thickness of the thickened band 200. In some configurations, the thickness of the panels 220 is less than about one-half or less than about one-quarter of the thickness of the thickened band 200. In some configurations, the panels 220 may be between 1.0 and 1.5 mm thick. In some configurations, the panels 220 are between about 1.2 and 1.3 mm thick. In some configurations, the panels 220 are about 1.25 mm thick. In some configurations, portions of the side wall 188 including the panels 220 may be thicker than adjacent portions of the side wall 188 by between about 0.8 and 1.2 mm. In some configurations, the portions of the side wall 188 including panels 220 are thicker by between about 0.9 and 1.1 mm. In some configurations, the portions of the side wall 188 including panels 220 are thicker by about 1 mm.

In the illustrated arrangement, each of the panels 220 extend from the thickened band 200 or have a side or a portion of a boundary that is immediately adjacent the thickened band 200. The illustrated panels 220 each are generally rectangular in shape. Each of the thickened panels 220 extend from the thickened band 200 along the side wall 188 and the end wall 184. One end (e.g., a forward end 222) of each of the rectangular panels 220 is connected to or immediately adjacent to the thickened band 200. In the illustrated arrangement, each of the thickened panels 220 extends onto the end wall 184. Each of the panels 220 has a rearward end 224 that terminates prior to the edge 190 of the opening 192. In other words, the rearward end 224 of each of the thickened panels 220 is spaced from the edge 190.

Figure 37:
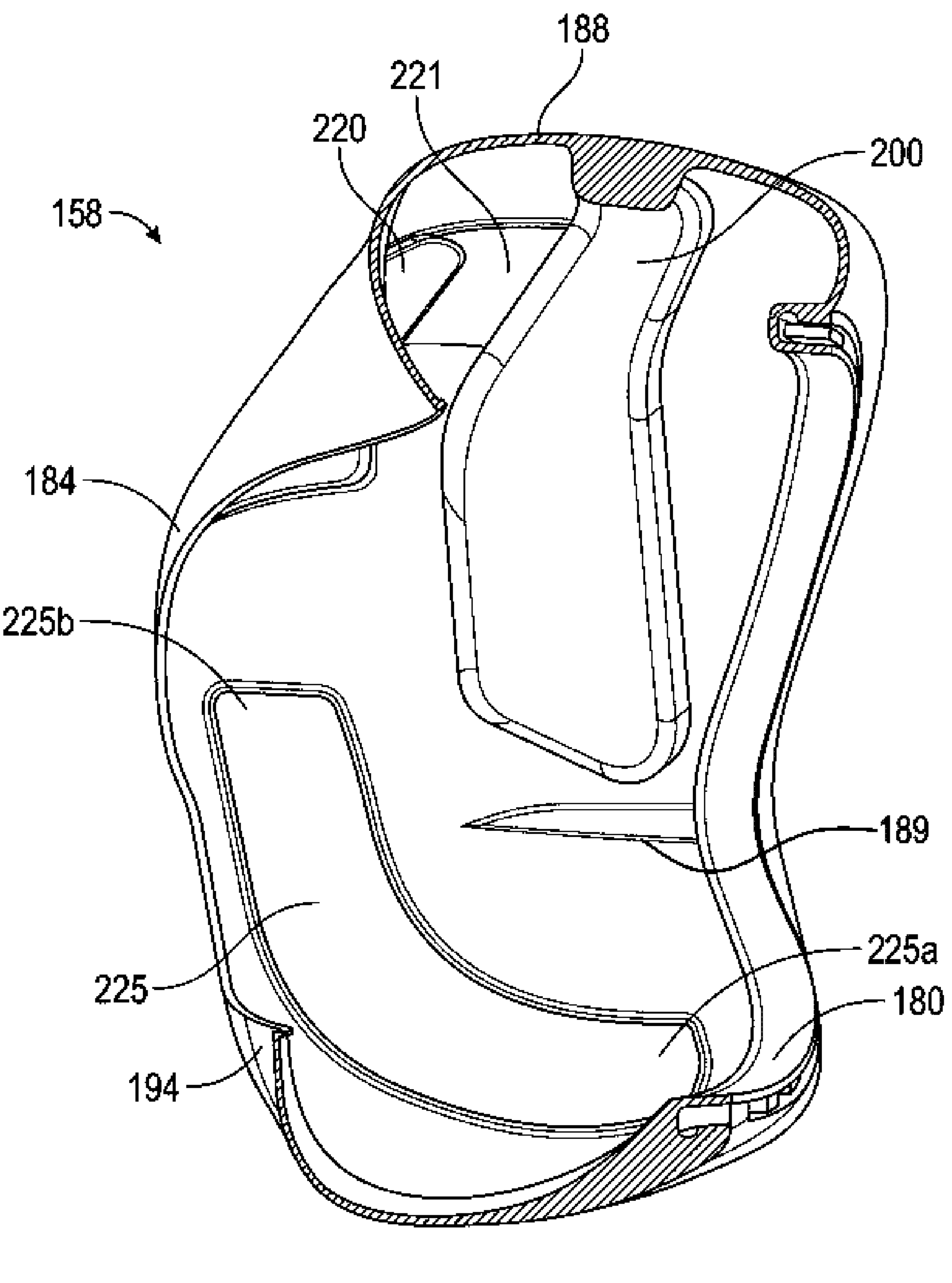
FIG. 37 is a sectional view of a seal or cushion of another configuration, taken along a central, vertical plane that bisects the cushion into a right side and a left side.

In some configurations, as shown in FIG. 37 for example, the thickened panels 220 may be spaced from the thickened band 200, and the cushion 158 can include a joining pad 221 intermediate a portion of the thickened band 200 and at least a portion of the thickened panel 220. The joining pad 221 in the illustrated configuration comprises a generally-rectangular thickened region of the side wall 188 which joins an upper portion of the thickened panel 220 to the thickened band 200. A lower portion of the thickened panel 220 remains spaced apart from the thickened band 200. The joining pad 221 preferably provides support to the side wall 188 of the cushion 158 to reduce deformation and mitigate leaks in selected regions of the cushion 158, particular around the patient's eyes, without causing breathing restrictions. The joining pad 221 has a thickness which is less than that of the thickened panel 220, but greater than that of the other adjacent portions of side wall 188. In some configurations, the portions of the side wall including joining pads 221 may be thicker than the adjacent portions of the side wall 188 by between about 0.5 and 0.9 mm. In some configurations, the portions of the side wall including the joining pad 221 may be thicker by between about 0.65 and 0.75 mm. In some configurations, the portions of the side wall including the joining pad 221 may be thinner than the adjacent thickened panel 220 by between about 0.2 and 0.4 mm. In some configurations, the portions of the side wall including the joining pad 221 may be thinner by about 0.25 and 0.35 mm. The joining pad 221 has a width measured in the forward direction from the thickened panel 220 to the thickened band 200 which spaces at least a portion of the thickened panel 220 from the thickened band 200 by a corresponding distance. In some configurations, a width of at least a portion of the joining pad 221 is between about 3 and 4 mm. In some configurations, the width may be around 3.2-3.6 mm. In some configurations, the width may be around 3.4 mm. The joining pad 221 is preferably provided only towards an upper end of the thickened panel 220, which may allow for relatively more deformation of the side wall 188 towards a lower end of the thickened panel 220 so that there is less pressure on more sensitive areas of the patient's face. The joining pad 221 has a length extending in the circumferential direction around the inside of the cushion 158. In some configurations, the length of the joining pad 221 is between about 15% and 50% of the length of the of the adjacent thickened panel 220. In some configurations, the length is between about 20% and 45% of the length of the adjacent thickened panel 220. In some configurations, the length is between about 25% and 33% of the length of the adjacent thickened panel 220.

With reference to FIG. 7, the cushion 158 can include one or more thickened panels 226 in addition to or in the alternative to the thickened panels 220. For convenience, the thickened panels 226 are referenced to herein as "secondary" thickened panels 226. In the illustrated arrangement, a pair of secondary thickened panels 226 are provided. Both of the pair of secondary thickened panels 226 are located between the thickened panels 220 toward or within an upper portion of the cushion 158. Each of the illustrated secondary thickened panels 226 is substantially smaller than the thickened panels 220. The secondary thickened panels 226 can be generally rectangular in shape and can have a forward end 228 that is connected or immediately adjacent to the thickened band 200. Each of the secondary thickened panels 226 can have a rearward end 230 that is spaced from the edge 190 of the opening 192. In some configurations, the secondary thickened panels 226 have a surface area that is between about one-tenth to one-twentieth of the surface area of the thickened panels 220.

In some configurations, the face contacting surface 186 is non-planar. For example, the face contacting surface 186 in an upper portion of the cushion 158 can extend in a forward direction relative to a middle portion and/or lower portion of the cushion 158. A portion or an entirety of the upper surface 198 of the face contacting surface 186 can be located forward of a portion or an entirety of the cheek surfaces 196 and/or the lip surface 194. In some configurations, the upper surface 198 can define an angle θ with respect to a middle portion of the cushion 158 or the cheek surfaces 196 of the cushion 158. In some configurations, a rearward-most edge of the upper surface 198 can define the angle θ with respect to a rearward-most edge of a middle portion of the cushion

158. The middle portion of the cushion 158 is located above the upper-lip-contacting portion. In some configurations, when viewed from the side with the cushion 158 in an upright orientation, a rearward-most edge of the upper surface 198 can define the angle θ with respect to the cheek surfaces 196 and/or a vertical direction, as shown in FIG. 3. In the upright orientation, the cheek surfaces 196 can lie in a generally or substantially vertical direction. The upright orientation can correspond with an in-use orientation of the cushion 158, which is an orientation of the cushion 158 as properly positioned on a user with the user's head in an upright orientation. The angle θ can be less than 55 degrees. In some configurations, the angle θ is between about 40-50 degrees or between about 42-48 degrees. In some configurations, the angle θ is about 45 degrees.

With reference to FIG. 4, the face contacting surface 186 of the cushion 158 can define a depth 232 of the opening 192 between a rearward-most point and a forward-most point of the opening 192. The rearward-most point can be located on the cheek surface 196. The forward-most point can be located on the upper surface 198. In particular, the forward-most point can be located on the edge 190 of the opening 192. The depth 232 of the face contacting surface 186 can be greater than 15 mm. In some configurations, the depth 232 is between about 16-25 mm or between about 18-22 mm. In some configurations, the depth 232 is about 20 mm or 20.5 mm.

With reference to FIG. 5, the cushion 158 can define a height 234 and a width 236. The height 234 and/or width 236 can be selected to achieve desirable sealing properties while reducing or minimizing the obtrusiveness of the cushion 158 and the mask 152 to the user. In particular, the height 234 can be selected so that the upper surface 198 contacts the dorsal hump of the user's nose. In some configurations, the height 234 can be between about 45 mm-60 mm or between about 47.8 mm-57.8 mm for a single cushion 158 or across the entire size range of the cushion 158. For example, the cushion 158 can be provided in at least three sizes, with a small size having a height 234 of about 47 mm to 48 mm (e.g., 47.8 mm), a medium size having a height 234 of about 52 mm to 53 mm (e.g., 52.8 mm), and a large size having a height 234 of about 57 mm to 58 mm (e.g., 57.8 mm). In some configurations, the width 236 can be between about 55 mm-64 mm or between about 56.5 mm-63.9 mm for a single cushion 158 or across the entire size range of the cushion 158. For example, the small size can have a width 236 of about 56 mm to 57 mm (e.g., 56.5 mm), the medium size can have a width 236 of about 58 mm to 59 mm (e.g., 58.3 mm), and the large size can have a width 236 of about 63 mm to 64 mm (e.g., 63.9 mm).

A ratio of the width 236 to the height 234 can be between about 1.1-1.2 for a single cushion 158 or across the entire size range of the cushion 158. For example, the ratio of the width 236 to the height 234 of a small size cushion 158 can be about 1.2 (e.g., 1.18). The ratio of the width 236 to the height 234 of a medium size cushion 158 can be about 1.1. The ratio of the width 236 to the height 234 of a large size cushion 158 can be about 1.1 (e.g., 1.12).

The opening 192 of the cushion 158 can define a height 240 and a width 242. The height 240 and/or width 242 can be selected to achieve desirable sealing properties of the cushion 158. In some configurations, the height 240 can be between about 20 mm-35 mm or between about 22.8 mm-32.5 mm for a single cushion 158 or across the entire size range of the cushion 158. For example, the small size can have a height 240 of about 22 mm to 23 mm (e.g., 22.8 mm), the medium size can have a height 240 of about 23 mm to 24 mm (e.g., 23.3 mm), and the large size can have a height 240 of about 32 mm to 33 mm (e.g., 32.5 mm). In some configurations, the width 242 can be between about 34 mm-45 mm or between about 34.2 mm-43.1 mm for a single cushion 158 or across the entire size range of the cushion 158. For example, the small size can have a width 242 of about 34 mm to 35 mm (e.g., 34.2 mm), the medium size can have a width 242 of about 37 mm to 38 mm (e.g., 37.4 mm), and the large size can have a width 242 of about 43 mm to 44 mm (e.g., 43.1 mm).

A ratio of the width 242 to the height 240 can be greater than 1.25. In some configurations, the ratio of the width 242 to the height 240 can be between about 1.25-1.7 or between about 1.3-1.65 (e.g., 1.33-1.61) for a single cushion 158 or across the entire size range of the cushion 158. For example, the ratio of the width 242 to the height 240 of a small size cushion 158 can be about 1.5. The ratio of the width 242 to the height 240 of a medium size cushion 158 can be about 1.6 (e.g., 1.61). The ratio of the width 242 to the height 240 of a large size cushion 158 can be about 1.3 (e.g., 1.33).

Figure 6:
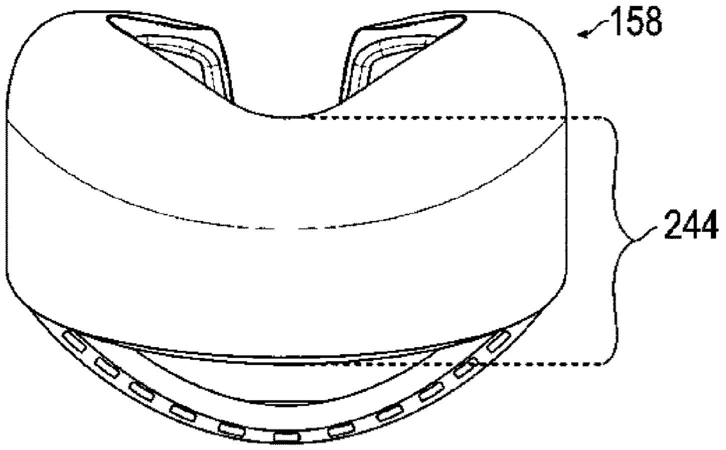
FIG. 6 is a bottom view of the cushion of FIG. 5.
Figures 1, 6:
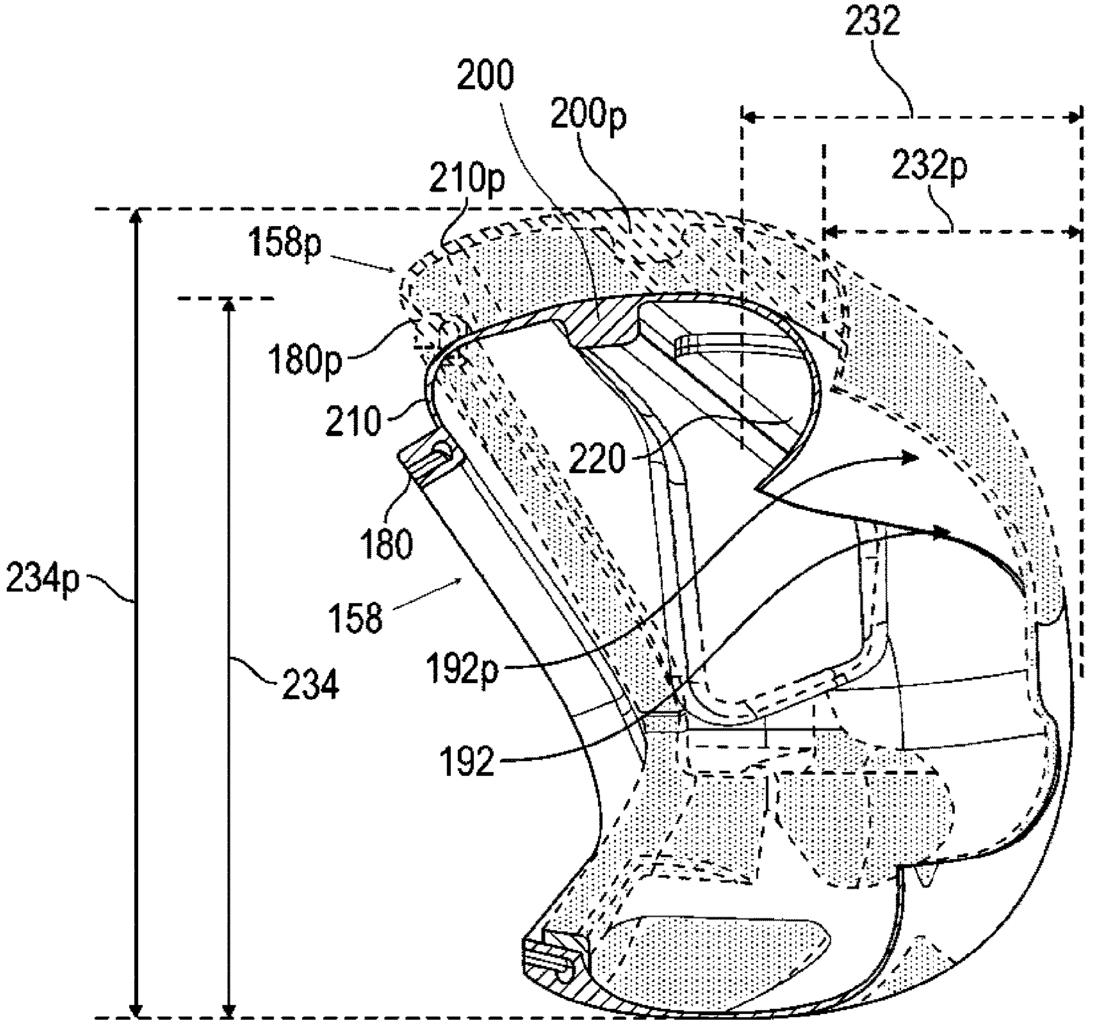
Figures 2, 6:
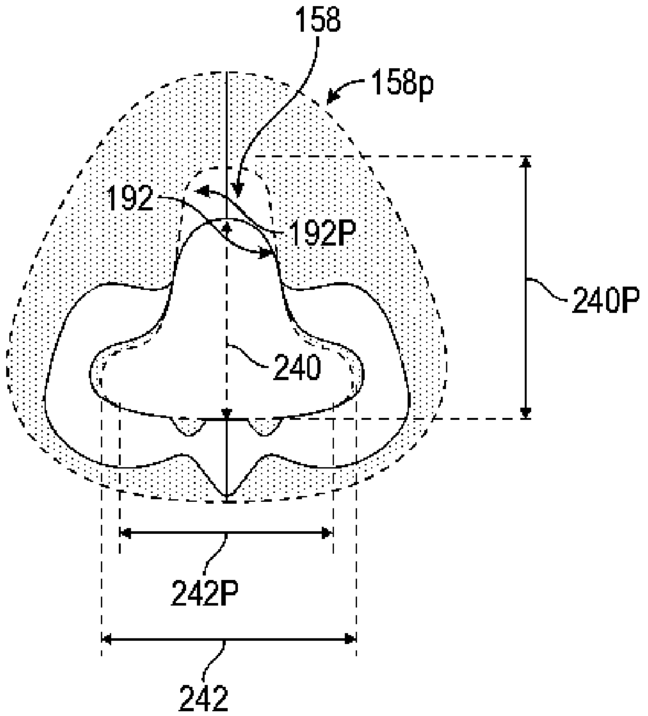

With reference to FIG. 6, the cushion 158 can define a depth 244 between a forward-most point and a rearward-most point along a section of the cushion 158. For example, the depth 244 can be measured along a vertical, center plane that bisects the cushion 158 into a right side and a left side. In some configurations, the depth 244 is measured at the lower portion of the cushion 158. For example, the depth 244 can be measured between a forward-most point on the rim 180 and a rearward-most point on the lip surface 194 that lie within the vertical, center plane. In some configurations, the depth 244 can be between about 20-30 mm, between about 23-28 mm, or between about 25-26 mm for a single cushion 158 or across the entire size range of the cushion 158. In some configurations, the depth 244 can be about 25.35 mm.

FIGS. 6-1 and 6-2 illustrate certain differences between the present cushion 158 and a prior art cushion 158P marketed by the Applicant, Fisher & Paykel Healthcare Ltd., as a component of the Eson 2 nasal mask. As illustrated in FIG. 6-1, the height 234 of the present cushion 158 is smaller than a height 234P of the Eson 2 cushion 158P. As a result, an upper portion of the present cushion 158 is located lower on the user's nose compared to the Eson 2 cushion 158P. Thus, a larger proportion of the cushion 158 can be located out of the user's field of vision and/or an upper portion of the cushion 158 can be located closer to an edge of the user's field of vision compared to the Eson 2 cushion 158P. Accordingly, the present cushion 158 is less obtrusive to the user than the Eson 2 cushion.

As also illustrated in FIG. 6-1, the depth 232 of the opening 192 of the present cushion 158 is larger than the depth 232P of the opening 192P of the Eson 2 cushion 158P. Such an arrangement can facilitate or accommodate the lower position of the present cushion 158 on the user's nose.

In some configurations, the rolling bridge 210 of the present cushion 158 can connect to the rim 180 at a location spaced away from the forward end of the rim 180. In other words, a portion of the rim 180 can protrude in a forward direction from the rolling bridge 210. In some configurations, the rolling bridge 210 can extend from a rearward end of the rim 180 such that an interior surface of the rim 180 is aligned with an interior surface of the rolling bridge 210 at a transition between the rim 180 and the rolling bridge 210. In contrast, the rolling bridge 210P of the Eson 2 cushion 158P connects to a forward end of the rim 180P. The arrangement of the present cushion 158 allows the mold tooling to be simpler and cheaper in comparison to the arrangement of the Eson 2 cushion 158P. In other configurations, however, the rolling bridge 210 can connect to a forward end of the rim 180, as illustrated in the modified form of cushion 158 shown in FIG. 38.

As described above and illustrated in FIGS. 6-1 and 7, the thickened panels 220 of the present cushion 158 extend into or connect to the thickened band 200. In contrast, forward ends of the thickened panels (not shown) of the Eson 2 cushion 158P terminate well short of the thickened band 200P. In some configurations, rearward ends of the thickened panels 220 of the present cushion 158 and the Eson 2 cushion 158P are in the same or a similar relative position on the cushion 158, 158P. The longer thickened panels 220 of the present cushion 158 improve the localized strength or stiffness of the cushion 158 for a better seal to reduce leaks.

With reference to FIG. 6-2, the opening 192 of the present cushion 158 is shorter and/or wider than the opening 192P of the Eson 2 cushion 158P. That is, the height 240 of the opening 192 of the present cushion 158 is smaller than a height 240P of the opening 192P of the Eson 2 cushion 158P. In the illustrated arrangement, the width 242 of the opening 192 of the present cushion 158 is larger than a width 242P of the opening 192P of the Eson 2 cushion 158P. As discussed above, the shorter opening 192 of the present cushion 158 accommodates a lower position on the nose of the user to make the cushion 158 and associated mask 152 feel less obtrusive to the user compared at least to the Eson 2 cushion 158P and mask. The wider opening 192 of the present cushion 158 facilitates the flexing of the seal 158 about the user's nose when the cushion 158 is positioned on the user's nose. Certain differences between an embodiment of the present cushion 158 and the Eson 2 cushion 158P are summarized in the below table.

| | Present Cushion 158 | | | Eson 2 Cushion 158P | | |
|---|---|---|---|---|---|---|
| | Small | Medium | Large | Small | Medium | Large |
| **Seal Dimensions (mm)** | | | | | | |
| Width 236/236P | 56.5 | 58.3 | 63.9 | 53.7 | 59.4 | 64 |
| Height 234/234P | 48 | 52.8 | 57.2 | 53.3 | 58.7 | 63.4 |
| Width:Height | 1.18 | 1.10 | 1.12 | 1.01 | 1.01 | 1.01 |
| **Seal Opening Dimensions (mm)** | | | | | | |
| Width 242/242P | 34.2 | 37.4 | 43.1 | 34.54 | 34.2 | 38.8 |
| Height 240/240P | 22.8 | 23.3 | 32.5 | 28.5 | 34.5 | 39.45 |
| Width:Height | 1.50 | 1.61 | 1.33 | 1.21 | 0.99 | 0.98 |

Differences between another configuration of cushion 158 and the Eson cushion 158P are summarized in the below table.

| | Present Cushion 158 (alternative configuration) | | | Eson 2 Cushion 158P | | |
|---|---|---|---|---|---|---|
| | Small | Medium | Large | Small | Medium | Large |
| **Seal Dimensions (mm)** | | | | | | |
| Width 236/236P | 60.7 | 61.5 | 66.6 | 53.7 | 59.4 | 64 |
| Height 234/234P | 48 | 52.7 | 57.4 | 53.3 | 58.7 | 63.4 |
| Width:Height | 1.26 | 1.16 | 1.16 | 1.01 | 1.01 | 1.01 |
| **Seal Opening Dimensions (mm)** | | | | | | |
| Width 242/242P | 34.2 | 37.4 | 43.1 | 34.54 | 34.2 | 38.8 |
| Height 240/240P | 22.8 | 27.3 | 32.5 | 28.5 | 34.5 | 39.45 |
| Width:Height | 1.5 | 1.37 | 1.33 | 1.21 | 0.99 | 0.98 |

-continued

| | Present Cushion 158 (alternative configuration) | | | Eson 2 Cushion 158P | | |
|---|---|---|---|---|---|---|
| | Small | Medium | Large | Small | Medium | Large |
| **Seal depth (mm)** | | | | | | |
| Depth 244 | 20.66 | 21.24 | 22.10 | — | 15.08 | — |
| Height 234/234P | 48 | 52.7 | 57.4 | | | |
| Depth:Height | 0.43 | 0.40 | 0.39 | — | 0.26 | — |

Figure 39:
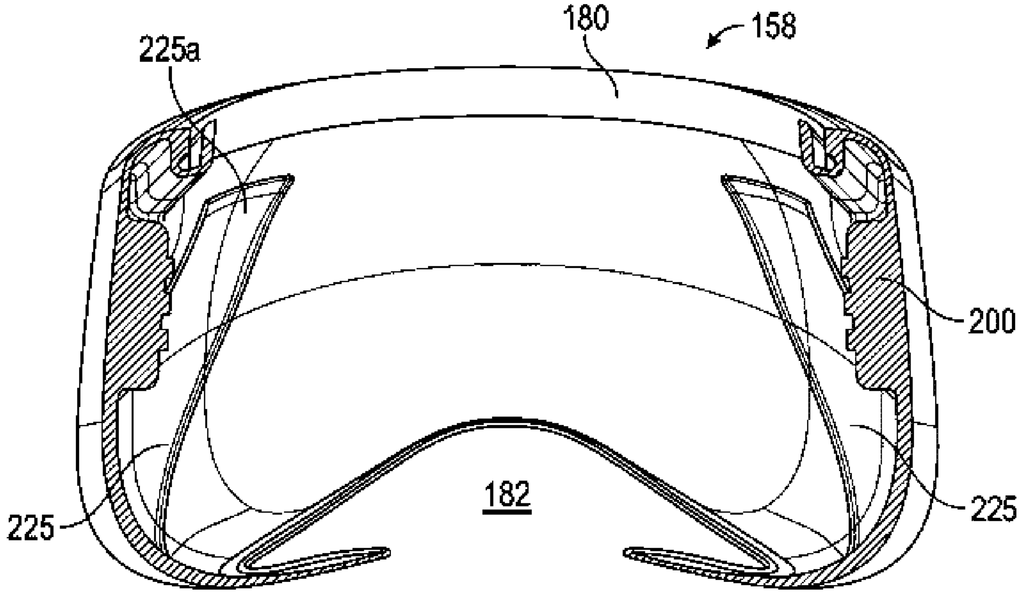
FIG. 39 is a sectional view of the cushion of FIGS. 37 and 38, taken along a transverse or horizontal plane of the cushion.
Figure 40:
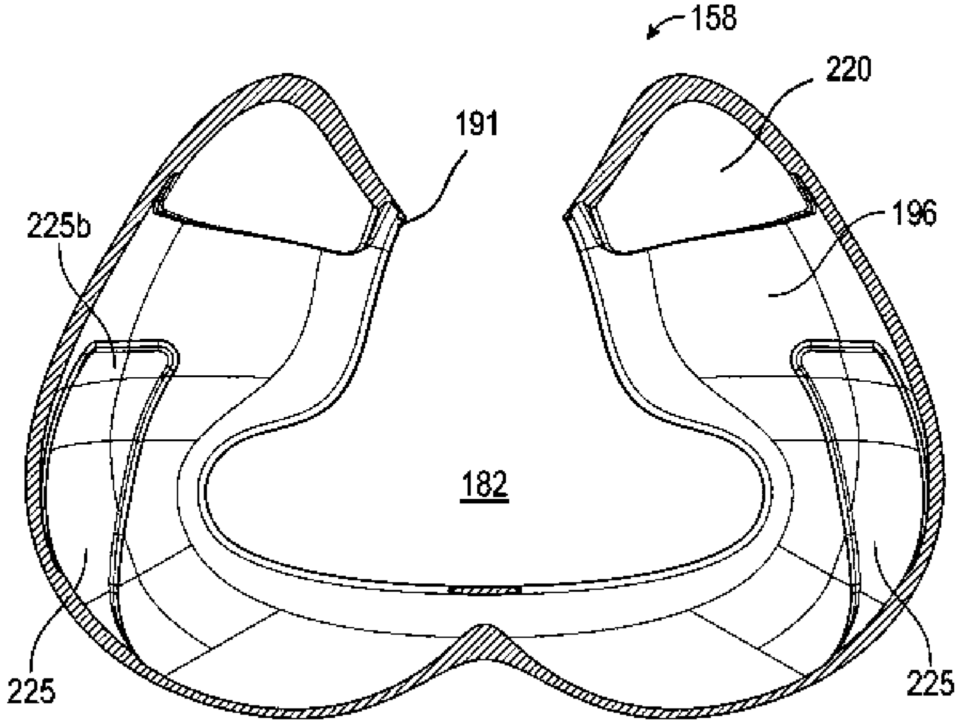
FIG. 40 is a front sectional view of the cushion of FIGS. 37 to 39, taken along a coronal or frontal plane of the cushion.

With reference again to FIG. 37, and also to FIGS. 39 and 40, in some configurations the cushion 158 includes a pair of lower thickened portions 225 (only one of which is shown in FIG. 37). In the illustrated arrangements, each of the lower portions 225 is an elongate thickened portion of cushion 158, extending into the interior of the cushion 158. In some configurations, the portions of the side wall including the lower thickened portions 225 may be thicker than the adjacent portions of side wall 188 and/or end wall 184 by between about 0.1 and 0.6 mm. In some configurations, the portions of the side wall including the lower thickened portions 225 may be thicker by between about 0.1 and 0.3 mm. In some configurations, the portions of the side wall including the lower thickened portions 225 may be thicker by about 0.2 mm. In some configurations, the lower thickened portions 225 may be about 1.2 mm thick. In some configurations, the absolute and/or relative thickness of the lower thickened portions may be substantially uniform along their length.

Figure 38:
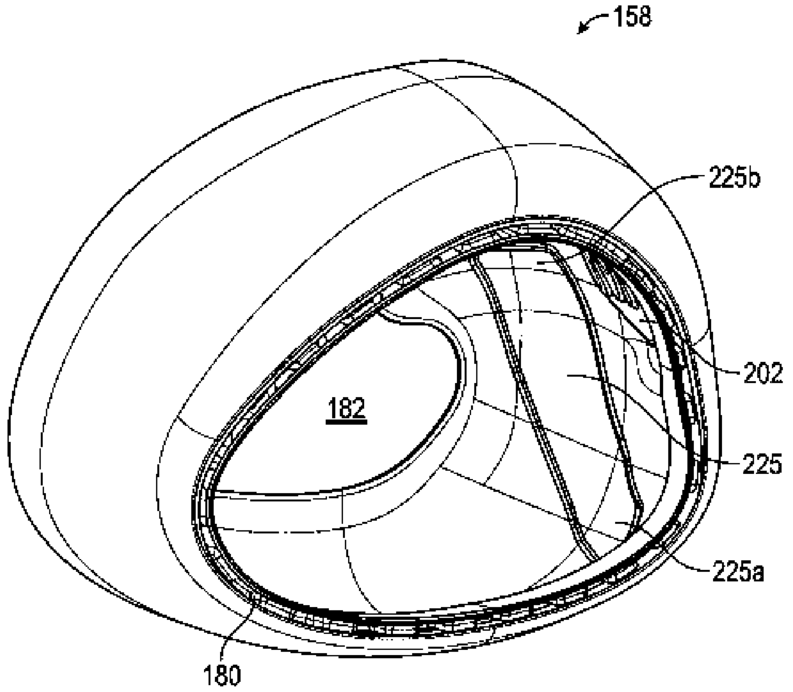
FIG. 38 is a perspective view of the cushion of FIG. 37.

As shown in FIGS. 37, 39 and 40, the lower thickened portions 225 are at least partially curved. When viewed from a side of the cushion 158, as shown in FIG. 37, the lower thickened portions 225 appear to curve in an upward direction, in particular at an intermediate portion of the lower thickened portion 225 at a transition of the cushion 158 from side wall 188 to end wall 184. Each lower thickened portion 225 curves or curls in a direction substantially normal to their respective major surfaces. In other words, the thickened portions 225 form a substantial plane curve, albeit having a width extending in a direction substantially perpendicular to the plane of the curve. When viewed from a particular angle, a lower thickened portion 225 may appear substantially linear, as shown in FIG. 38. However, when the cushion 158 is viewed from another angle, the lower thickened portion 225 appears to have a sideways curve, as best shown in FIG. 37. If the lower thickened portion 225 and adjacent portions of the side wall 188 and end wall 184 are flattened, the lower thickened portion 225 will form a plane curve. The lower thickened portions 225 may also have a twist along at least a portion of their length.

The lower thickened portions 225 have a first end **225*a* provided at or adjacent or near to respective lower corners of the substantially triangular side wall 188 of the cushion 158, at or adjacent or near to the rim 180. From the first end, the lower thickened portions 225 extend substantially rearwardly (that is, towards the user, in use) before curving upwardly and terminating at a second end in the end wall 184 adjacent the cheek surfaces 196 of the face contacting surface 186, on opposing sides of the opening 192. Viewed from the top, as shown in FIG. 39, or bottom of the cushion 158, the lower thickened portions 225 are splayed relative to each other, diverging rearwardly from the first ends 225*a* towards an intermediate portion. Viewed from the front, as shown in FIG. 40, or rear of the cushion, the the lower thickened portions 225 converge upwardly from an intermediate portion towards the second ends 225***b*. It has been found that this diverging-converging arrangement helps to avoid contact with relatively sensitive areas of the user's face. The lower thickened portions 225 terminate at the second ends vertically above, and horizontally spaced from, a lower region 202 of the thickened band 200, as shown in FIG. 37. The lower thickened portions 225 terminate at the second ends vertically below, and vertically spaced from, a respective lowermost portion of the thickened portions 220. The lower thickened portions 225 extend under, and terminate at the first ends 225*a* vertically below and spaced from, respective lower thickened corners 189 of side wall 188.

In some configurations, a straight-line distance (i.e. the most direct path through three-dimensional space) between the first end 225*a* and the second end 225*b* of the lower thickened portions 225 is between about 30 and 35 mm. In some configurations, the straight-line distance is about 32.9 mm. The second ends 225*b* of the lower thickened portions 225 are spaced from the opening 192 so that they do not contact sensitive areas of the patient's nose. In some configurations, a minimum spacing between the lower thickened portions 225 and the opening 192 is at least 4 mm. In some configurations, the minimum spacing is between about 5 and 6 mm. In some configurations, the minimum spacing may be between about 5.2 and 5.5 mm.

The lower first ends 225*a* of the lower thickened portions 225 may be narrower than the upper second ends 225*b*. The thickened portions 225 taper from the second end 225*b* to the first end 225*a*, which may help avoid or reduce contact with sensitive areas of the patient's upper lip. In some configurations, the width of the first end is between about 4 and 6 mm. In some configurations, the width of the first end is about 4.7 mm, 4.8 mm or 5.0 mm. In some configurations, the width of the second end is between about 7 and 8 mm. In some configurations, the width of the second end is about 7.4 or 7.8 mm. In some configurations, the second end 225*b* is wider than the first end 225*a* by at least 50%. In some configurations, the second end 225*b* is wider than the first end 225*a* by between about 50% and 60%. In some configurations, the second end 225*b* is wider than the first end 225*a* by about 54%.

The thickened portions 225 have been found to transfer force toward the housing 162 rather than the user, reduce collapsing of the cushion, and/or provide additional support transferring sealing forces to the user's cheeks rather than more sensitive areas such as the upper lip and lower regions of the nose.

With reference again to FIG. 37, in some configurations a thickness of the side wall 188 may taper gradually in a bottom portion of the cushion 158, from the rim 180 rearwardly towards the lower surface 194 of the face contacting surface 186. The taper may be non-linear, and in particular may be a substantially exponential taper. By contrast, in other regions of the cushion 158, there is a step-change in the thickness of the side wall 188 from the relatively thick rim 180 to the immediately adjacent portion of the side wall 188, and the thickness of the side wall 188 remains substantially uniform between the rim 180 and end wall 184, but for the thickened band 200, thickened panels 220 and joining pads 221.

The taper of the side wall 188 in the bottom portion of the cushion 158 is more gradual than that of the prior Eson 2 cushion, which is shown in FIG. 6-1. In some configurations, the side wall 188 may taper to half (50%) of the thickness of the rim 180 at least about 3 mm from the rim 180. In some configurations, the side wall tapers to half of the thickness of the rim 180 at least about 4 mm from the rim 180. In some configurations, the side wall tapers to half of the thickness of the rim 180 at least about 5.5 mm from the rim 180. In some configurations, the side wall 188 may taper to a quarter (25%) of the thickness of the rim 180 at least about 7 mm from the rim 180. In some configurations, the side wall tapers to a quarter of the thickness of the rim 180 at least about 8 mm from the rim 180. In some configurations, the side wall tapers to a quarter of the thickness of the rim 180 at least about 9.4 mm from the rim 180.

Headgear-Interface Connection

With reference to FIGS. 8-16, an illustrated connection arrangement 248 between the mask 152 and the headgear 154 is configured to secure the mask 152 in an operable position on the face of the user. In some configurations, the connection arrangement 248 is configured to provide a suitable level of stability to the mask 152 with a single connection between the headgear 154 and the mask 152 on each side of the mask. Accordingly, the illustrated mask assembly 150 does not include a forehead support or corresponding upper headgear portion. As a result, the illustrated mask assembly 150 avoids any portion of the mask frame 156 extending above the cushion module 160 so that the mask assembly 150 is less obtrusive to the user at least in comparison to masks having a forehead support.

In the illustrated mask assembly 150, a connection arrangement 248 is provided on each side of the mask 152. The connection arrangement 248 can be identical or substantially the same on each side of the mask 152, except that the connection arrangements 248 may be mirror images of one another. Accordingly, only one connection arrangement 248 is described in detail herein. However, the description can apply equally to the other connection arrangement 248. Alternatively, the connection arrangements 248 on each side of the mask 152 may differ slightly from each other, as described in further detail below. The illustrated connection arrangement 248 is a removable connection. In an alternative arrangement, the headgear 154 may be permanently connected to the mask 152 on one side and employ a removable connection (e.g., the connection arrangement 248) on the other side.

Figure 8:
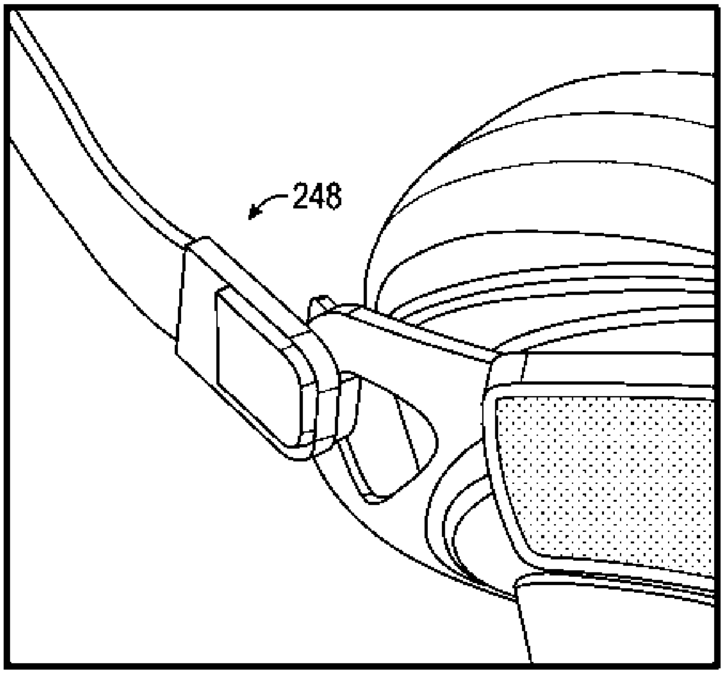
FIG. 8 is a perspective view of a connection arrangement between the nasal mask and the headgear of FIG. 2.
Figure 9:
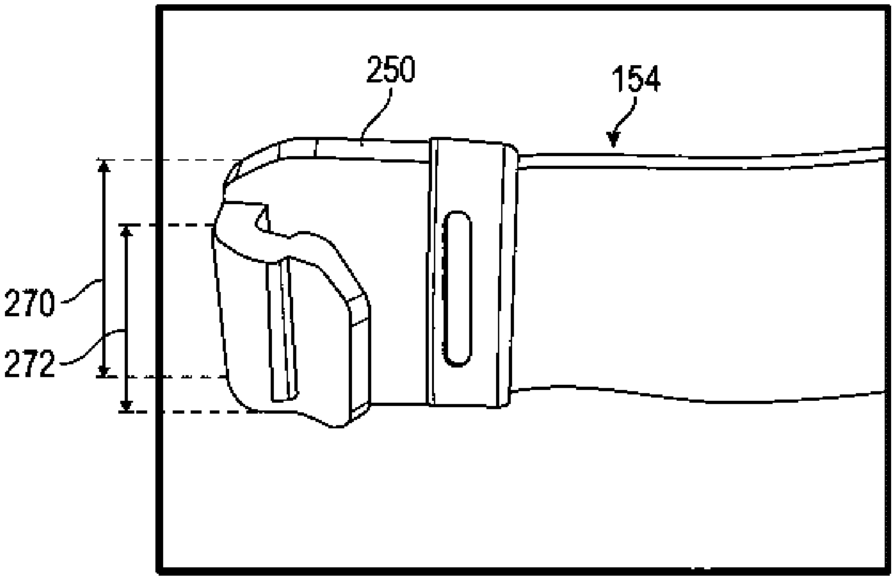
FIG. 9 is a perspective view of a clip of the connection arrangement of FIG. 8 and a portion of the headgear.

With reference to FIG. 8, the connection arrangement 248 includes a headgear clip 250 that is removably connectable with the frame 156. FIG. 8 illustrates the headgear clip 250 attached to the frame 156. With further reference to FIG. 10, each side of the frame 156 generally comprises an ear 252 that is associated with each headgear clip 250. The ears 252 preferably extend generally laterally outward from a central portion 254 of the frame 156, which includes the connector portion 170 and an opening 256 that communicates with an interior of the connector portion 170 and receives the connection tube 164. The ears 252 can be configured to locate the clips 250 further forward and/or upward relative to a conventional four-point headgear arrangement to position the clips 250 into or further into the peripheral vision of the user. This may make it easier for at least some patients to engage and/or disengage the clips 250 from the ears 252.

In the illustrated arrangement, the connection arrangement 248 is a hook-and-post connector. However, other connector types could also be used. In the illustrated arrangement, each of the ears 252 of the frame 156 includes a post 260. However, in other arrangements the posts 260 could be located on the clips 250. In the illustrated arrangement, each of the clips 250 includes a hook structure 266. However, in other arrangements the hook structure 266 could be located on the frame 156. The hook structure 262 and the post 260 provide an easily connectable and disconnectable configuration. In some configurations, the clips 250 are symmetrical such that a single clip can be used on both the left and the right sides of the frame 156. In other configurations, the posts 260 and/or clips 250 on each side of the mask 152 may differ in a way which reduces the chance of improper connection between the headgear 154 and the frame 156.

The illustrated clip 250 includes a base portion or base 264 and a hook portion or hook 266. The base 264 and the hook 266 cooperate to form the hook structure 262. The hook 266 extends from a side surface of a forward end of the base 264. In some configurations, a forward end of the base 264 is aligned with a forward end of the hook 266. The base 264 defines a height 270 in a direction parallel to a longitudinal axis A of the post 260 when the clip 250 is connected to the post 260. Similarly, the hook 266 defines a height 272 in the same direction. In some configurations, the height 270 of the base 264 is larger than the height 272 of the hook 266. In addition, a portion of the base 264 can extend beyond both an upper end and a lower end of the hook 266 in the direction of the heights 270, 272. In some configurations, the hook 266 can be centered relative to the base 264 in a vertical direction or the direction of the heights 270, 272.

Figure 11:
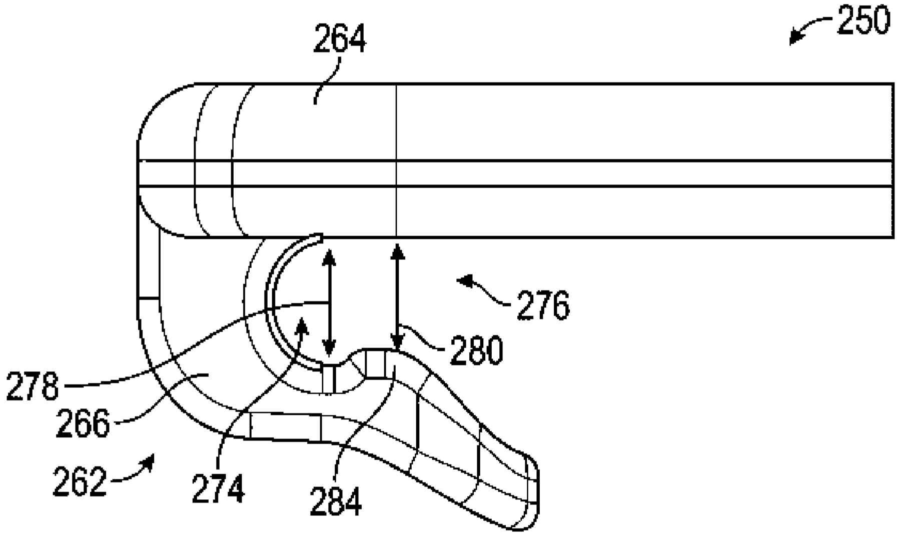
FIG. 11 is a top view of the clip of FIG. 9.
Figure 12:
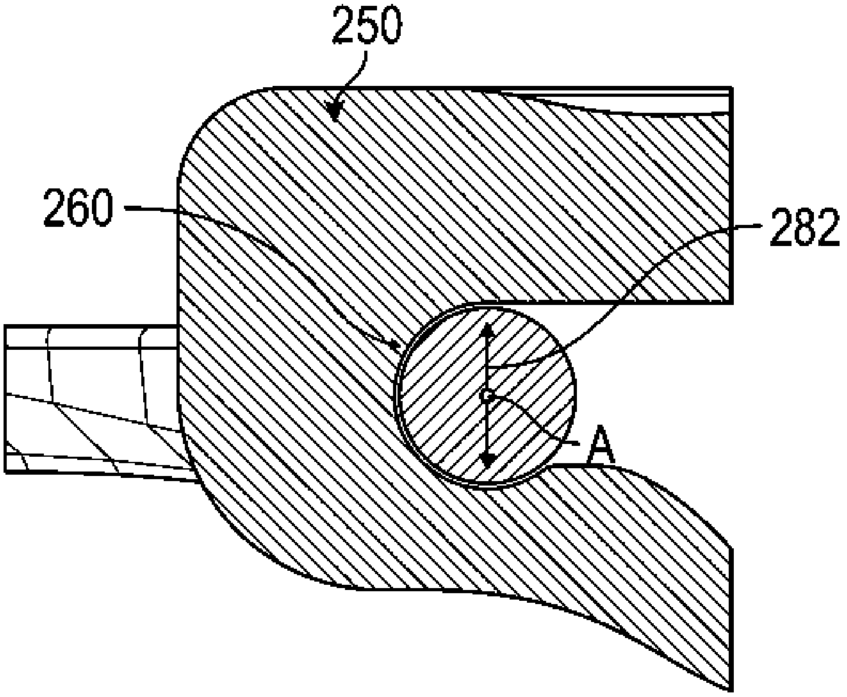
FIG. 12 is a sectional view of a portion of the connection arrangement of FIG. 8.
Figures 1, 12:
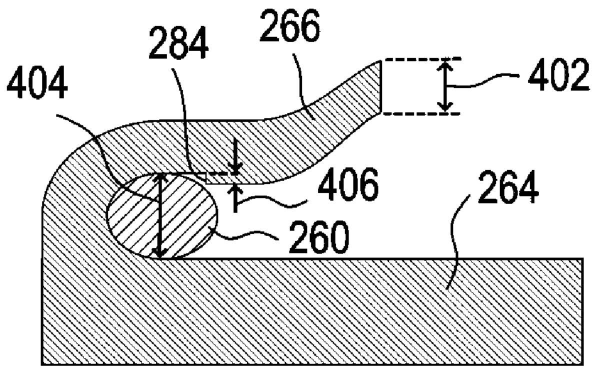

With reference to FIG. 11, the base 264 and the hook 266 cooperate to define a space 274 sized and shaped to accommodate the post 160. The post 160 can be inserted into the space 274 through a generally rearward-facing opening 276. The space 274 can define a maximum width 278 in a direction perpendicular to the longitudinal axis A of the post 260 when the clip 250 is connected to the post 260 or a direction perpendicular to the direction of the heights 270, 272. The opening 276 can define a minimum width 280 in a direction parallel to the maximum width 278 of the space 274. With reference to FIG. 12, the post 160 can define a maximum width, which because the illustrated post 160 is cylindrical can be referred to herein as a diameter 282. The width 278 of the space 274 can be equal to or slightly larger than the diameter 282 to create a tight fit between the post 160 and the clip 250 when the clip 250 is connected to the post 160. Such an arrangement can enhance the stability of the connection arrangement 248, as discussed further below. In one example configuration, the diameter 282 can be 2.47 mm, and the width 278 can be 2.52 mm. In some configurations, the width 278 is about 2% greater than the diameter 282. In other configurations, the width 278 of the space 274 could be smaller than the diameter of post 160, whereby the hook 266 does not fully elastically recover upon insertion of the post 160.

With reference to FIG. 12-1, in one example configuration the clip 250 has a thickness 402 of about 1.5 mm at the distal end of the hook 266. In another example configuration, the thickness 402 may be about 1.3 mm. The hook opening diameter 404 may be about 3.1 mm for a post 260 having a diameter of about 3.0 mm, providing a clearance of about 0.05 mm on each side of the post 260. The amount of interference 406 between the post 260 and protrusion 284 in this configuration is about 0.25 mm.

The width 280 of the opening 276 can be less than the maximum width 278 of the space 274 and/or the diameter of the post 260 to provide an interference fit between the hook structure 262 and the post 260 such that the clip 250 is less likely to inadvertently disengage during use. In one particular configuration, it was found that an interference of greater than 0.25 mm and less than 0.30 mm was suitable, with an interference of 0.28 mm being preferred. In the illustrated arrangement, the opening 276 of the clip 250 is defined between the base 264 and a protruding portion, interference protrusion or, simply, protrusion 284 of the hook 266. In the illustrated arrangement, the space 274 defines a part-cylindrical shape, such as a semi-cylindrical shape, which can contact a corresponding surface of the cylindrical post 260. The protrusion 284 can be spaced from the portion of the hook 266 that defines the part-cylindrical shape, such that a space exists between the post 260 and the hook 266 when the post 260, as illustrated in FIG. 12.

The interference fit between the clip 250 and the post 160 can be configured for a desired disconnection force, which can be high enough to inhibit unintentional disengagement but low enough to allow for convenient intentional disengagement by the user. In the illustrated arrangement, it was determined that an interference—or difference between the width 280 of the opening 276 and a width of the space 274 and/or diameter 282 of the post 260—of greater than 0.25 mm and less than 0.3 mm is desirable. For example, the interference can be between about 0.26 mm-0.29 mm, between about 0.27 mm-0.29 mm, or can be about 0.28 mm. Such an interference is based on the dimensions of the post 260 and/or space 274 disclosed herein and can be represented as a percentage or proportion of those dimension. Moreover, the interference may be modified based on the shape or size of the hook 266 and/or the material of the clip 250. In some configurations, lead-in and lead-out angles of the protrusion 284 may be configured so that a required connection force is less than a required disconnection force, to prevent inadvertent disconnection without making connection unnecessarily difficult.

In some configurations, the interference fit between the clip 250 and the post 160 can be configured to provide tactile and/or audible feedback confirming proper connection between the components.

With primary reference to FIG. 10, each ear 252 defines an opening 290 that is located adjacent to the post 260. That is, the post 260 defines a portion of a boundary of the opening 290. The opening 290 is configured to receive and accommodate at least the hook 266 of the clip 250 to permit the clip 250 to be connected to the post 260. In the illustrated configuration, the ear 252 and the opening 290 are configured to restrict movement of the clip 250 relative to the frame 156. In some configurations, the ear 252 and the opening 290 are configured to restrict rotational movement of the clip 250 about an axis perpendicular to the longitudinal axis A of the post 260. Such an arrangement can increase the stability of the mask 152 on the face of the user, as described further below. In some configurations, the ear 252 and the opening 290 are configured to limit rotational movement of the clip 250 about the longitudinal axis A of the post 260. Such an arrangement can inhibit undesired disconnection of the clip 250 from the mask 152.

The illustrated opening 290 is generally trapezoidal in shape, with an end opposite the post 260 having a length that is larger than the length of the post 260. Such an arrangement enhances the ability of the user to pass the hook 266 through the opening 290 without being able to see the mask 152, which can often be the case when the user is donning the mask assembly 150. However, in other arrangements, the opening 290 can have any desired shape. At least a portion of each the opposing sides of the opening 290, each extending between the post 260 and the end of the opening 290 opposing the post 260, converge towards the post 260. Such an arrangement may help guide the clip 250 towards the post 260.

The illustrated opening 290 includes a narrowed portion 292 relative to an adjacent portion of the opening 290. The narrowed portion 292 is located adjacent the post 260. The narrowed portion 292 along with the post 260 define a space that receives the hook 266 of the clip 250. The narrowed portion 292 can be defined by a first or upper surface 294 and an opposed second or lower surface 296. Each of the upper surface 294 and the lower surface 296 originates at the post 260 and extends away from the post 260 to a terminal end. The space of the narrowed portion 292 can be defined between the post 260 and an imaginary line connecting the terminal ends of the upper and lower surfaces 294, 296 in a horizontal direction and between the upper surface 294 and the lower surface 296 in a vertical direction. In some configurations, the portions of opposing sides of the opening 290 which converge toward the post 260 are provided adjacent to, and converging towards, the respective upper and lower surfaces 294, 296 of the narrowed portion 292.

The size and/or shape of the space of the narrowed portion 292 can match or be substantially the same as the size and/or shape, in particular the cross-sectional size and/or shape, of the base or connecting portion of the hook 266 that occupies the narrowed portion 292 when the clip 250 is connected to the post 260. In some configurations, the size and/or shape of the space of the narrowed portion 292 can be slightly larger than the base or connecting portion of the hook 266 that occupies the narrowed portion 292 when the clip 250 is connected to the post 260. Preferably, the relative sizes are selected to allow convenient insertion of the hook 266 into the narrowed portion 292, but a tight enough fit to restrict any substantial rotation of the clip 250 in a direction perpendicular to the longitudinal axis A of the post 260, as described above. Such rotation can be restricted at least in part by contact between the base or connecting portion of the hook 266 that occupies the narrowed portion 292 and the upper and lower surfaces 294, 296 of the narrowed portion 292.

In some configurations, the hook 266 is shaped to span the space of the narrowed portion 292 when the hook 266 is engaged with the post 260. In some configurations, the hook 266 can occupy an entirety or a substantial entirety of the space of the narrowed portion 292. Accordingly, a distance between the upper surface 294 and the lower surface 296 in a direction parallel to the longitudinal axis A of the post 260 is equal to or only slightly greater than the height 272 of the hook 266. Such an arrangement limits or prevents axial movement of the clip 250 along longitudinal axis A of the post 260 in use. In some configurations, the base portion of the hook 266 which extends from the base 264 of the clip 250 can be the thickest portion of the hook 266 or define the largest wall thickness of the hook 266. The thickness of a portion or an entirety of the base portion of the hook 266 can be selected such that the hook 266 extends along an entirety of one or both of the upper surface 294 and the lower surface 296 of the narrowed portion 292. In some configurations, the hook 266 may extend beyond the terminal ends of one or both of the upper surface 294 and the lower surface 296.

The shape and/or orientation of the upper surface 294 can correspond to the shape and/or orientation of the corresponding upper surface of the hook 266. Similarly, the shape and/or orientation of the lower surface 296 can correspond to the shape and/or orientation of the corresponding lower surface of the hook 266. In the illustrated arrangement, the upper surface 294 is parallel to or substantially parallel to the lower surface 296. In addition, the upper surface and the lower surface of the hook 266 are parallel or substantially parallel. Accordingly, when the fit between the hook 266 and the narrowed portion 292 is tight, the hook 266 is in contact with an entirety or a substantial entirety of the upper and lower surfaces 294, 296. Even if some clearance is provided between the hook 266 and the narrowed portion 292, contact occurs at smaller angular movements in comparison to an arrangement in which the hook 266 does not correspond in size and/or orientation with the upper surface 294 and the lower surface 296 of the narrowed portion 292.

In some configurations, the clip 250 can be configured to allow pivoting movement relative to the post 260 and/or the frame 156 about the longitudinal axis A of the post 260. Such an arrangement permits the angular orientation of the clip 250 relative to the frame 156 to be varied such that differing shapes of heads can be easily accommodated. However, in some configurations, pivoting movement of the clip 250 can be limited. For example, because the base 264 of the clip 250 has height 270 that is larger than the height 272 of the hook 266, the base 264 can contact the frame 156. In some configurations, the base 264 can contact a portion of the frame 156 above and/or below the post 260 and/or narrowed portion 292 to restrict pivotal movement of the clip 250 toward and/or away from the frame 156.

Figure 13:
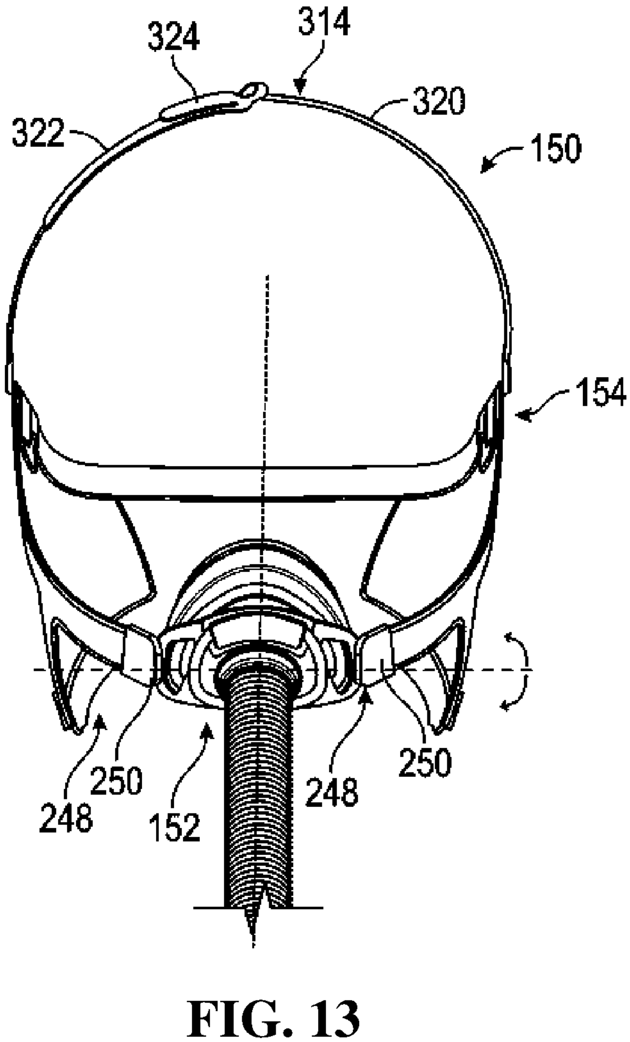
FIG. 13 is a front view of the nasal mask assembly of FIG. 2 illustrating a direction in which rotation of the nasal mask is restricted by the connection arrangement.
Figure 14:
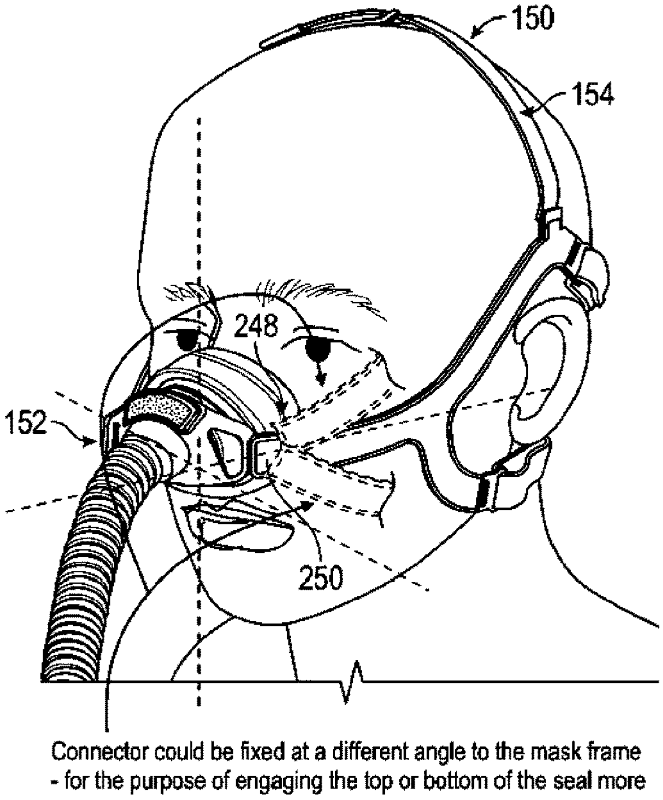
FIG. 14 is a perspective view of the nasal mask assembly of FIG. 2 illustrating alternative angles of a front strap of the headgear arrangement.

FIG. 13-16 illustrate interaction between the mask 152 and the headgear 154 resulting from or facilitated by the engagement of the clip 250 and post 160 of the connection arrangement 248. FIG. 13 illustrates the direction that rotation is limited, restricted or prevented by the connection arrangement 248, in particular the positioning of the hook 266 within the narrowed portion 292 of the opening 290 when the clip 250 is connected to the post 260. As described above, the connection arrangement 248 can limit, restrict or prevent movement of the clip 250 about an axis that is perpendicular to the longitudinal axis A of the post 260. In the context of the mask assembly 150, movement of the clip 250 within a vertical plane or about a horizontal axis is limited, restricted or prevented. As described further below, when the headgear 154 provides sufficient support to the clip 250, the headgear 154 in combination with the connection arrangement 248 limits, restricts or prevents excessive rocking of the mask 152 on the user's face. FIG. 14 illustrates that the connection arrangement 248 can be configured such that the headgear 154 extends from the mask 152 at a desired angle for the particular application or headgear type. That is, the connector could be fixed at a different angle to the mask frame for the purpose of engaging the top of bottom of the seal more.

Figure 15:
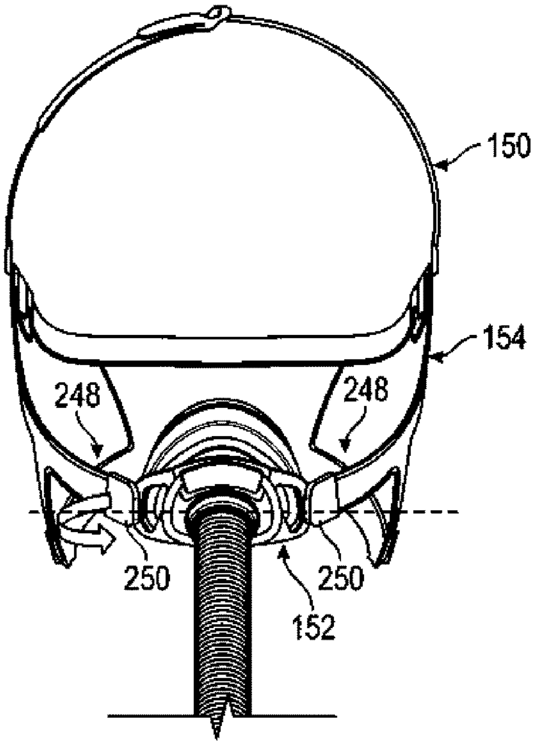
FIG. 15 is a front view of the nasal mask assembly of FIG. 2 illustrating a direction in which rotation of the front strap of the headgear is limited by the connection arrangement.
Figure 16:
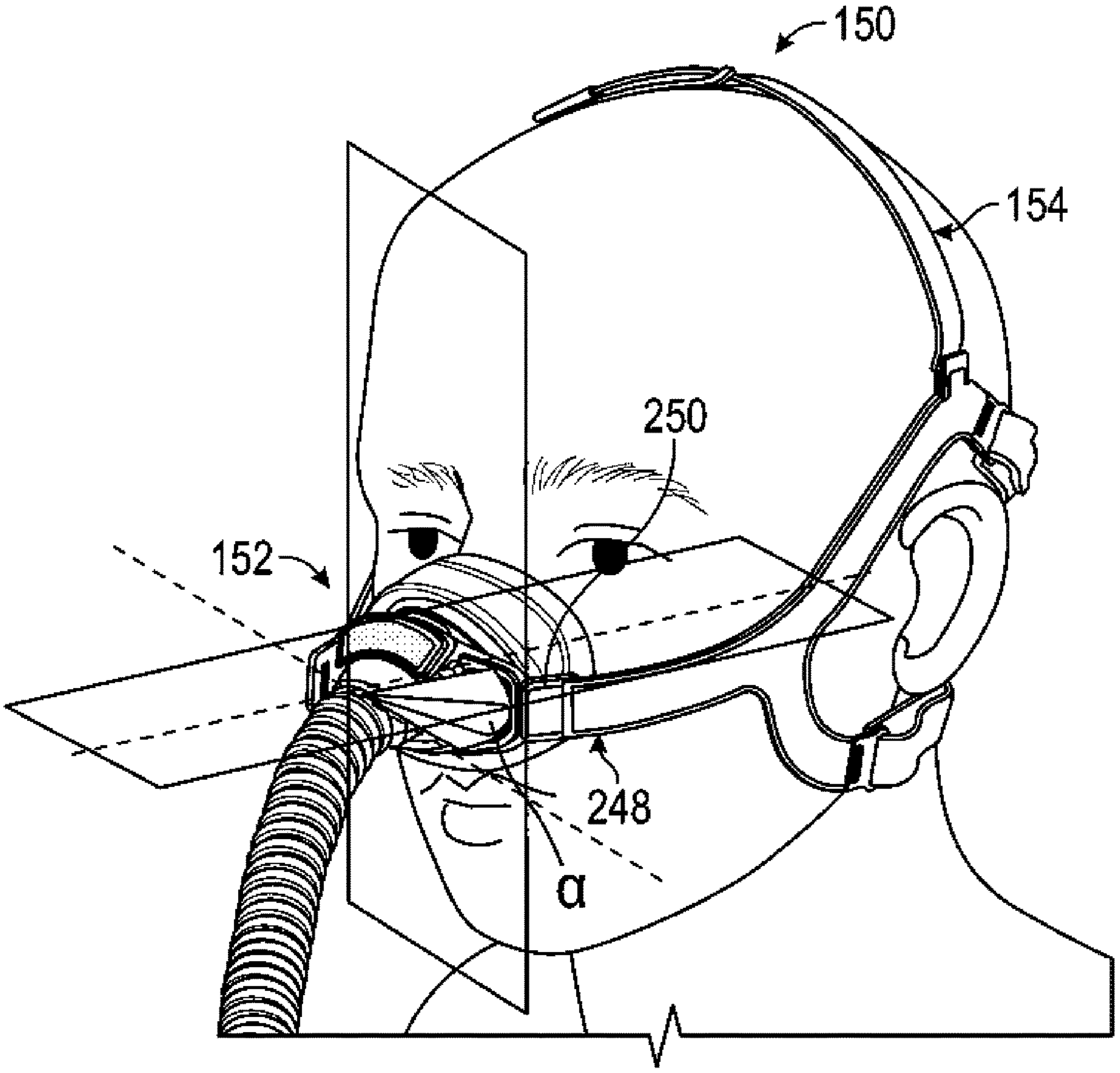
FIG. 16 is a perspective view of the nasal mask assembly of FIG. 2 illustrating a possible functional range and an example operative range of rotation of the front strap permitted by the connection arrangement.

FIGS. 15 and 16 illustrate the direction and the range within which rotation of the clip 250 about the longitudinal axis A of post 260 is limited relative to the mask 152 to permit the mask assembly 150 to fit user's with different head widths or sizes. FIG. 15 illustrates that some rotation of the clip 250 about the longitudinal axis A of the post 260 is permitted. In the context of the overall mask assembly 150, this rotation is within a horizontal plane or about a vertical axis. FIG. 16 illustrates an example range of motion that can be permitted. For example, in some configurations, a functional range can be between 0-90 degrees. However, in some configurations, the allowable or operative range is more limited. For example, in the illustrated arrangement, an operative range a of about 15 degrees is provided. The operative range a of about 15 degrees is permitted between the angles of about 45 and about 60 degrees relative to the central, vertical plane that bisects the mask assembly 150 into a right and left lateral portions. Such a range can permit fitment of an acceptable range of user head sizes while reducing or minimizing undesired disconnection of the connection arrangement 248 that could occur with excessive rotational movement. In other configurations, the operative range may be between about 10 degrees and about 30 degrees, and permitted between angles anywhere within the range of about 20 degrees to 80 degrees with respect to the central, vertical plane.

Figure 17A:
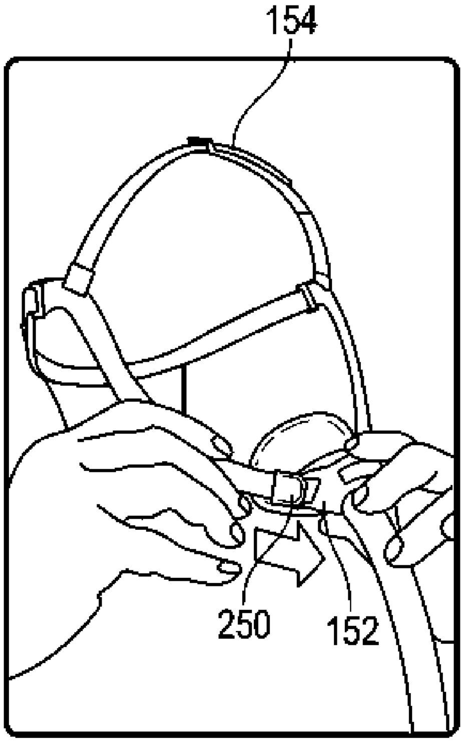
FIGS. 17A-17D illustrate a method of fitting the nasal mask assembly to a user.

FIGS. 17A-17D illustrate a method of fitting the mask assembly 150 to a user. In some configurations, the mask assembly 150 and connection arrangement(s) 248 can be configured to permit fitting (applying or donning) of the mask assembly 150 in substantially a single motion with the user using a single hand to make the connection between the headgear 154 and the mask 152. The user's other hand can be used to support the mask 152. FIG. 17A illustrates the direction of movement for disconnecting the headgear 154 from the mask 152. That is, the headgear 154 (and clip 250) can be moved in a forward direction away from the user to disconnect the clip 250 from the post 260 by forcing the post 260 to move through the opening 276 of the clip 250 against a disconnection force created by the resiliency of the hook 266. The removal of the headgear 154 shown in FIG. 17A can be done to allow removal of the mask assembly 150 from the user or to create an open loop before the mask assembly 150 is applied to the user.

Figure 17B:
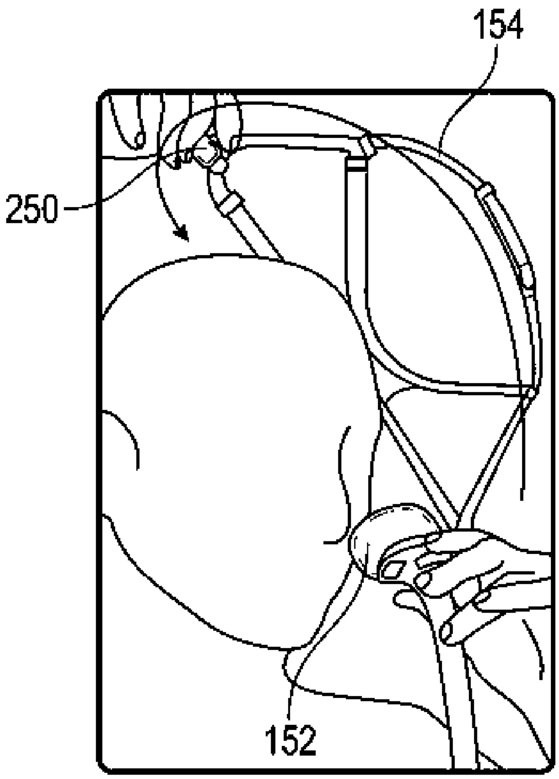
Figure 17C:
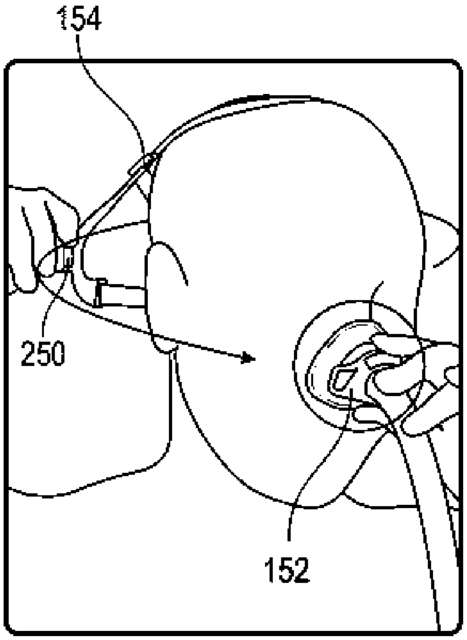
Figure 17D:
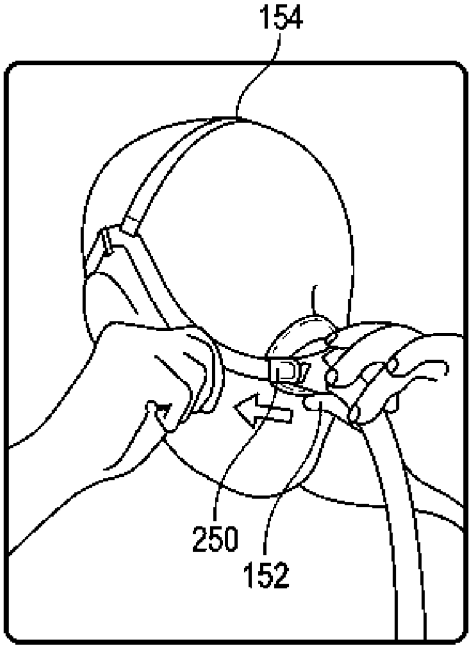

FIGS. 17B and 17C illustrate that the mask 152 can be located near or on the user's nose and the disconnected end of the headgear 154 can be swung around or over the user's head and toward the cooperating side of the mask 152. As illustrated in FIG. 17D, the clip 250 can be manipulated to pass the hook 266 through the opening 290 of the frame 156 of the mask 152. The headgear 154 and clip 250 can be moved in a rearward direction to force the post 260 through the opening 276 of the clip 250 and into the space 274 to connect the clip 250 to the frame 156 and the headgear 154 to the mask 152. Because only a single headgear clip 250 is provided on each side of the mask assembly 150, the connection of the headgear 154 to the mask 152 can be accomplished in a single motion with one hand. To remove the mask assembly 150, the user can disengage the clip 250 from the mask 152 as shown and described in connection with FIG. 17A.

Figure 18:
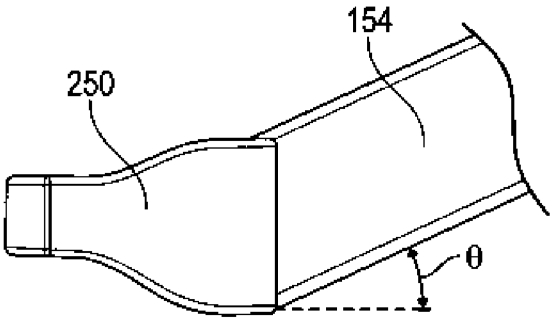
FIG. 18 illustrates a clip and a front strap of a headgear arrangement orientated at an angle relative to the clip.

FIG. 18 illustrates that the strap or portion of the headgear 154 that is connected to the clip 250 can be oriented at an angle relative to the clip 250. In other words, a longitudinal axis or a centerline of the headgear 154 can define an angle with respect to a longitudinal axis or centerline of the clip 250. As used herein, oriented at an angle or defining an angle means that the axes or centerlines do not form a straight line. In other words, two lines or axes that are orientated at an angle do not define an angle of 0 or 180 degrees. Such an arrangement can permit the clip 250 to be oriented as desired with respect to the frame 156 while permitting the headgear 154 to be oriented as desired with respect to the head of the user without regard to the orientation of the frame 156.

Figure 19:
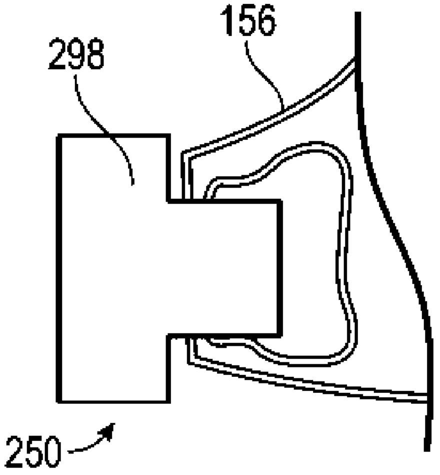
FIG. 19 illustrates an alternative clip having an enlarged rear portion connected to a mask frame.
Figure 20:
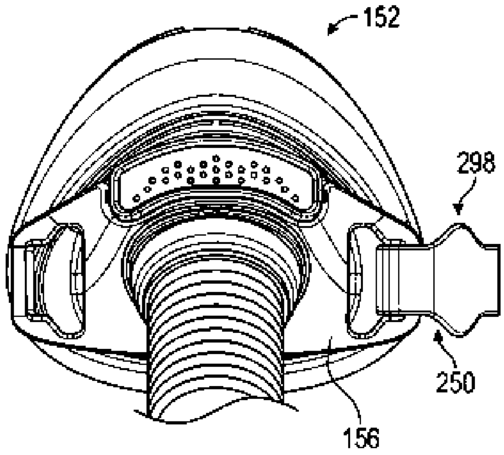
FIG. 20 is a front view of a nasal mask assembly with a clip having an enlarged rear portion connected thereto.
Figure 21:
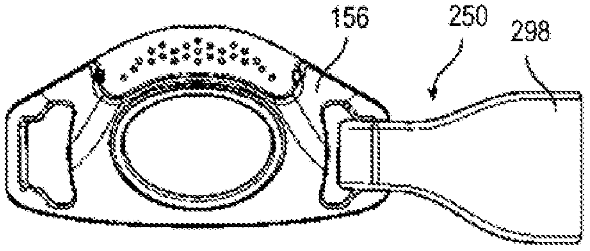
FIG. 21 is a front view of a mask frame with a clip having an enlarged rear portion connected thereto.

FIGS. 19-21 illustrated that a rearward portion 298 of the clip 250 located rearward of the connection with the frame 156 of the mask 152 can be enlarged relative to the portion connected to the frame 156. The enlarged rearward portion 298 can be provided to enhance the user's grip of the clip 250. In some configurations, the enlarged rearward portion 298 can be configured to limit rotation of the clip 250 by contact with the end of the frame 156 as shown in FIG. 19.

In some configurations, the headgear clip 250 may include additional structures to improve the connection arrangement 248. FIGS. 41-45 illustrate modified versions of clip 250 in which the base 264 includes a projection 265 that extends outwardly from, preferably at least partially in a direction substantially perpendicular to, the outwardly-facing major surface of the base 264. In the illustrated clips 250, the projection 265 spans the width of the headgear clip 250. In some configurations, however, the projection 265 may span only a portion of the width of the base 264. In some configurations, the projection 265 is located at, adjacent, or towards a rearward portion 298 of the clip 250, near the front strap portion 306, which may help to keep the user's hand clear of the hook 266 so that connection and/or disconnection of the clip 250 is not obstructed.

In some configurations, the projection 265 may project from the adjacent portion(s) of the base 264 by between about 2 and 5 mm. In some configurations, the projection 265 may project from the base 264 by around 3.5 mm. In some configurations, the projection 265 may project from the base 264 by a height equal to between about 50% and 150% of a thickness of the base 264. In some configurations the projection 265 may have a height about equal to a thickness of the base 264.

The projection 265 may assist the user when pushing the headgear clip 250 towards the frame 156 during donning and/or doffing. The projection 265 may alternatively, or additionally, assist the user when pulling the clip 250 in a direction away from the mask frame (i.e. pulling the hook 233 towards the frame) to secure the interference connection between the clip 250 and the post 260 of the frame 156.

Each of the headgear clips 250 in FIGS. 41-44 also include a depression 267 in the outwardly-facing portion of the base 264. The depression 267 acts as a tactile feature to accommodate a finger or thumb of the user, and in particular the index finger. The presence of the depression 267, forward of and substantially adjacent to the projection 265, may increase the effective height of the projection 265 relative to the base 264. The depression may provide a visual cue to the user. The provision of tactile and/or visual cues may aid the user in locating a finger or thumb on the clip 250 for connecting and/or disconnecting the clip 250 to/from the frame 156. As shown in each of FIGS. 41-44, at least a portion of the depression 267 may also provide an inclined or substantially perpendicular ridge or wall 268 against which a user may apply a force to guide the clip 250 towards the frame 156 during donning, and/or to remove the clip 250 from the frame 156 when doffing the patient interface assembly 150.

Figure 42:
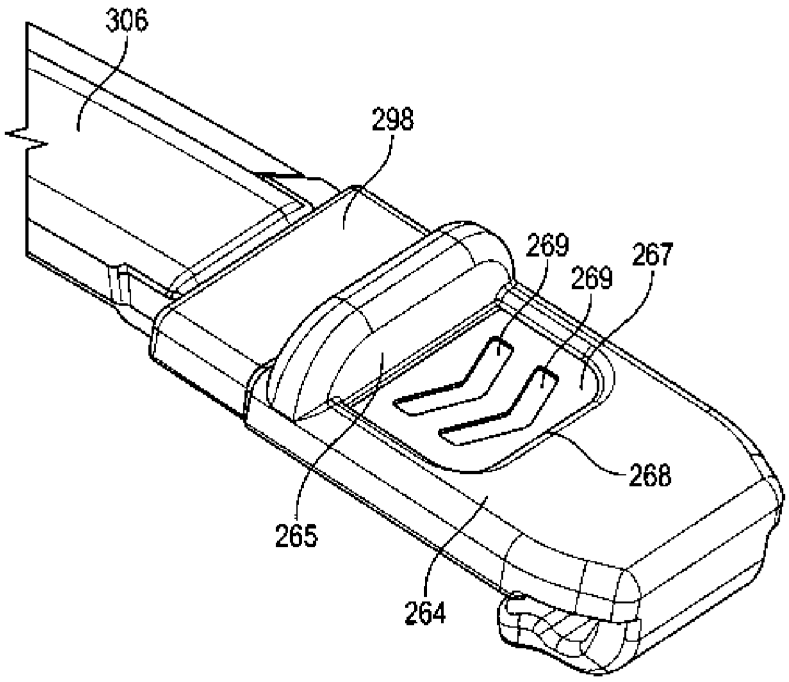
FIG. 42 is a perspective view of another modified version of the headgear clip of FIG. 9.

As shown in FIG. 42, the base 264 may be provided with one or more ridges 269. The ridges 269 provide for additional friction with the base 264 of the clip 250 and may assist the user in gripping the clip 250. The ridges 269 are on a smaller scale than the depression 267, and may be provided within the depression 267 as shown. The ridges 269 may provide a visual cue to the user. For example, in FIG. 40, the ridges 269 are arranged as arrows indicating that the clip 269 is configured to be moved in a certain direction.

Figure 44:
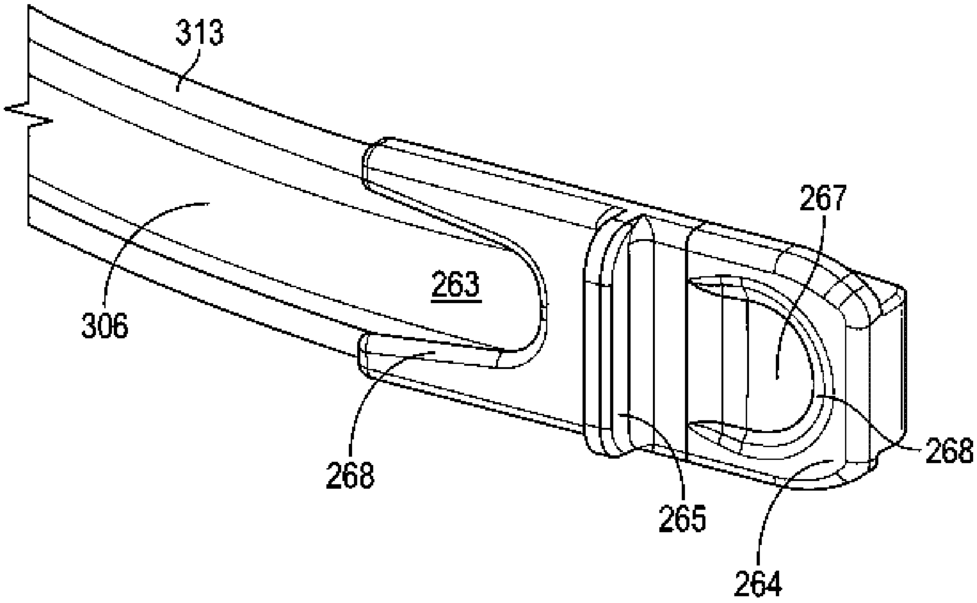
FIG. 44 is a perspective view of another modified version of the headgear clip of FIG. 9.

In some configurations, the headgear clip 250 can extend rearwardly along a forward portion of front strap portion 306 of the headgear 154. As shown in FIG. 44, the headgear clip 250 extends rearwardly from the projection 265 along the opposing edges 313 of the front strap portion 306, defining a contoured, C-shaped, recess 263 exposing an outer surface of the front strap portion 306. Like the depression 267, the recess 263 can define an inclined or perpendicular ridge or wall 268. The C-shaped recess 263 can act as a tactile feature to accommodate a finger or the thumb of the user when connecting and disconnecting the headgear clip 250, similar to depression 267.

Figure 43:
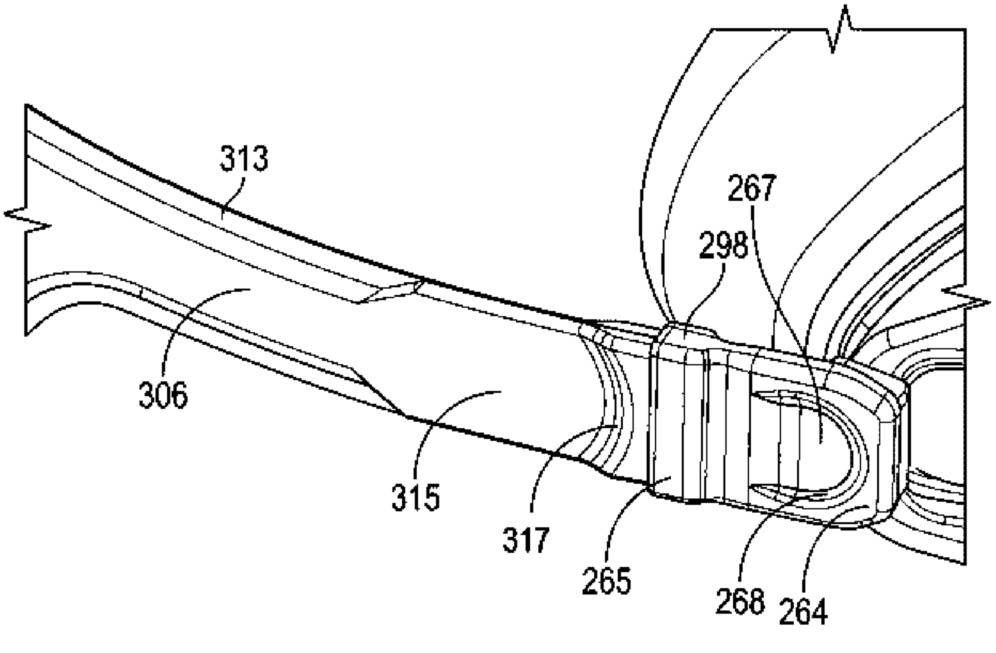
FIG. 43 is a perspective view of yet another modified version of the headgear clip of FIG. 9, also showing portions of headgear and a patient interface.

In some configurations, the plastic core within the front strap portion 306, described in further detail below, can vary in width along the front strap portion 306, in particular adjacent the clip 250. As illustrated in the configuration of FIG. 43, the plastic core of the front strap portion 306 has an area of increased width 315 adjacent the headgear clip 250. The area 315 may be substantially planar. The area 315 may extend outwardly beyond the edges 313 of the front strap portion 306. Having a wider plastic core adjacent the headgear clip 650 provides more area to accommodate the user's finger or thumb when connecting the headgear clip 250 with the frame 156. Similarly, the plastic core of the front strap portion 306 may be of varied thicknesses along the front strap portion 306, particularly adjacent the clip 250. As also illustrated in FIG. 43, the plastic core of the front strap portion increases in thickness toward the headgear clip 250. The portion of increased thickness may define an integral ledge 317. The ledge 317 provides a tactile feature that assists the user when gripping the front strap portion 306 and the headgear clip 250. As shown, the ledge 317 may be contoured to intuitively accommodate an index finger, for example. The headgear clip 250 may have an increased thickness at the location immediately adjacent the front strap portion 306. This may provide a projection 265, as described above. In other configurations, the rearward portion 298 of the clip 250 and the forward portion of the front strap portion 306 may be substantially flush with each other.

Figure 45:
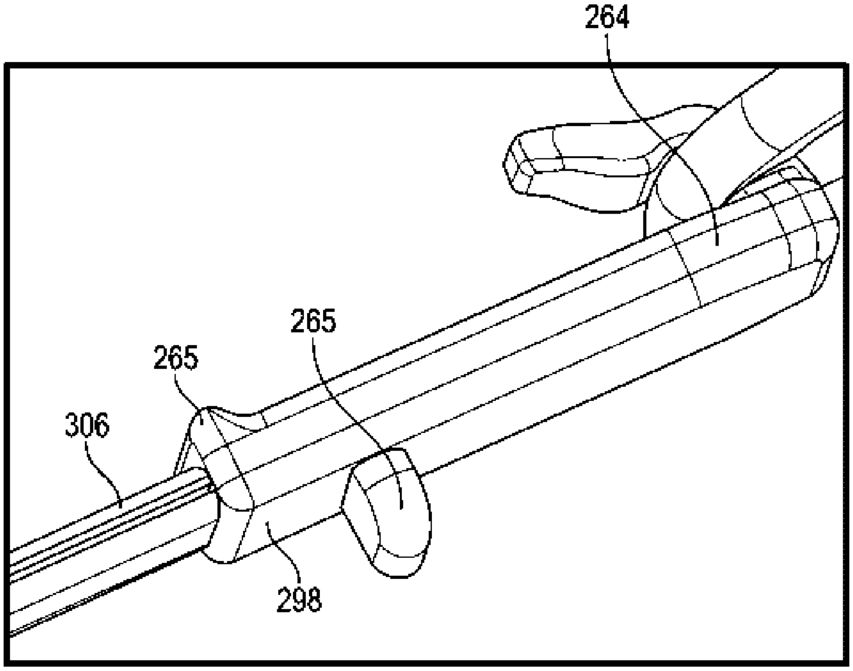
FIG. 45 is a perspective view of another modified version of the headgear clip of FIG. 9.

In some configurations, the clip 250 may alternatively, or additionally, be provided with a projection 265 from an inwards-facing side (that is, facing towards the user) of the base 264, as shown in FIG. 45.

Figure 41:
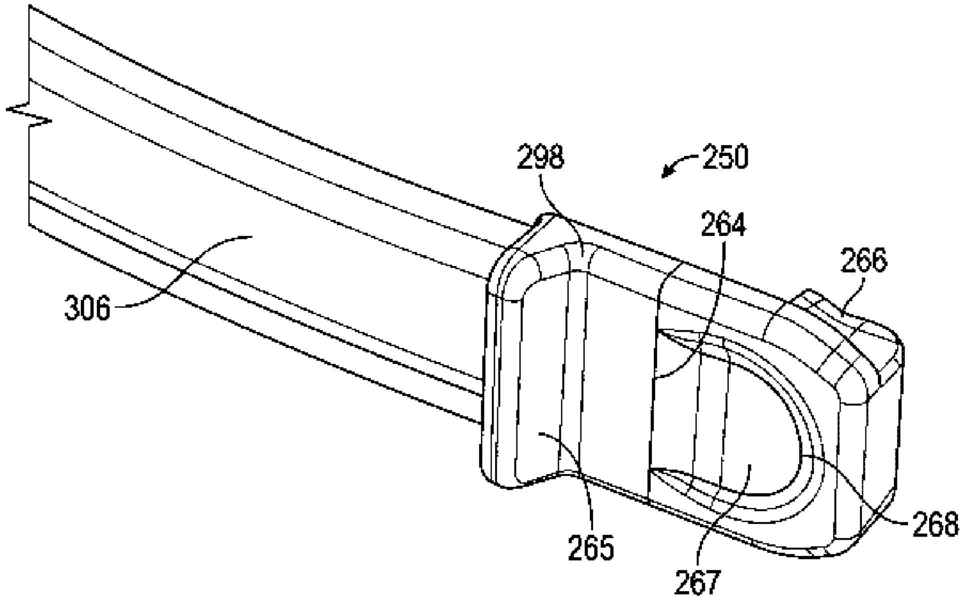
FIG. 41 is a perspective view of a modified version of the headgear clip of FIG. 9.
Figure 46:
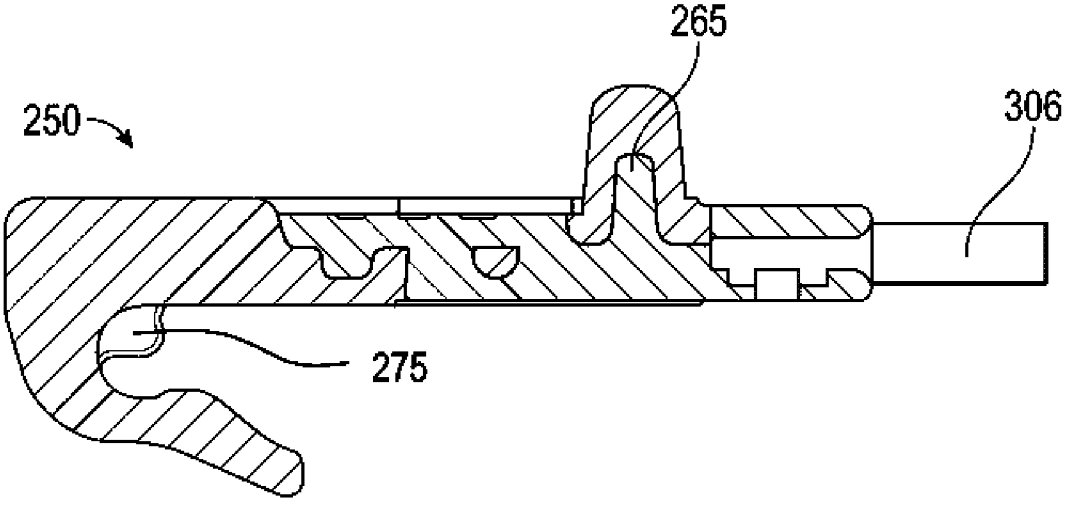
FIG. 46 is a perspective view of another modified version of the headgear clip of FIG. 9.

As shown in the configurations of FIGS. 41, 42 and 44-48, in some configurations the clip 250 may be formed from two different materials. The forward end of the clip 250, including the hook 266, is formed from a first material, and the rearward portion 298 is formed from a second material. The first material may be a resilient and relatively rigid thermoplastic material suitable for repeated engagement and disengagement with the post 260, such as polyoxymethylene (also known as acetal). The second material may be a resilient and relatively soft thermoplastic elastomeric material, such as the polyether block amide (PEBA) marketed under the name PEBAX® by the Arkema Group of Colombes, France. The second material may be overmolded to the first material and, optionally, a front strap portion 306 of the headgear 154 to secure the clip 250 to the front portion 300 of the headgear 154. The second material may be selected to provide a desired tactile feel and/or improved grip compared to the first material, while the first material may be selected to provide a positive and/or stable connection of the hook 266 with the frame 156. The first material may be the same material as used in the plastic core of the headgear 154, as described below. The projection 265 may be formed at least in part from the first, relatively rigid, material as shown in FIGS. 42, 45 and 48, for stability. Alternatively, or additionally, at least an outer portion of the projection 267 may be formed from the second, relatively soft, material as shown in FIGS. 41, 44 and 46 for improved grip or tactile feel. Referring in particular to FIG. 46, there is shown a cross-section of an example configuration of a clip 250 comprising first and second materials, wherein the second material is overmolded to, and mechanically interlocked with, both the first material and a front strap portion 306.

Figure 47:
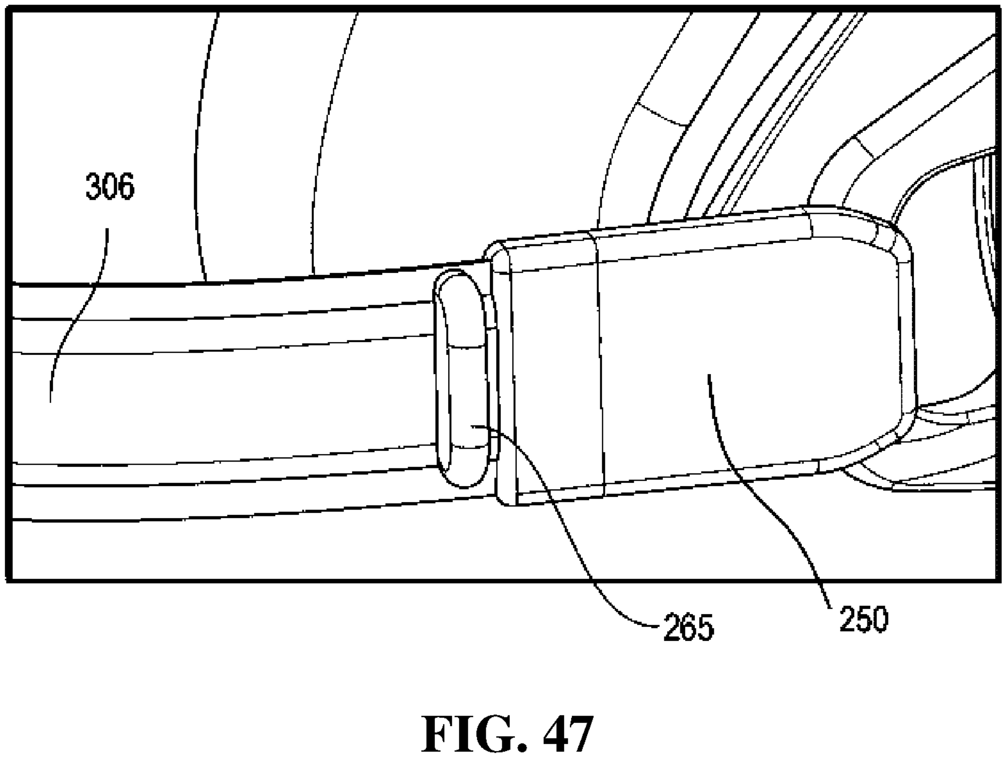
FIG. 47 is a perspective view of yet another modified version of the headgear clip of FIG. 9, also showing portions of headgear and a patient interface.

With reference to the further example configuration of FIG. 47, a projection 265 may alternatively, or additionally, be provided on the front strap 306. This may ensure sufficient clearance of the user's hands from the hook 266 and post 260, provide a more discrete and/or appealing aesthetic for the projection 265, and/or provide an improved tactile feel and/or grip to the projection 265. The projection 265 may be formed upon injection molding a plastic core inside a tubular knitted structure, as described in further detail below.

As described above, posts 260 and/or clips 250 on each side of the mask 152 may differ from each other in a way which reduces or eliminates the chance of improper connection between the headgear 154 and the frame 156. An example will now be described with reference to another example configuration of a patient interface assembly 150, and components thereof, as illustrated in FIGS. 48-52. Except as described herein and/or as apparent from the accompanying drawings, the patient interface assembly 150 of FIGS. 45-48 may be similar to that of FIG. 2. In particular, the patient interface assembly 150 includes a frame 156, a cushion module 160 and headgear 154. Each side of the frame 156 has an ear 252 that is associated with a headgear clip 250. The ears 252 extend laterally outward from a central portion 254 of the frame 156, which includes a frame connector 170 and an opening 256 that communicates with an interior of the connector portion 170 and receives the connection tube 164. The frame 156 includes a cylindrical frame connector 170 and an elliptical opening 256. The cooperating opening (not shown) of the housing 162 is circular.

In the configuration depicted in FIGS. 48-52, the connection arrangement 248 is modified to prevent or inhibit incorrect connection of the clips 250 to the posts 260. That is, the connection arrangement 248 may prevent or inhibit connection of the clips 250 in an incorrect orientation and/or to an incorrect side of the frame 156. In some configurations, the connection arrangement 248 may limit connections between the clips 250 and posts 260 to a single desired arrangement.

With reference to FIGS. 49 and 50, showing front and rear views of the frame 156, respectively, it can be seen that the posts 260 in this configuration each define a gap 261 along their respective longitudinal axes A. The illustrated posts 260 may be referred to as a split-post configuration comprising axially aligned first post portion 260*a* and second post portion 260*b*. The gap 261 is off-center along the longitudinal axis A of the posts 260. The split-posts 260 on opposing sides of the frame 156 are identical to each other. That is, the respective gaps 261 may be offset by the same distance from the center of the posts 260, and in the same direction.

Figure 51:
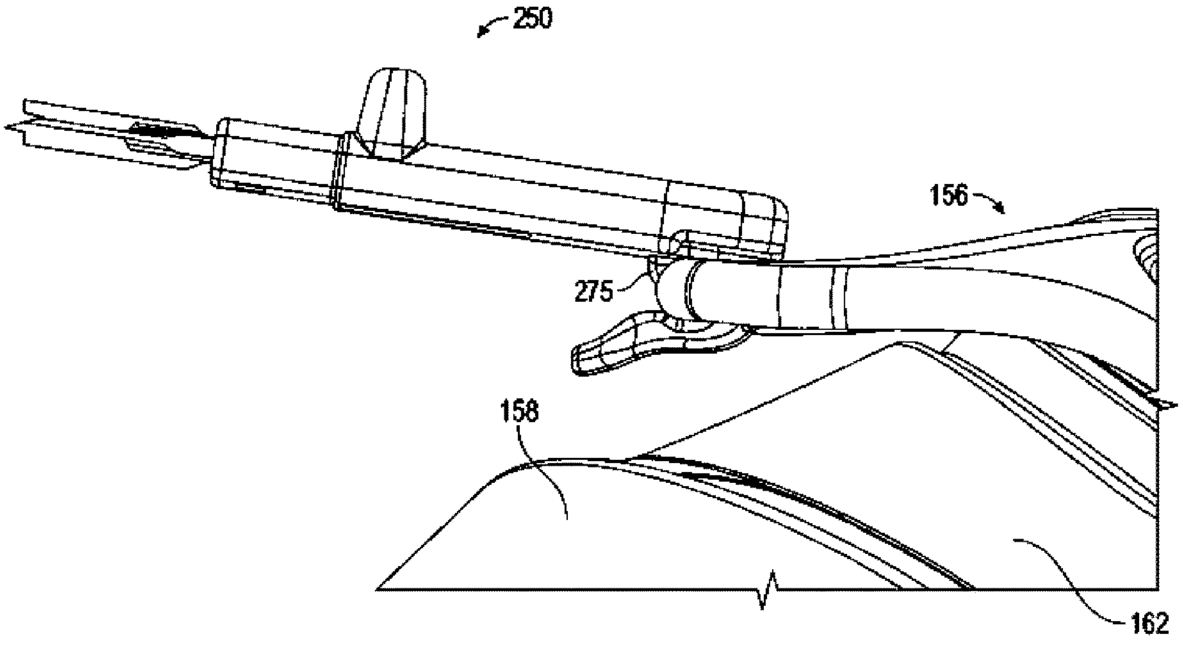
FIG. 51 is a detailed plan view of the connection arrangement of the patient interface assembly of FIG. 49.
Figure 52:
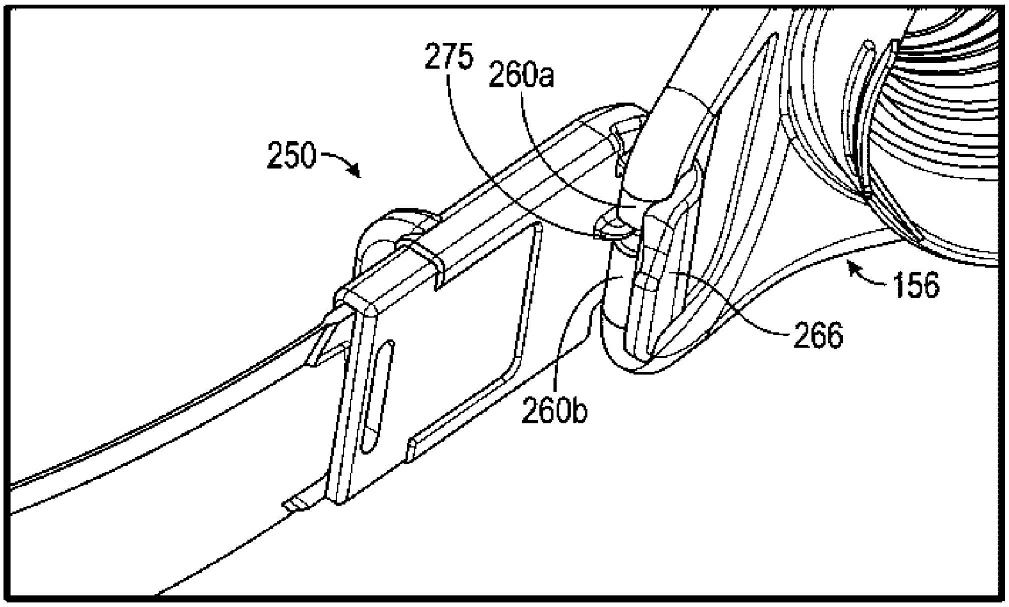
FIG. 52 is a perspective view of the connection arrangement of FIG. 51.

Referring to FIGS. 51 and 52, the clip 250 in this configuration includes a rib 275 which extends into the space 274 intended to receive a post 260. The rib 275 is also positioned off-center, and in particular is sized, shaped and positioned so as to be received by a gap 261 when the clip 250 is connected to one of the posts 260. The width of the rib 275 less than a length of the gap 261 in the axial direction A. The gap 261 and rib 275 do not inhibit rotation of the clip 250 about the axis A of the post 260 when the clip is correctly attached to the frame 156. Movement of the clip 250 in the direction of longitudinal axis A is limited by the size and/or shape of the narrowed portion 292 and the base or connecting portion of the hook 266, as described above. In some configurations, however, the rib 275 and gap 261 may alternatively, or additionally, limit movement of the clip 250 in the direction of longitudinal axis A when the clip 250 is connected to the frame 156. In some configurations, the rib 275 in conjunction with either or both of the first or second post portions 260*a*, 260*b* may be configured to provide for a snap-fit connection between the clip 250 and the frame 156, wherein the first and/or second post portions 260*a*, 260*b* may elastically deform and partially or fully recover upon engagement with the rib 275 as the hook 266 is engaged with the frame 156.

Referring still to the interface assembly 150 of FIGS. 48-52, the pair of clips 250 differ from each other such that one is configured to connect to a post 260 on one side of the frame 156, and the other clip 250 is configured to connect to the post 260 on the other side of the frame 156. The pair of clips 250 may be mirror images of each other. If an attempt is made to connect a clip 250 to an incorrect side of the frame 156, the rib 275 and gap 261 will not align, and the rib 275 will interfere with the post 260 to prevent or inhibit passage of the post 260 into the space 274. Upside-down connection of the clips 250 to posts 250 is prevented or inhibited by interference between narrowed portion 292 and height 270 of base 264.

In other configurations, an annular or part-annular rib 275 may be provided on the post 260, and a corresponding gap 261 or channel may be provided on the clip 250. In some configurations, a gap 261 and a rib 275 may be provided to the post 260 and clip 250 (or vice versa) on only one side of the patient interface assembly 150, ensuring that at least one of the clips 250, and thus the headgear 154 as a whole, cannot be incorrectly connected to the frame 156. In some configurations, the clips 250 may be identical to each other and the posts 260 one each side of the frame 156 may differ.

Headgear

FIGS. 2, 13-16 and 22-27 illustrate an example of the headgear 154 described above. The headgear 154 is described below with reference to FIGS. 2, 13-16 and 22-27. In the illustrated arrangement, the headgear 154 has a front portion 300 and a rear portion 302. The front portion 300 is configured to connect to the mask 152 and extends between the mask 152 and the rear portion 302. The rear portion 302 is configured to engage a side and/or rearward portion of the user's head. The illustrated front portion 300 includes a front strap or strap arrangement 304 that connects to the mask 152 via the clip 250 on each side of the interface assembly 150 or head of the user. In the illustrated arrangement, the front strap arrangements 304 on each side of the interface assembly 150 are separate from one another and separately connect to the mask 152. The front strap arrangements 304 can be mirror images of one another.

In alternative configurations, the front strap arrangement 304 of one side can be permanently connected to the mask 152 or can be connected in a more complicated and harder-to-remove manner than the clip 250 located on the opposite side of the mask 152 such that the mask assembly 150 is removed using the clip 250. In an alternative arrangement, the front strap arrangement 304 of one side of the headgear 154 can be coupled to the mask 152 and the front strap arrangement 304 of the other side of the headgear 154 can be coupled to the front strap arrangement 304 of the first side.

Each of the illustrated front strap arrangement 304 includes a single front strap portion 306 that connects to the mask 152 via the clip 250. The front strap arrangement 304 bifurcates to define an upper strap portion 308 and a lower strap portion 310 that extend towards or are at least partially located above and below a level of the user's ear, respectively. The front strap portion 306 extends from the mask 152 across the user's cheek to the bifurcation point. In the illustrated arrangement, the front strap portion 306 extends in a slightly upward direction from the mask end to the bifurcation end. The upper strap portion 308 continues the curvature of the front strap portion 306 and extends toward or to a location above the user's ear. In some configurations, the end of the upper strap portion 308 can be located directly above or above the line of and slightly forward of the user's ear. An end portion of the upper strap portion 308 can curve in a downward direction for connection with the rear portion 302 of the headgear 154. The lower strap portion 310 extends from the bifurcation end of the front strap portion 306 in a downward direction to a location on the user's jaw at a height below the user's ear. The end of the lower strap portion 310 can be located lower and forward of the user's ear. The end portion of the lower strap portion 310 can curve in an upward direction for connection with the rear portion 302 of the headgear 154.

In some configurations, the front strap portion 306, the upper strap portion 308 and the lower strap portion 310 of the front strap arrangement 304 can be constructed as a unitary structure. In some configurations, the front strap arrangement 304 can be constructed as a molded composite structure having at least one fabric layer and at least one plastic layer permanently connected to one another. In the illustrated arrangement, the front strap arrangement 304 is a molded composite structure having two fabric layers with a plastic core located between the fabric layers. The front strap arrangement 304 can be formed as a unitary structure by the application of molten plastic into the space between the fabric layers within a mold and allowing the molten plastic to harden to form the plastic core in the shape of the mold cavity. The fabric layers can be separate from one another and joined via the plastic core or can be connected (e.g., a tubular structure that surrounds the plastic core).

A portion or an entirety of the front strap arrangement 304 can be semi-rigid. The term "semi-rigid" in this context is intended to mean that the relevant structure is flexible and at least somewhat resilient, but with little or no extensibility. In the illustrated arrangement, any one, any combination or all of the front strap portion 306, upper strap portion 308 and the lower strap portion 310 can be semi-rigid. As used herein, semi-rigid means that the semi-rigid portion of the headgear 154 can generally retain its shape under its own weight but has some flexibility to enable the semi-rigid portion to bend around a user's head. In some configurations, the semi-rigid portion of the headgear 154 is more rigid in one direction and is less rigid in a second direction. For example, the semi-rigid portion of the headgear 154 can be substantially rigid in a vertical direction or along the face of the user and can be relatively flexible in a horizontal direction or toward-and-away from the user.

The front strap arrangement 304 can be configured for connection to the rear portion 302 of the headgear 154. In some configurations, the ends of the upper strap portion 308 and the lower strap portion 310 can include loops 312 configured to receive strap portions of the rear portion 302 of the headgear 154. In the illustrated arrangement, the loops 312 can be plastic loops that are overmolded onto the end of the upper strap portion 308 and the lower strap portion 310. In other arrangements, the loops 312 could be formed by the plastic core material of the front strap arrangement 304 or the loops 312 could be formed separately from the front strap arrangement 304 and attached thereto.

In some configurations, the headgear 154 includes a top strap arrangement 314 that passes over the user's head from one side to the other side of the headgear 154. In the illustrated arrangement, the top strap arrangement 314 connects to a rearward end portion of the upper strap portion 308 of the front strap arrangement 304 on each side of the headgear 154. In particular, the top strap arrangement 314 can connect to the uppermost portion of the upper strap portion 308 before the upper strap portion 308 begins to curve downwardly toward the rear portion 302 of the headgear 154. In the illustrated arrangement, each end of the top strap arrangement 314 is connected to the upper strap portion 308 by an overmolded connector 316. The overmolded connector 316 can molded onto a portion of each of the top strap arrangement 314 and the upper strap portion 308 to join the two components. Alternatively, the overmolded connector 316 can be joined to one of the components by overmolding and can define a connecting structure (e.g., a loop) to which the other component can be connected. For example, the overmolded connector 316 can be overmolded onto the upper strap portion 308 and can define a loop to which the top strap arrangement 314 can be coupled.

In some configurations, the top strap arrangement 314 comprises a first strap portion 320 and a second strap portion 322 (FIG. 13) that can connect to one another. The first strap portion 320 and the second strap portion 322 can be connectable to one another in an adjustable manner, such as with a buckle, post-and-hole structure 324 or a similar connector that sits generally at the top of the user's head. In the illustrated arrangement, the free end of the second strap portion 322 includes a guide loop through which the first strap portion 320 can pass. The first strap portion 320 can be sized for a relatively tight fit with the guide loop to maintain a loose connection between the first strap portion 320 and the second strap portion 322 when the straps 320, 322 are not connected by the post-and-hole structure 324. Such an arrangement avoids unintentional separation of the straps 320, 322 when the user is adjusting the top strap arrangement 314 for ease of use during the adjustment process. In some configurations, an end of the second strap portion 322 can be slightly larger (e.g., in width and/or thickness) than the opening of the guide loop to create an interference fit between the strap portion 322 and the guide loop to further reduce the likelihood of unintentional separation.

Figure 22:
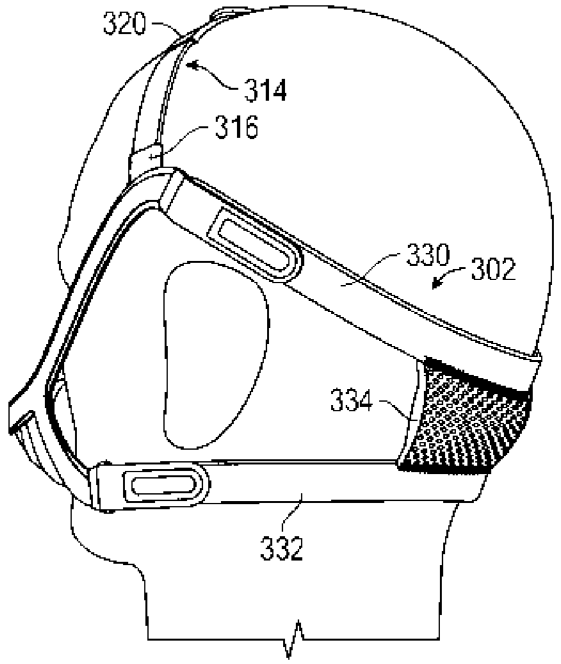
FIG. 22 is a rear perspective view of the headgear arrangement of FIG. 2.
Figure 23:
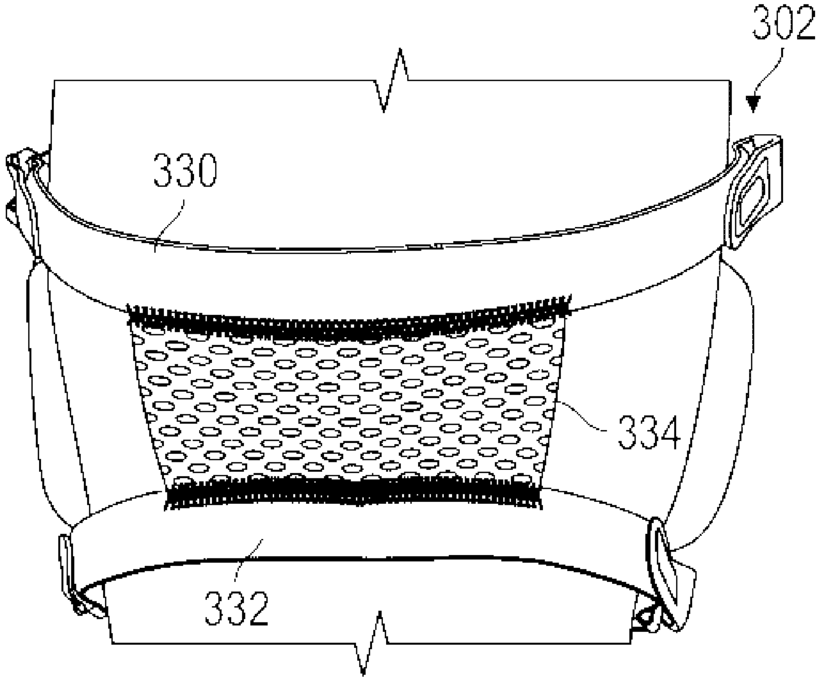
FIG. 23 is a rear view of a rear portion of the headgear arrangement of FIG. 2.
Figure 24:
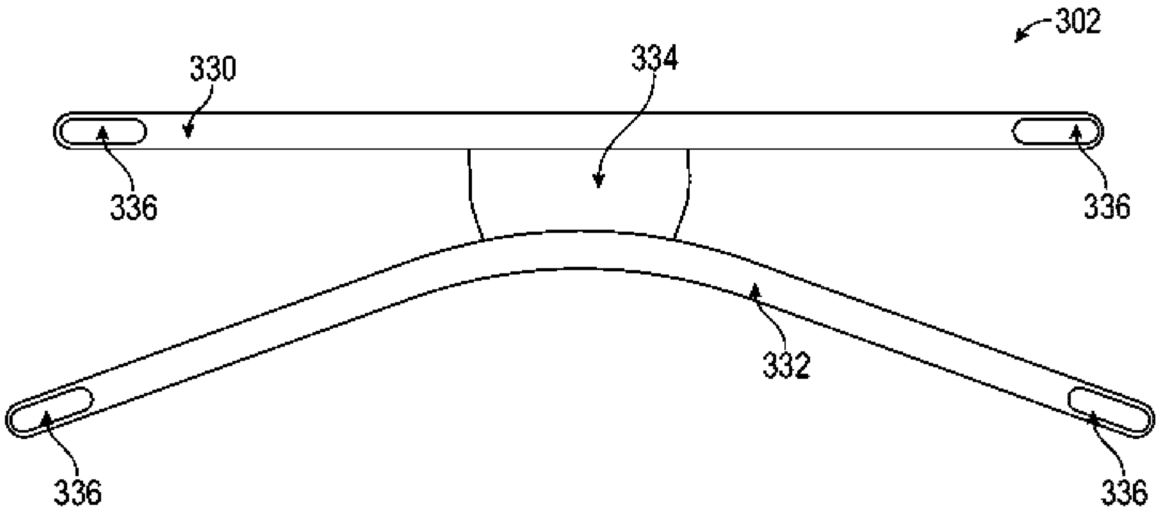
FIG. 24 is a plan view of the rear portion of the headgear of FIG. 23 in a relaxed or laid-flat configuration.

The illustrated rear portion 302 of the headgear 154 includes a first or upper strap 330 and a second or lower strap 332. The upper strap 330 and the lower strap 332 are spaced apart from one another by a panel 334. Each of the upper strap 330 and the lower strap 332 are configured to extend around the back of the user's head and connect to the front strap arrangements 304 of the front portion 300 of the headgear 154. In particular, opposing ends of the upper strap 330 connect to the upper strap portions 308 of respective ones of the front strap arrangements 304 on opposing sides of the user's face. Similarly, opposing ends of the lower strap 332 connect to the lower strap portions 310 of respective ones of the front strap arrangements 304. As illustrated in FIG. 22 for example, the upper strap 330 extends in a downward direction from each end towards or to the panel 334 or a vertical centerline of the rear portion 302. In other words, the end or loop 312 of the upper strap portion 308 is located at a level above an upper edge of a portion or an entirety of the panel 334. In some configurations, the lower strap 332 can extend in an upward direction from each end towards or to the panel 334 or a vertical centerline of the rear portion 302.

Each of the upper strap 330 and the lower strap 332 can be constructed from a composite material comprising a pair of fabric layers on opposing sides of a foam layer. In particular, the straps 330, 332 can comprise a three-layer construction, which includes layers formed of Lycra, foam and UBL (unbroken loop) materials. The UBL material can form the outer layer of each of the straps 330, 332. Each end of each of the upper strap 330 and the lower strap 332 terminates with a tab 336 that can form a hook portion of a hook and loop fastener. The tabs 336 can be ultrasonically welded onto the ends of the straps 330, 332 or connected in another suitable fashion. The UBL material provides a loop surface to which the hook tabs 336 can connect. The ends of the straps 330, 332 can pass through the loops 312 of the front portion 300 of the headgear 154 and double back onto themselves. The hook tabs 336 can connect at any point along the length of the straps 330, 332 to provide for size adjustment of the headgear 154.

Figure 25:
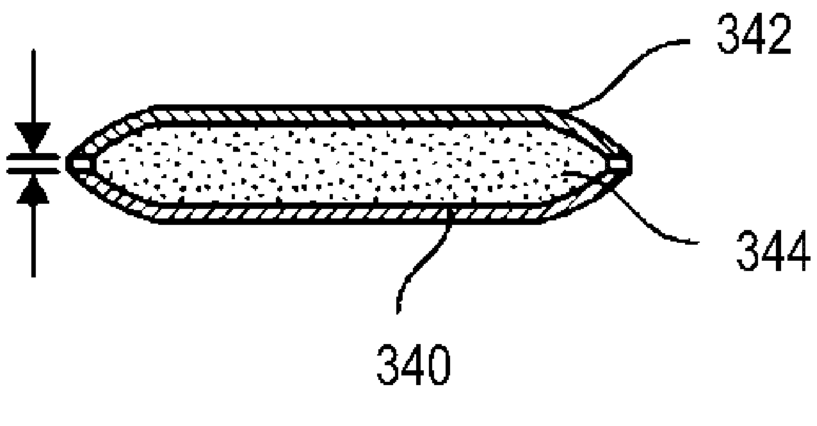
FIG. 25 is a sectional view of a panel of the rear portion of the headgear of FIG. 23.

In some configurations, the panel 334 can be constructed in whole or in part from a spacer fabric, which is a composite material including two spaced-apart cover fabrics connected with filaments positioned between the cover layers. With reference to FIG. 25, the spacer fabric of the panel 334 is shown in cross-section. The spacer fabric can include a first fabric layer 340, a second fabric layer 342 and a central spacer or connecting layer 344. In some configurations, the first fabric layer 340 is a lycra or similar material and the second fabric layer 342 is a UBL or similar material. The spacer layer 344 can be constructed from any suitable yarn or filament material(s), such as polyester. A gap may be formed between the first and second fabric layers 340, 342 at an outer edge of the panel 334, as shown in FIG. 25. In one configuration, the gap between the first and second fabric layers 340, 342 is at least 0.1 mm.

In the illustrated arrangement, the upper strap 330 and the lower strap 332 are continuous from one end to the other and the panel 334 extends between a bottom edge of the upper strap 330 and a top edge of the lower strap 332. Such an arrangement provides a greater range of adjustment to the rear portion 302 because the ends of the straps 330, 332 can be connected to a portion of the strap 330, 332 that overlaps with the panel 334. However, in other arrangements, the upper and/or lower straps 330, 332 could be provided in two segments, each of which extend from a side edge of the panel 334. In other words, the panel 334 could interrupt the portions of the strap(s) 330, 332. Such an arrangement can limit the adjustability of the rear portion 302 because the ends of the straps 330, 332 can only be connected to the strap 330, 332 up to the edge of the panel 334.

In the illustrated arrangement, in a relaxed or laid-flat orientation, the upper strap 330 is linear or straight and the lower strap 332 is curved such that the ends are lower than the center portion. Specifically, the lower strap 332 has a curved central section and linear sections extending either side of the central section. In other arrangements, the upper strap 330 could be curved and the lower strap 332 could be straight. In yet other arrangements, both straps 330, 332 could be straight or curved.

In some configurations, the straps 330, 332 have differing levels of stretch. In other words, the elongation for a given applied force will vary between the straps 330, 332. In some configurations, the bottom strap 332 has greater stretch or elongation than the top strap 330. Greater stretch in the bottom strap 332 can allow the user to move his or her chin more easily or comfortably and/or can reduce the pressure of the strap 332 on the user's skin. However, in other arrangements, the straps 330, 332 could have the same stretch characteristics or the upper strap 330 could be more stretchable than the lower strap 332.

In some configurations, the straps 330, 332 edges are radio-frequency, dielectric or high-frequency welded (RF welded), pressed and cut to create a rounded edge to the straps 330, 332 that increased comfort for the user. The RF welding process also secures the materials of the composite fabric together to inhibit or prevent delamination.

Figure 26:
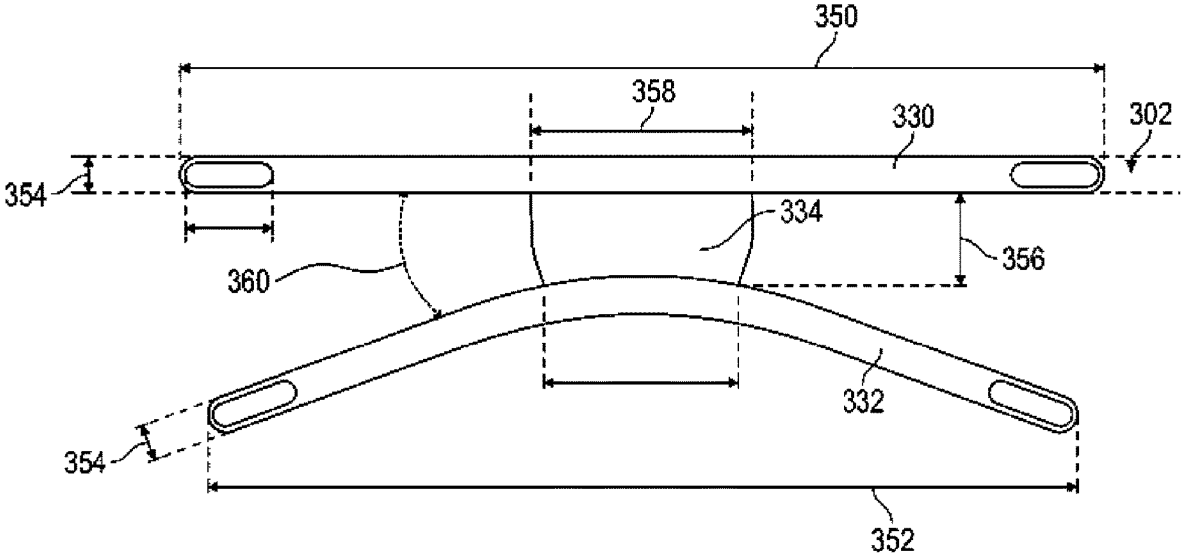
FIG. 26 is the plan view of the rear portion of the headgear of FIG. 24 illustrated certain dimensions of the rear portion.

With reference to FIG. 26, the rear portion 302 of the headgear 154 can be provided in multiple sizes. In some configurations, the rear portion 302 of the headgear 154 can provide for an entirety of the circumferential adjustment of the headgear 154 (although the top strap arrangement 314 can provide for some depth adjustment of the headgear 154). Thus, the front portion 300 of the headgear 154 can be provided in a single size. In some configurations, the rear portion 302 is provided in two sizes—small and large. In some such configurations, the only difference between the sizes is the length of one or both of the straps 330, 332. In the illustrated arrangement, a length 350 of the upper strap 330 in a size small is between about 340-400 mm or about 370 mm. In a size large, the length 350 can be between about 400-460 mm or about 430 mm. A length 352 of the lower strap 332 (measured as a linear end-to-end distance with the lower strap 332 in its relaxed or natural curved state) in the size small is between about 300 mm-400 mm, about 325 mm-375 mm, or about 350 mm (e.g., 348 mm or 348.14 mm). In the size large, the length 352 is between about 400 mm-500 mm, about 450 mm-475 mm, or about 470 mm (e.g., 470.30 mm). The straps 330, 332 can have a width 354 of between about 10-20 mm, about 12-16 mm, or about 14 mm or 15 mm.

In some configurations, the panel 334 can be the same size in multiple sizes of the rear portion 302. For example, the panel 334 can have a maximum height 356 of between about 30-50 mm, about 35-40 mm, or about 38 mm (e.g., 38.32 mm). The panel 334 can have a maximum width 358 of between about 50 mm-150 mm, about 75 mm-125 mm, or about 90 mm or 100 mm. In some configurations, the panel 334 can taper from the maximum width 358 at an upper and/or a lower end. In the illustrated arrangement, the panel 334 tapers at a lower end by about 10-15 percent of the maximum width 358.

In some configurations, the straps 330, 332 can define an angle 360 between them. As noted above, in some configurations, the upper strap 330 can be straight and the lower strap 332 can be curved. Accordingly, the angle 360 can be defined by the lower strap 332. In other arrangements, the upper strap 330 could be curved and the angle 360 defined by the upper strap 330 or both straps 330, 332 could be curved and the angle 360 defined by both of the straps 330, 332. In some configurations, the angle 360 is less than about 30 degrees. In some configurations, the angle 360 is between about 10-30 degrees, about 15-25 degrees or about 20 degrees.

Figure 27A:
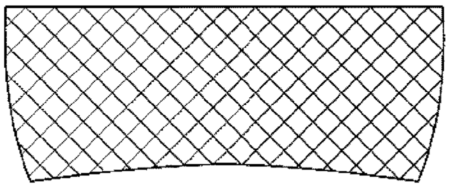
FIG. 27A-27E illustrate a method of making and a resulting structure of the panel and the rear portion of the headgear of FIG. 23.
Figure 27B:
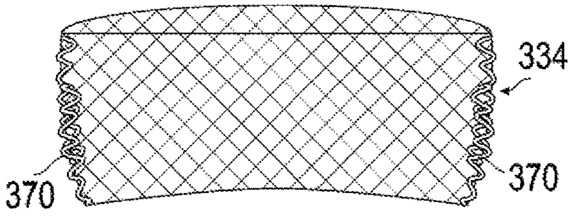
Figure 27C:
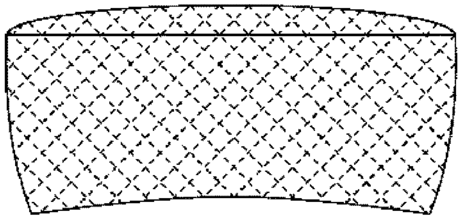
Figure 27D:
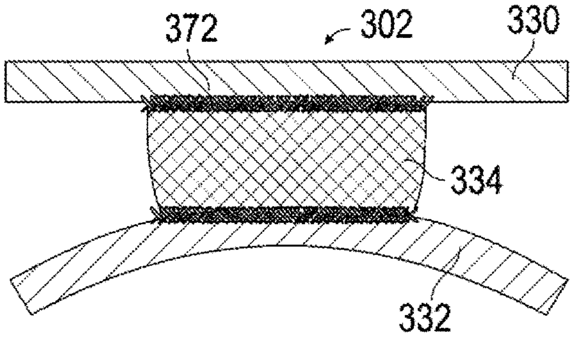
Figure 27E:
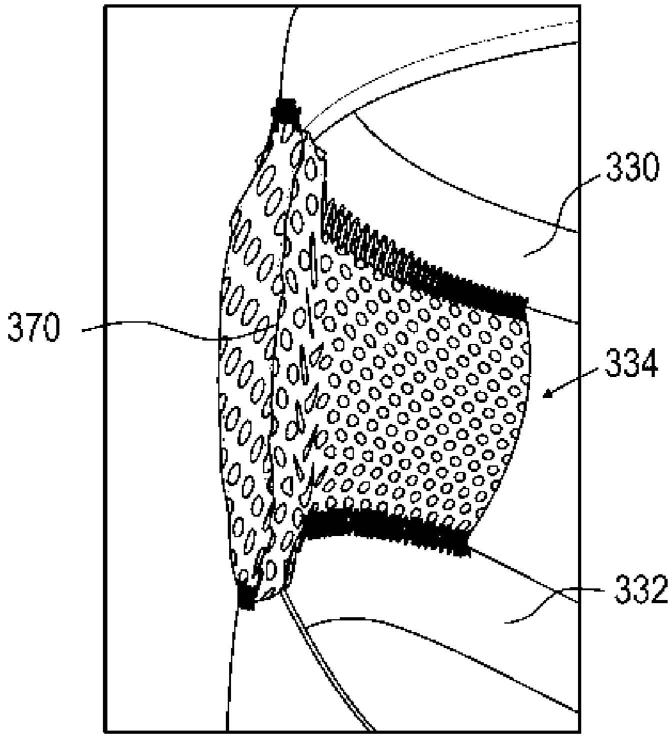

With reference to FIG. 27A-E, an example process or method for constructing the panel 334 and rear portion 302 of the headgear 154 is illustrated. With reference to FIG. 27A, two separate layers of spacer fabric (or other suitable fabric) are cut or otherwise formed to the general shape of the panel 334. With reference to FIG. 27B, the two layers of spacer fabric are secured together along the side edges. In the illustrated arrangement, the layers are secured together by sewing to create a stitched joint or stitched connection 370. However, other suitable connection arrangements or methods could also be used. With reference to FIG. 27C, the now joined layers of spacer fabric are inverted or turned inside-out to hide the stitched connection 370 and protect the stitched connection 370 from snagging or unravelling from external forces. With reference to FIG. 27D, the upper and lower edges of the panel 334 are connected to the respective one of the upper and lower straps 330, 332. In the illustrated arrangement, the upper and lower edges of the panel 334 are connected by sewing to create a stitched connection 372. However, other suitable connection arrangements or methods could be used. The previously open upper and lower edges of the two spacer fabric layers are closed in the process. The sewn or stitched connection 372 advantageously reduces or prevents tension in the connection 372 and permits the panel 334 and/or straps 330, 332 to stretch during use. FIG. 27E illustrates the clean joint that is exposed when the sewn spacer fabric panels are inverted, as described with respect to FIG. 27C.

Advantageously, the spacer fabric panel 334 and, in particular, the multi-layered spacer fabric panel 334 provides a lighter and/or more breathable panel 334 in comparison to a panel constructed from conventional materials, such as a foam composite (e.g., Breath-o-Prene®). In addition, the present spacer fabric panel 334 provides cushioning and support to the back of the user's head and can be less bulky and/or intrusive for the user compared to a panel constructed from conventional materials. The breathability of the spacer fabric can reduce the likelihood of the user getting too warm and can reduce or prevent sweating. The spacer fabric panel 334 can be more compressible than a comparable foam composite material panel, which can allow the spacer fabric panel 334 to compress to a smaller or minimal thickness in response to the weight of the user's head. With such an arrangement, the user may be less likely to feel the panel 334 when lying on it, especially when lying on his or her side, due to the compressibility and reduced thickness under load in comparison to a foam composite material panel.

Figure 28:
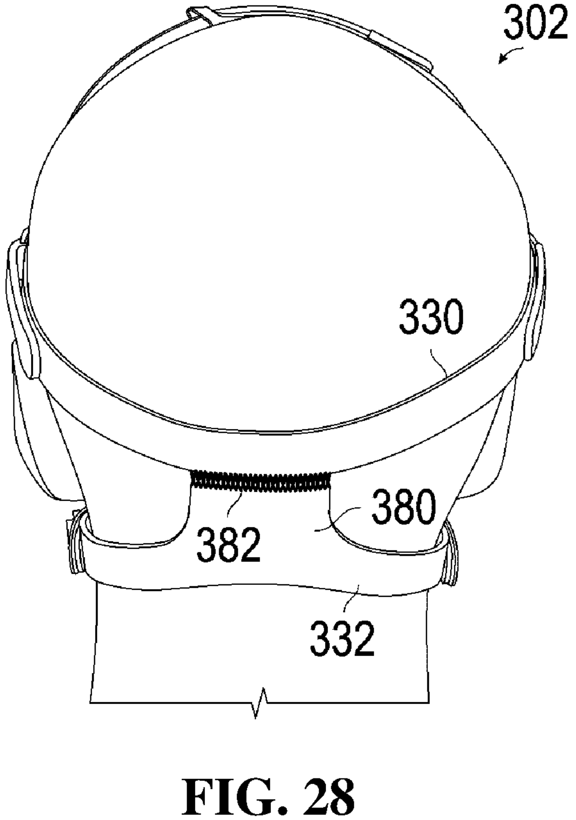
FIG. 28 is a rear view of an alternative rear portion of the headgear.
Figure 29:
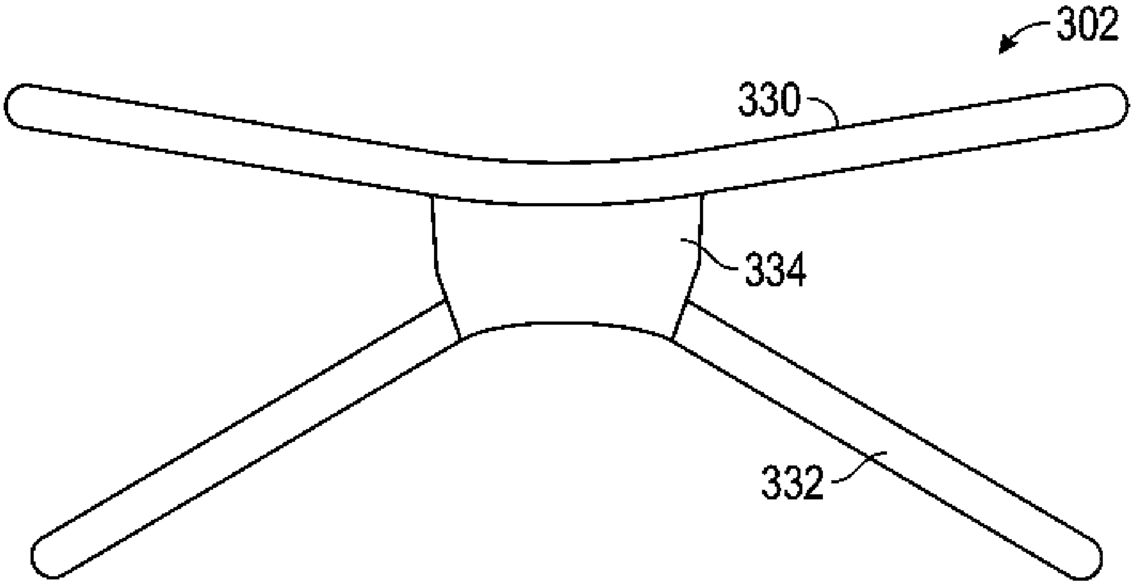
FIG. 29 is a plan view of an alternative rear portion of the headgear having a knitted panel.
Figure 30:
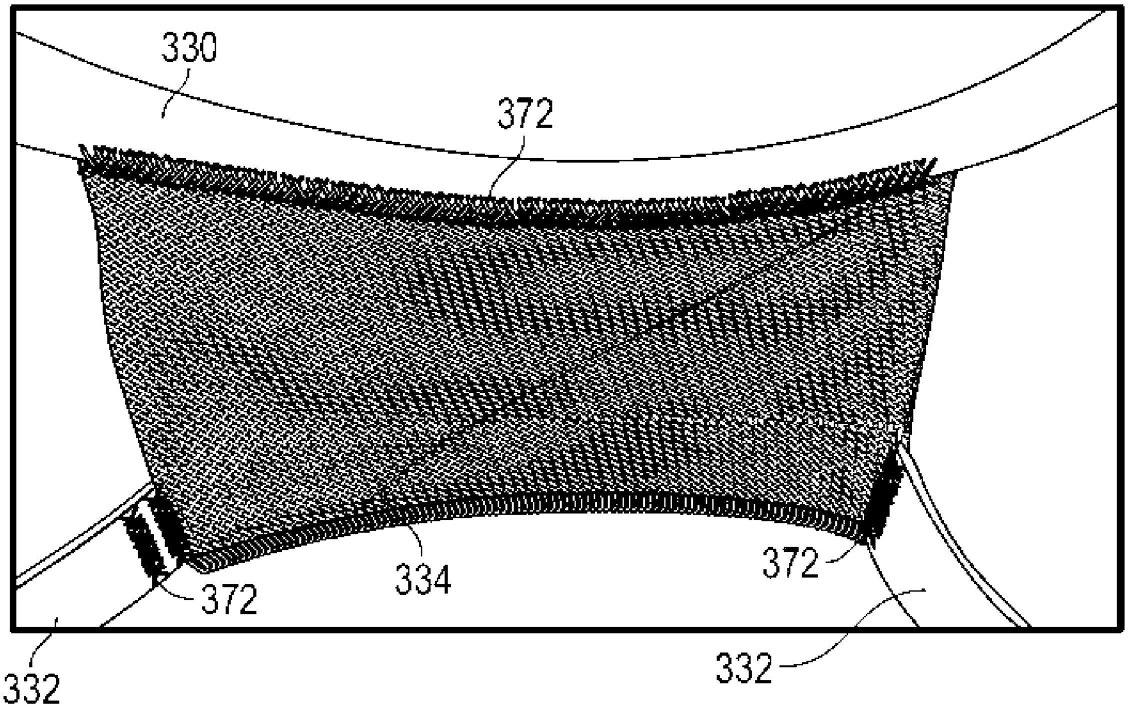
FIG. 30 is a plan view of a portion of the rear portion of FIG. 29 showing the knitted panel.
Figure 31:
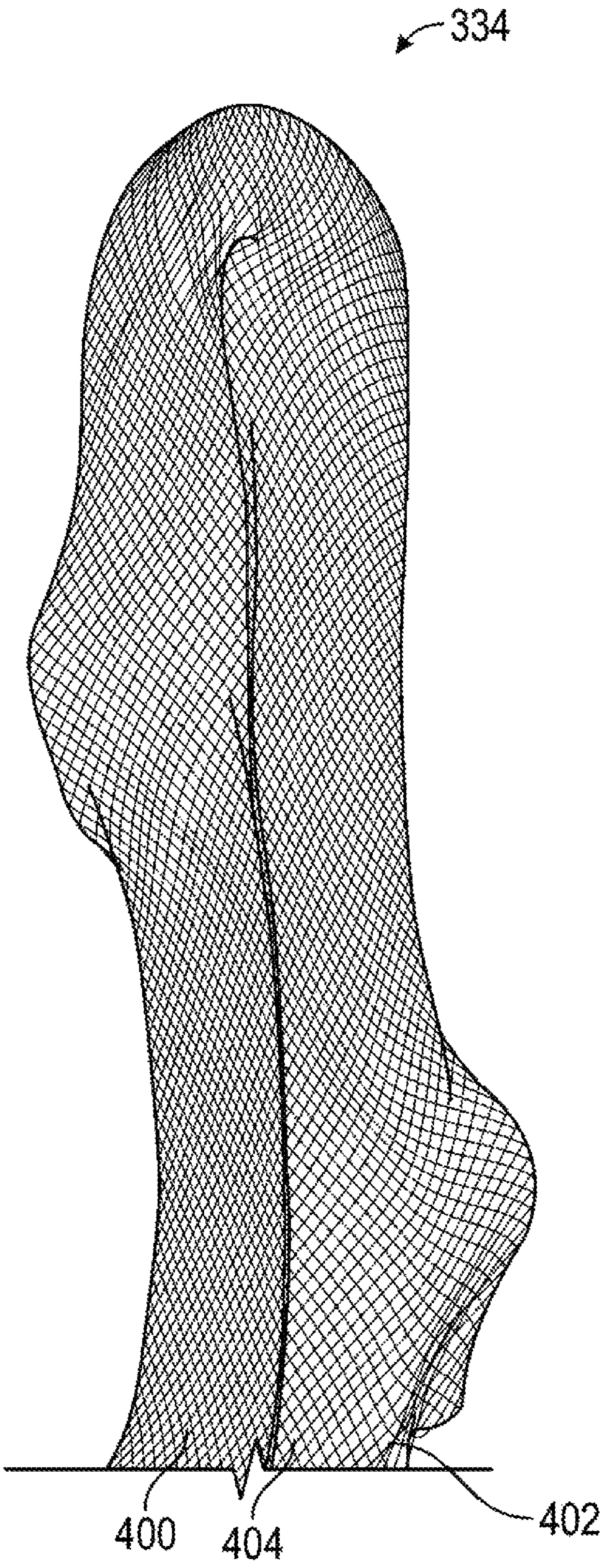
FIG. 31 is a side view of the knitted panel of FIG. 30.

FIG. 28 illustrates a modification of the rear portion 302 of the headgear 154, which can be the same as or similar to other rear portions 302 described herein except as described below. The rear portion 302 of FIG. 28 omits the spacer fabric panel 334 and instead forms a panel portion 380 utilizing a unitary structure of one or both of the straps 330, 332. In the illustrated arrangement, the lower strap 332 defines the panel portion 380, which extends upwardly from the strap portion of the lower strap 332 to space-apart the upper strap 330 and the lower strap 332 in a manner similar to the panel 334 of other embodiments described herein. The panel portion 380 can be coupled to a bottom edge of the upper strap 330 by a suitable connection, such as a stitched connection 382. In other arrangements, the panel portion 380 could be defined by the upper strap 330 or the panel portion 380 could be defined by a combination of protruding portions of each of the straps 330, 332. In some configurations, the upper strap 330 and the lower strap 332 could have the same or similar levels of stretch, which could be similar to the stretch of the lower strap 332 discussed above.

Knitted Rear Panel

FIGS. 29-32 illustrate another example of a rear portion 302 of the headgear 154, which can be the same as or similar to other rear portions 302 described herein except as described below. In the arrangement of FIG. 29-32, the panel 334 is constructed in whole or in part by a knitted material. In addition, the upper strap 330 is a single, continuous piece, but the lower strap 332 is interrupted by the panel 334. Such an arrangement can allow the knitted material of the panel 334 to define a lower edge of a central portion of the rear portion 302 of the headgear 154. However, in other arrangements, the lower strap 332 could be a single, continuous piece. In other arrangements, the upper strap 330 could be interrupted by the panel 334.

In some configurations, the panel 334 is formed by a knitting process separately from the straps 330, 332 and is then connected to the straps 330, 332 in a separate process step(s) in a manner similar to that described herein with respect to the spacer fabric panel 334. Once the knitted panel 334 is formed, the panel 334 can be joined to the upper strap 330 and lower strap portions 332 by a suitable connection arrangement or process. For example, in the illustrated arrangement, the knitted panel 334 is connected to the upper strap 330 and the lower strap portions 332 by a sewing process to create a stitched connection 372. In particular, the knitted panel 334 is connected to the upper strap 330 by the stitched connection 372 along an entirety of the upper edge of the knitted panel 334. The lower strap portions 332 are each connected to opposed side edges of the knitted panel 334 by the stitched connection 372. The lower strap portions 332 are connected at bottom corners of the knitted panel 334 such that a lower edge of the lower strap portions 332 are aligned with a lower edge of the knitted panel 334 at a junction therebetween. Similar to the arrangement described above, the lower strap portions 332 extend at a downward angle from the knitted panel 334.

In some configurations, the knitted panel 334 is created by a knitting process that constructs the panel 334 in a vertical direction as oriented in the drawings and in use with the user's head in a upright position. With such an arrangement, a stretch of the knitted panel 334 is greater in the horizontal direction than in the vertical direction. That is, the elongation of the knitted panel 334 in the horizontal direction is greater than the elongation in the vertical direction for a given applied force. As a result, the greater horizontal stretch can allow the rear portion 302 and the associated headgear 154 to fit a larger range of head sizes. In some configurations, the knitting process starts at the bottom of the panel 334 or first creates the bottom of the panel 334 and progresses toward the top of the panel 334. However, in other configurations, this direction could be reversed.

Figure 32:
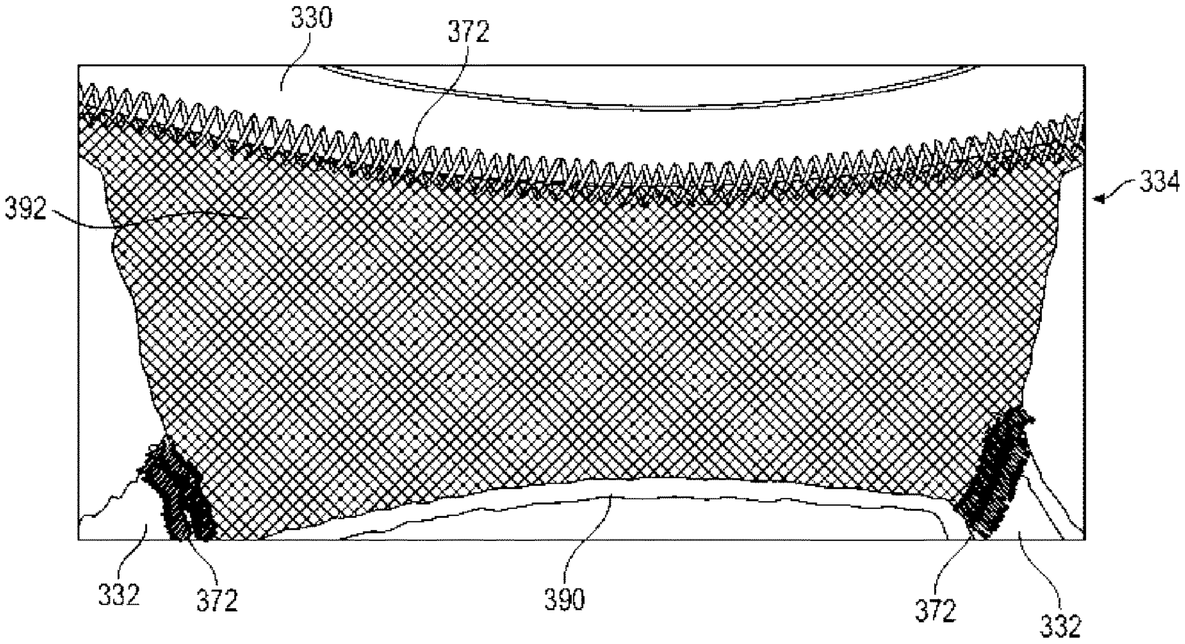
FIG. 32 is a plan view of the knitted panel of FIG. 30.
Figures 1, 2, 32:
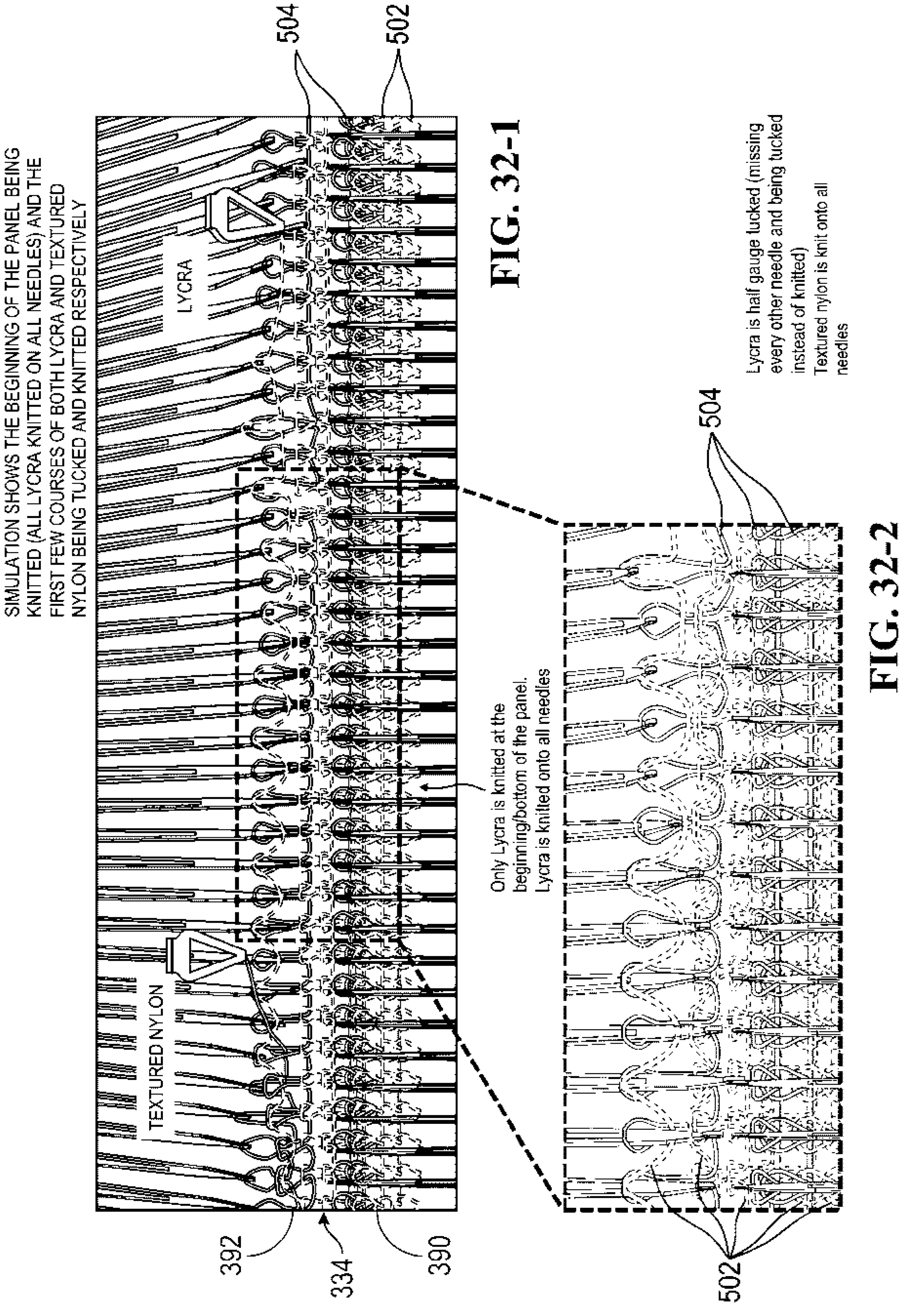

With reference to FIG. 32, different portions of the panel 334 can be constructed with different materials or different combinations of materials. For example, in the illustrated arrangement, the bottom-most portion 390 of the knitted panel 334 is created using only a first material, such as a first yarn or filament type 502. In some configurations, the first material comprises an elastane material (e.g., Lycra). In some configurations, the first material is a nylon-wrapped elastane. As the knitting process progresses upwardly or creates a relative upper portion 392 of the knitted panel 334 above the bottom-most portion 390, a second material, such as a second yarn or filament type 504, is introduced. In some configurations, the second material is or comprises nylon (e.g., textured nylon). The second material can be used exclusively in the upper portion 392 or can be combined with the first material and/or other materials. The use of two or more materials in the panel 334 provides advantageous or desirable properties, as discussed further below. However, the use of a single material in the bottom-most portion 390 results in a less bulky structure, which can increase comfort for the user compared to a bottom-most portion 390 incorporating multiple materials.

A combination of the first and second materials, such as the materials comprising elastane and nylon described above, provides the overall knitted panel 334 with desirable properties. For example, the elastane material is less bulky than the nylon material and provides good recovery. The nylon material is non-elastic with more bulk, thickness and depth than the elastane material.

In some configurations, the knitted panel 334 is knitted to have multiple layers. For example, with reference to FIG. 31, the knitted panel 334 can comprise a first layer 400 and a second layer 402. The first layer 400 can be an interior layer that faces toward or is positioned adjacent the user. The second layer 402 can be an exterior layer than faces away from the user. The first layer 400 can be positioned between the second layer 402 and the user. The first layer 400 and the second layer 402 can be joined along their side edges. In some configurations, the first layer 400 and the second layer 402 are created as a unitary structure during the knitting process. In some configurations, the first layer 400 and the second layer 402 could define a tubular structure. However, in the illustrated arrangement, the first layer 400 and the second layer 402 are connected by interlock stitches 404, which can be created during the knitting process. Alternatively, the interlock stitches 404 could be created by a process separate from the knitting process (e.g., by subsequent sewing). Furthermore, the first layer 400 and the second layer 402 could be knitted separately and connected by a suitable connection arrangement or process, such as sewing.

FIGS. 32-1 and 32-2 illustrate a process for creating the knitted panel 334 and a resulting structure of the knitted panel 334. The panel 334 includes an elastane (e.g., Lycra) material 502 and a nylon (e.g., textured nylon) material 504. As illustrated, a bottom-most portion 390 of the panel 334 is constructed entirely from the elastane material 502, which is knitted onto all the needles. As also illustrated, the nylon material 504 is introduced in the upper portion 392 of the knitted panel 334. In the illustrated arrangement, in the upper portion 392 the elastane material 502 is tucked (e.g., half-gauge tucked, missing every other needle) and the nylon material 504 is knitted onto all the needles. The tucked stitches of the elastane material 502 provides greater bulk than knitted stitches. However, in other configurations, both materials could be knitted. The elastane material 502 and the nylon material 504 can interlock at times, such as every four courses, for example.

Figure 33A:
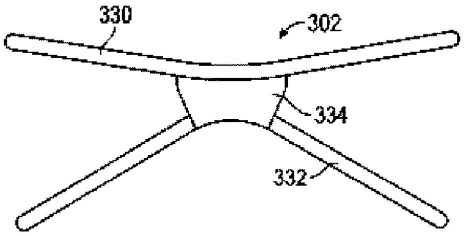
FIGS. 33*a*-33*l* illustrate various alternative rear portions of the headgear having a knitted panel.

FIGS. 33A-33I illustrate alternative configurations of the rear portion 302, which generally include upper strap(s) 330, lower strap(s), and a panel 334 or corresponding structures. The illustrated panels 334 can be partially or entirely knitted. In alternative arrangements, the panels 334 could be constructed from sheets of material, such as spacer fabric or other composite or suitable materials. FIG. 33*a* illustrates a rear portion 302 that is the same as or similar to the rear portion 302 of FIGS. 29-32, in which a single upper strap 330 is provided and a pair of lower straps 332 are provided. The panel 334 interrupts the lower straps 332. The upper strap 330 can be curved and the lower straps 332 can form a curve that is greater than a curve of the upper strap 330 relative to a horizontal line passing through the panel 334.

Figure 33B:
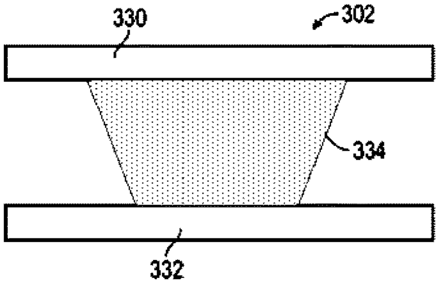
Figure 33C:
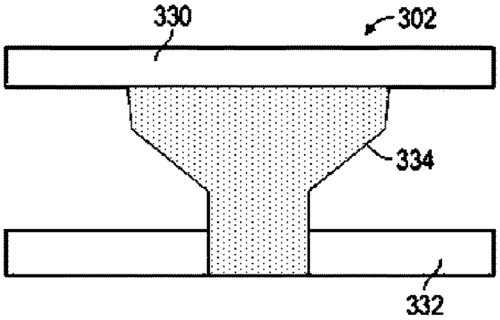
Figure 33D:
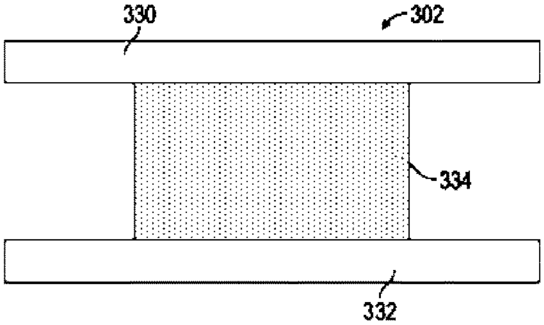
Figure 33E:
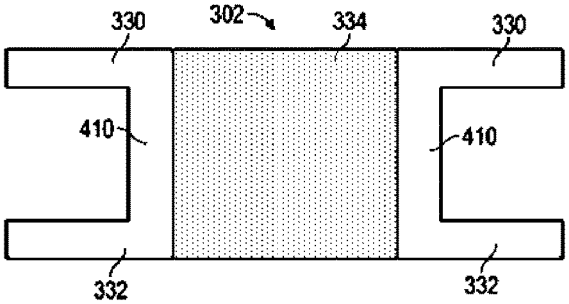

FIG. 33B illustrates a rear portion 302 in which both of the upper strap 330 and the lower strap 332 are uninterrupted. The rear panel 334 is tapered from top to bottom. The upper strap 330 and the lower strap 332 are straight as illustrated, but one or both could be curved. The rear portion 302 of FIG. 33C is similar to that of FIG. 33B, except the bottom strap 332 is interrupted by the panel 334 and the panel 334 includes a central tapered portion. The upper and lower portions of the panel 334 have parallel side edges. The rear portion 302 of FIG. 33D is similar to those of FIGS. 33B and 33C, except the rear panel 334 is not tapered, but is rectangular in shape. The rear portion 302 of FIG. 33E includes a rectangular panel 334. However, both the upper strap 330 and the lower strap 332 are interrupted by the panel 334. In addition, the straps 330, 332 include connecting portions 410 that extend between the straps 330, 332 along the sides of the panel 334. Thus, the straps 330, 332 can be formed by two portions, each of which defines a portion of the upper strap 330, a portion of the lower strap 332 and the connecting portion 410 therebetween.

Figure 33F:
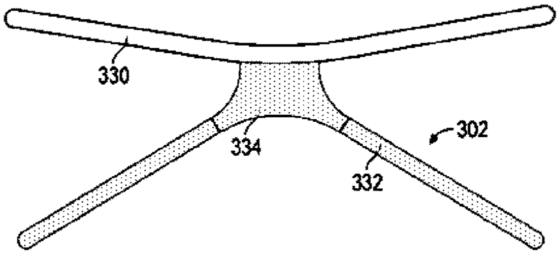
Figure 33G:
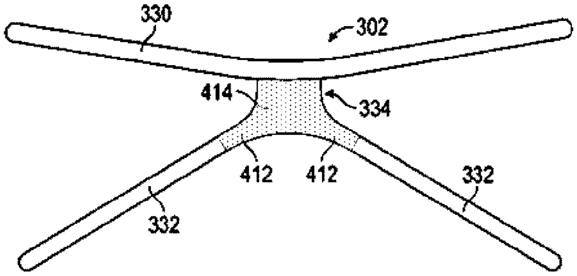
Figure 33H:
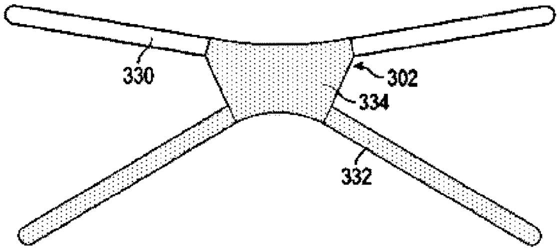

FIG. 33F illustrates a rear portion 302 similar to that of FIG. 33A. However, the rear portion of FIG. 33F includes knitted lower strap(s) 332 in addition to the knitted panel 334. FIG. 33G illustrates a rear portion 302 similar to that of FIG. 33A, except the knitted panel 334 forms lower strap portions 412 that extend from the main body portion 414 of the panel 334. The lower straps 332 connect to the strap extensions or strap portions 412 of the knitted panel 334. FIG. 33H illustrates a rear portion 302 that is similar to the rear portion of FIG. 33F, except the knitted panel 334/lower strap 332 portion interrupts the upper straps 330.

Figure 33I:
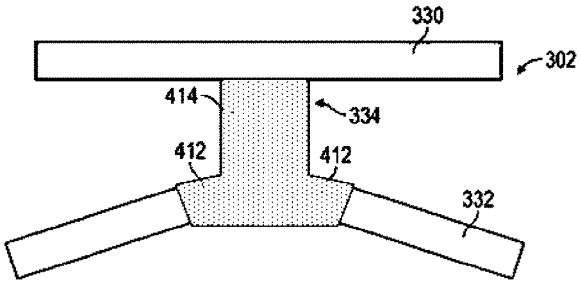

FIG. 33I illustrates a rear portion 302 that is similar to the rear portion 302 of FIG. 33C, except the panel 334 forms lower strap portions 412 similar to those of the rear portion 302 of FIG. 33G. The main body portion 414 of the panel 334 is generally rectangular such that the lower strap portions 412 and the main body portion 414 form an inverted T-shape.

Figure 33J:
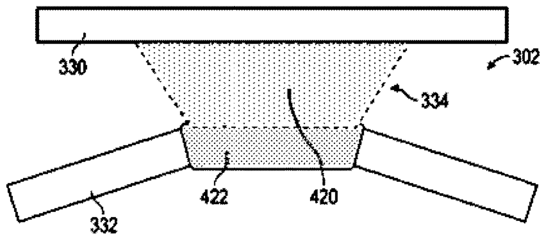

FIG. 33J illustrates a rear portion 302 that is similar to the rear portion 302 of FIG. 33A except the panel 334 includes regions of different stretch and/or porosity. For example, an upper section 420 of the panel 334 can have greater porosity and/or less stretch than a lower section 422 of the panel 334. In other configurations, the upper section 420 of the panel 334 can have greater stretch than the lower section 422. However, in such arrangements, it is preferred that the lower section 422 provides for some amount of stretch. In some configurations, the differences in the porosity and/or stretch (or other properties) can be accomplished by the knitting process, material selection, or both.

Figure 33K:
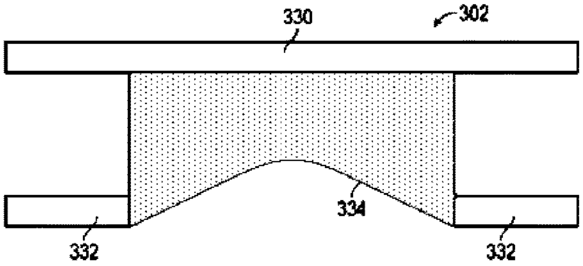

FIG. 33K illustrates a rear portion 302 similar to the rear portion 302 of FIG. 33A except the bottom edge of the panel 334 has a more pronounced curve to create a greater difference in height between the side portions of the panel 334 and a center portion of the panel 334. Although the lower straps 332 are illustrated as horizontal, they could be angled downwardly in a manner similar to the lower straps 332 of FIG. 33A.

Figure 33L:
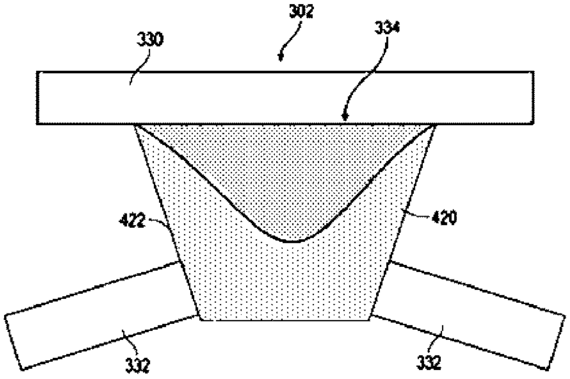

FIG. 33L illustrates a rear portion 302 similar to the rear portion 302 of FIG. 33J except that the upper section 420 and lower section 422 differ in shape relative to FIG. 33J. For example, in the rear portion 302 of FIG. 33L, the upper section 420 does not define side edges of the panel 334. Rather, the entireties of the side edges are defined by the lower section 422. In some configurations, the upper section 420 of the panel 334 can have greater porosity and/or less stretch than the lower section 422 of the panel 334. In other configurations, the upper section 420 of the panel 334 can have greater stretch than the lower section 422. However, in such arrangements, it is preferred that the lower section 422 provides for some amount of stretch.

Figure 34:
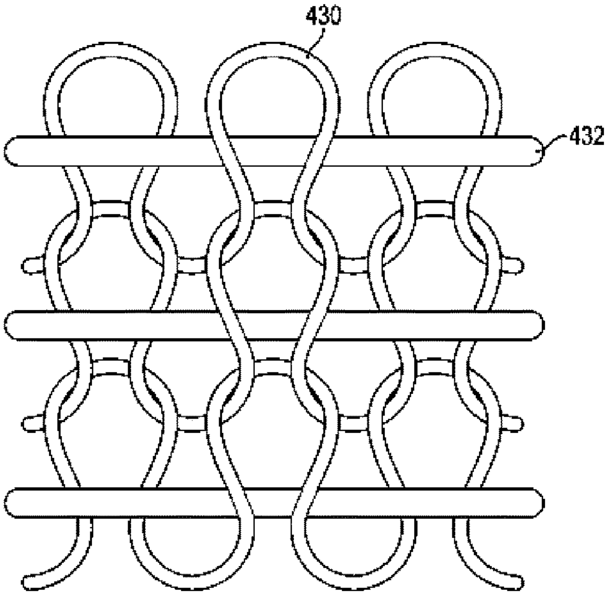
FIG. 34 illustrates an example alternative knitted construction.

FIG. 34 illustrates an example knitted structure that can be used to create in whole or in part knitted portions of the headgear 154, such as the rear panel 334. In the illustrated arrangement, the knitted structure is created by a first material 430, such as a material comprising nylon. A second material 432 can be inlayed in the knitted first material. The second material can have greater stretch than the first material. In some configurations, the second material can comprise elastane (e.g., Lycra). The inlay material is trapped by the knitted loops of the knitted material. Such an arrangement can provide for greater stretch of the panel 334 or other knitted portion, but can be coarse to the touch.

Knitted Cover

Figure 35:
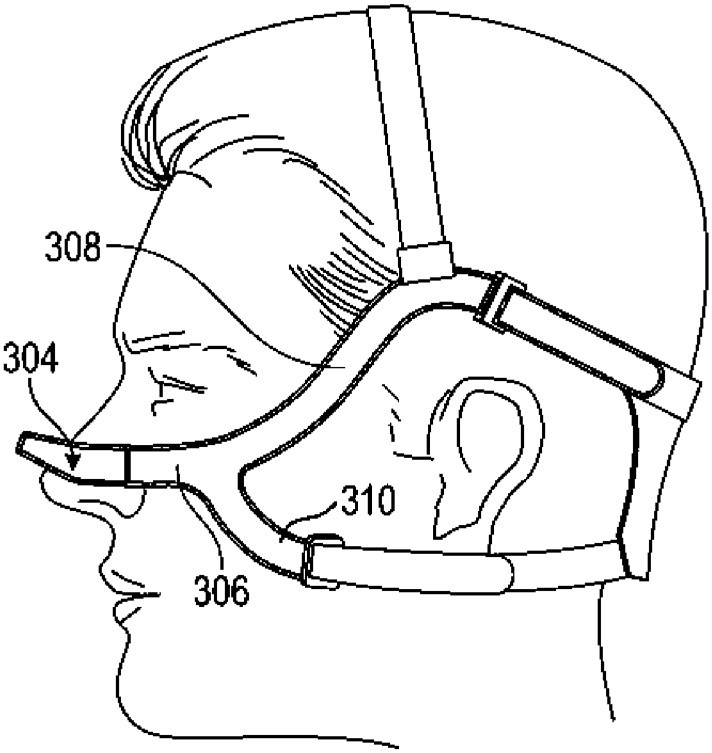
FIG. 35 is a side view of an alternative headgear arrangement having a front strap arrangement constructed as a composite of a knitted tubular cover permanently connected to an internal plastic core.
Figure 36A:
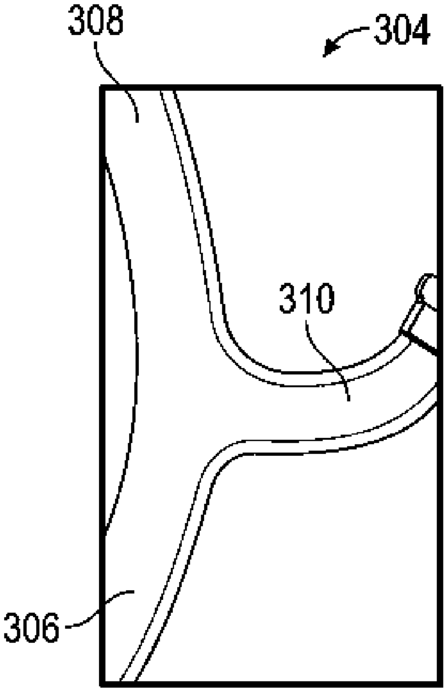
FIG. 36*a* is an enlarged view of the front strap arrangement of FIG. 35.
Figure 36B:
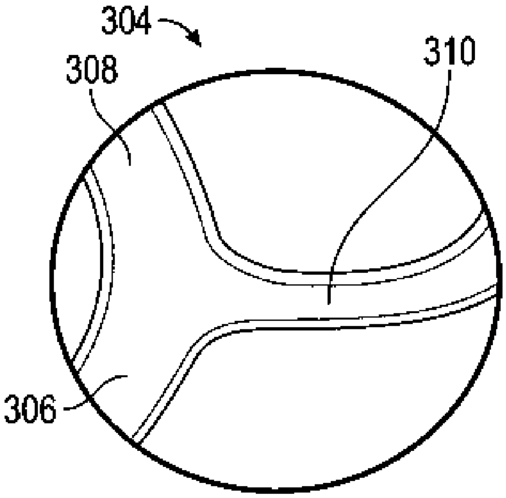
FIG. 36*b* is an enlarged view of a portion of the front strap arrangement shown in FIG. 36*a*.

FIGS. 35-36B illustrate a modified version of the headgear 154. In particular, the headgear 154 of FIGS. 35-36B includes a modified version of the front strap arrangement 304 described with primary reference to FIGS. 22-27. The front strap arrangement 304 can include the front strap portion 306, the upper strap portion 308 and the lower strap portion 310 constructed as a unitary structure. As described above, the front strap arrangement 304 can be constructed as a molded composite structure having at least one fabric layer and at least one plastic layer permanently connected to one another. In the illustrated arrangement, the front strap arrangement 304 is a molded composite structure having a tubular knitted structure 440 that defines inner and outer fabric layers on each side (interior and exterior—or toward and away from the user) of the plastic core.

In some configurations, the tubular knitted structure 440 can be formed by a suitable knitting process using suitable materials, such as the processes and materials described herein. The knitted structure 440 can be formed as a single piece including one or more of the front strap portion 306, the upper strap portion 308 and the lower strap portion 310. In other words, the knitted structure 440 can be formed, by knitting a single piece that includes a bifurcation from the front strap portion 306 into the upper and lower strap portions 308, 310. The front strap arrangement 304 can be formed as a unitary structure by the application of molten plastic into the space between the fabric layers within a mold and allowing the molten plastic to harden to form the plastic core in the shape of the mold cavity. In particular, the knitted structure 440 can be placed in a mold and molten plastic can be introduced into the interior space of the hollow knitted structure 440 and allowed to cool and harden.

The knitted structure 440 can be knitted into a shape that approximates or substantially matches the final shape of the front strap arrangement 304 as determined by the cavity of the mold tool. With such an arrangement, the stitch structure and knit direction generally or substantially matches the shape of the plastic core or the front strap arrangement 304 as determined by the cavity of the mold tool. The resulting front strap arrangement 304 possesses knitted edges that match the curvature of the plastic core and can reduce material build-up and/or bunching in comparison to fabric coverings made from flat sheet material. Although disclosed in the context of the front strap arrangement 304, other portions, straps or panels of the headgear could be similarly constructed.

In some configurations, the knitted structure 440 can be knitted so that the grain of the knitted structure 440 follows the shape in which the plastic core is molded. With such an arrangement, separation of stitches between the wales will be resisted and the shape of the strap will be maintained. In addition, arranging the grain to follow the direction of the plastic core minimizes the number of bind-off stitches required to create the knitted structure. Such a construction is advantageous to allow for fast and efficient construction.

Figure 53:
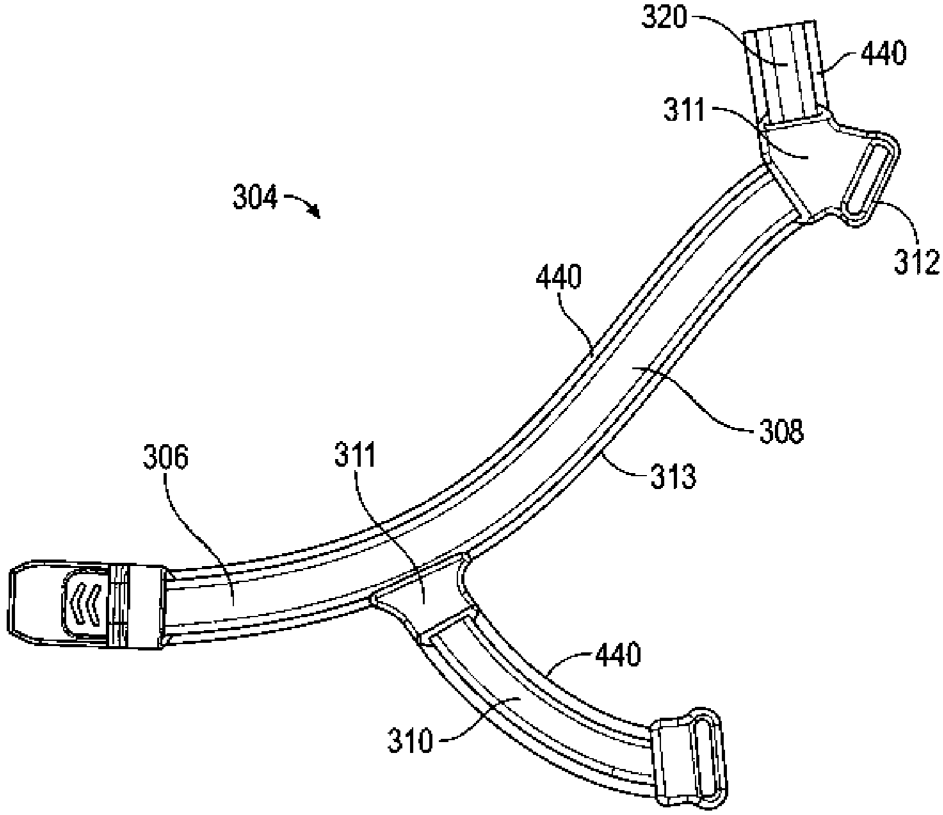
FIG. 53 is a side view of a portion of a modified version of the front strap arrangement shown in FIG. 35.

FIG. 53 illustrates a portion of a modified front strap arrangement 304 described above with primary reference to FIGS. 35-36B. Except as described below and/or apparent from the drawings, the two versions may otherwise be alike. In particular, the front strap arrangement 304 of FIG. 50 includes a front strap portion 306, upper strap portion 308, lower strap portion 310 and one of the first or second strap portions 320, 322 of the top strap arrangement 314. The front strap arrangement 304 can be constructed as a molded composite structure having at least one fabric layer and at least one plastic layer permanently connected to one another.

In this modified version of front strap arrangement 304, the front strap portion 306 and upper strap portion 308 are formed from a single continuous tubular knitted structure 440, and the lower strap portion 310 and first strap portion 320 are each formed from separate tubular knitted structures 440. This configuration avoids the need for knitting a bifurcated tubular structure and may simplify manufacture.

In some configurations, the front strap portion 306 and upper strap portion 308 may also be formed from separate tubular knitted structures 440, and/or the front strap portion 306 and lower strap portion 310 may alternatively be formed as a single continuous tubular knitted structure 440. In some configurations, one or more of the tubular knitted structures 440 may be knitted into a shape that approximates or substantially matches the final shape of the respective strap portion, as described above. In some configurations, one or more of the tubular knitted structures 440 may be knitted so that the grain direction varies along the length of the tubular knitted structure 440, as described above. One or more of the knitted structures 440 may differ from another knitted structure 440. For example, the tubular knitted structures 440 of the lower strap portion 310 and first strap portion 320 are a different color to the tubular knitted structure 440 of the combined front strap portion 306 and upper strap portion 308. The use of different colors may provide a visual cue which helps the user orient the headgear 154. In some configurations, two or more of the tubular knitted structures 440 may be identical to each other, except perhaps in length, and may each be cut to an appropriate length from the same stock of tubular knitted material.

Each of the tubular knitted structures 440 may be clamped by the edges 313 inside a mold, and molten plastic injected inside the tubular knitted structure 440. The molten plastic cools and hardens to form a plastic core in the shape of the mold cavity, as described above. The plastic core may have substantially planar opposing major surfaces with convex side edges devoid of sharp corners which may cause discomfort or facial marking. When removed from the mold, the outer edges 313 of the now partially flattened tubular knitted structure 440 are substantially devoid of the plastic material. This may leave the resulting strap portion with soft outer edges 313 which may improve user comfort and/or reduce facial marking. Each of the lower strap portion 310 and first strap portion 320 may then be placed, simultaneously or consecutively, in another mold with the combined front strap portion 306 and upper strap portion 308 in a desired arrangement, and joined by overmolding the respective strap portions 306, 308, 310 with joining portions 311 as shown. In some configurations, the plastic core and joining portions 311 may be formed from the same material. In some configurations, the plastic core and/or joining portions 311 may be formed from a resilient and relatively soft thermoplastic elastomeric material, such as PEBAX®. As shown in FIG. 50, the loop 312 of the upper strap portion 308 may form an integral part of the uppermost joining portion 311.

CONCLUSION

It should be emphasized that many variations and modifications may be made to the herein-described embodiments, the elements of which are to be understood as being among other acceptable examples. All such modifications and variations are intended to be included herein within the scope of this disclosure and protected by the following claims. Moreover, any of the steps described herein can be performed simultaneously or in an order different from the steps as ordered herein. Moreover, as should be apparent, the features and attributes of the specific embodiments disclosed herein may be combined in different ways to form additional embodiments, all of which fall within the scope of the present disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Moreover, the following terminology may have been used herein. The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" or "approximately" means that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "about 1 to about 3," "about 2 to about 4" and "about 3 to about 5," "1 to 3," "2 to 4," "3 to 5," etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

What is claimed is:

1. A cushion for a respiratory interface assembly, the cushion comprising:

a rim configured for attachment to the respiratory interface assembly;

a resilient side wall extending from the rim;

a resilient end wall extending inwardly from the resilient side wall, the resilient end wall defining a sealing surface to seal with a user's face and an opening configured to receive at least one of a nose and a mouth of the user's face, in use; and a pair of elongate thickened portions each having a wall thickness that is greater than a wall thickness of adjacent portions of the resilient side wall or the resilient end wall, the pair of elongate thickened portions each extending from a first end at or adjacent or near to respective lower corners of the resilient side wall at or adjacent or near to the rim, to a second end at or adjacent or near to the resilient end wall on respective opposing sides of the opening, wherein the pair of elongate thickened portions each curve upwardly at a transition of the cushion from the resilient side wall to the resilient end wall.

2. The cushion of claim 1, wherein the pair of elongate thickened portions diverge from the first ends towards respective intermediate portions of the pair of elongate thickened portions.

3. The cushion of claim 1, wherein the pair of elongate thickened portions converge from respective intermediate portions of the pair of elongate thickened portions towards the second ends.

4. The cushion of claim 1, wherein the pair of elongate thickened portions comprise respective intermediate portions intermediate the respective first ends and the respective second ends, and the pair of elongate thickened portions converge towards each other from the intermediate portions towards the first ends and the second ends.

5. The cushion of claim 1, wherein the pair of elongate thickened portions extend inwardly from an interior surface of the cushion.

6. The cushion of claim 1, wherein the wall thickness of the pair of elongate thickened portions is thicker than the wall thickness of the adjacent portions of the resilient side wall or the resilient end wall by between about 0.1 and 0.6 mm.

7. The cushion of claim 6, wherein the wall thickness of the pair of elongate thickened portions is thicker than the wall thickness of the adjacent portions of the resilient side wall or the resilient end wall by between about 0.1 and 0.3 mm.

8. The cushion of claim 7, wherein the wall thickness of the pair of elongate thickened portions is thicker than the wall thickness of the adjacent portions of the resilient side wall or the resilient end wall by about 0.2 mm.

9. The cushion of claim 1, wherein the wall thickness of the pair of elongate thickened portions is about 1.2 mm.

10. The cushion of claim 1, wherein the wall thickness of the pair of elongate thickened portions is uniform along a length of the pair of elongate thickened portions.

11. The cushion of claim 1, wherein the wall thickness of the pair of elongate thickened portions, relative to the adjacent portions of the resilient side wall or the resilient end wall, is uniform along a length of the pair of elongate thickened portions.

12. The cushion of claim 1, wherein the pair of elongate thickened portions are spaced from the opening by at least 4 mm.

13. The cushion of claim 12, wherein the pair of elongate thickened portions are spaced from the opening by between about 5 and 6 mm.

14. The cushion of claim 13, wherein the pair of elongate thickened portions are spaced from the opening by between about 5.2 and 5.5 mm.

15. The cushion of claim 1, wherein the pair of elongate thickened portions are each curved in a direction normal to their respective major surfaces.

16. The cushion of claim 1, wherein the pair of elongate thickened portions each form a plane curve.

17. The cushion of claim 1, wherein a width of the pair of elongate thickened portions is narrower at the first ends than at the second ends.

18. The cushion of claim 17, wherein the width of the pair of elongate thickened portions is at least 50% greater at the second ends than at the first ends.

19. The cushion of claim 17, wherein the width of the pair of elongate thickened portions is between about 4 and 6 mm at the first ends, and between about 7 and 8 mm at the second ends.

20. The cushion of claim 17, wherein the width of the pair of elongate thickened portions tapers from the second ends towards the first ends.

21. The cushion of claim 1, wherein the pair of elongate thickened portions are each configured to extend rearwardly from the first end towards the user's face, in use, before curving upwardly and terminating at the second end at respective cheek regions of the resilient end wall configured to engage respective cheeks of the user's face.

22. The cushion of claim 1, comprising thickened corner portions at or adjacent the respective lower corners of the resilient side wall.

23. The cushion of claim 22, wherein the resilient side wall tapers upwardly from the thickened corner portions over a first distance and tapers downwardly from the thickened corner portions over a second distance, and the first distance is shorter than the second distance.

24. The cushion of claim 22, wherein the first ends of the pair of elongate thickened portions are located vertically below and spaced from the respective thickened corner portions.

25. The cushion of claim 1, wherein the second ends of the pair of elongate thickened portions are located laterally adjacent a vertical mid-point of the opening.

26. The cushion of claim 1, wherein the cushion comprises a nasal cushion, the opening is configured to receive the nose, and the resilient end wall comprises:

an upper region configured to extend over the nose, a lower region configured to contact the user's face at a location above a vermillion border and below nares of the nose, and two separate cheek regions each extending between the upper region and the lower region and configured to contact at least one of a medial cheek surface and a lateral nose surface on respective sides of the user's face, wherein the second ends of the pair of elongate thickened portions are positioned in the respective cheek regions of the resilient end wall.

27. The cushion of claim 1, wherein an upper portion of the cushion is configured to pivot relative to a lower portion of the cushion about a hinge region to allow pivotal movement of the upper portion of the cushion in a forward direction towards or beyond the rim, in use.

28. The cushion of claim 27, wherein the second ends of the pair of elongate thickened portions are positioned above the hinge region.

29. A cushion for a respiratory interface assembly, the cushion comprising:
- a rim configured for attachment to the respiratory interface assembly;
- a resilient side wall extending from the rim;
- a resilient end wall extending inwardly from the resilient side wall, the resilient end wall defining a sealing surface to seal with a user's face and an opening configured to receive at least one of a nose and a mouth of the user's face, in use; and
- a pair of elongate thickened portions, the pair of elongate thickened portions each extending from a first end at or adjacent or near to respective lower corners of the resilient side wall at or adjacent or near to the rim, to a second end at or adjacent or near to the resilient end wall on respective opposing sides of the opening;
- a reinforcement positioned along the resilient side wall, the reinforcement comprising a lower region on each lateral side of the cushion and a connecting portion extending around an upper portion of the cushion between the lower regions;
- wherein the second ends of the pair of elongate thickened portions are located vertically above, and horizontally inwardly from, the respective lower regions of the reinforcement.

30. The cushion of claim 29, wherein the reinforcement comprises a thickened band which extends inwardly from an interior surface of the cushion.

31. The cushion of claim 29, wherein the resilient side wall comprises a region of reduced stiffness between the reinforcement and the rim.

32. The cushion of claim 31, wherein the region of reduced stiffness is configured to roll toward a front of the respiratory interface assembly, in use.

33. A cushion for a respiratory interface assembly of a respiratory therapy system supplying breathing gases to a user for positive airway pressure or non-invasive ventilation therapy, the cushion comprising:
- a rim configured for attachment to the respiratory interface assembly;
- a resilient side wall configured to extend in a rearward direction from the rim towards the user, in use; and
- a resilient end wall extending inwardly from the resilient side wall, the resilient end wall defining a sealing surface to seal with a face of the user and an opening configured to receive at least one of a nose and a mouth of the user, in use; and
- a pair of elongate thickened portions in at least the resilient side wall of the cushion each having a wall thickness that is greater than a wall thickness of adjacent portions of the resilient side wall or the resilient end wall, wherein the pair of elongate thickened portions are configured to diverge from each other in the rearward direction from at or adjacent or near to the rim, and wherein the pair of elongate thickened portions are configured to converge towards each other in an upwards direction.

34. The cushion of claim 33, wherein the pair of elongate thickened portions extend into the resilient end wall.

35. The cushion of claim 34, wherein the pair of elongate thickened portions terminate in the resilient end wall on opposing sides of the opening.

36. The cushion of claim 34, wherein a lower region of the resilient end wall between the pair of elongate thickened portions is configured to contact the face of the user above a vermillion border and below the user's nares.

37. The cushion of claim 36, wherein the lower region of the resilient end wall between the pair of elongate thickened portions is configured to stretch, in use.

38. The cushion of claim 33, wherein an upper portion of the cushion is configured to pivot relative to the lower portion of the cushion about a hinge region to allow pivotal movement of the upper portion of the cushion in a forward direction towards or beyond the rim, in use.

39. A respiratory interface assembly for a respiratory therapy system supplying breathing gases to a user for positive airway pressure or non-invasive ventilation therapy, the respiratory interface assembly comprising:
- an interface configured to deliver the breathing gases to an airway of the user, the interface comprising:
  - a frame;
  - a housing permanently connected or removably connectable to the frame; and
  - a cushion comprising:
    - a rim permanently connected or removably connectable to the housing;
    - a resilient side wall extending rearwardly from the rim;
    - a resilient end wall extending inwardly from a rearward end of the resilient side wall, wherein the housing, the resilient side wall and the resilient end wall in combination define a breathing chamber, the resilient end wall defines a sealing surface configured to seal with a face of the user, and the resilient end wall defines an opening to the breathing chamber configured to receive at least one of a nose and a mouth of the user, in use; and
    - a pair of elongate thickened portions each having a wall thickness that is greater than a wall thickness of surrounding portions of the resilient side wall or the resilient end wall, each of the pair of elongate thickened portions comprising a first end and a second end, wherein the pair of elongate thickened portions are configured to extend rearwardly from the first end in the resilient side wall at or adjacent or near to the housing, to the second end in the resilient end wall on respective opposing sides of the opening, and wherein the pair of elongate thickened portions are configured to diverge rearwardly and converge upwardly; and
- headgear permanently connected or removably connectable to the frame to secure the interface in place on the user.

40. The respiratory interface assembly of claim 39, wherein an upper portion of the cushion is configured to pivot relative to a lower portion of the cushion about a hinge region to allow pivotal movement of the upper portion of the cushion in a forward direction towards the housing, in use.

* * * * *